(12) United States Patent
Li et al.

(10) Patent No.: US 7,732,165 B2
(45) Date of Patent: Jun. 8, 2010

(54) BIOMOLECULE PARTITION MOTIFS AND USES THEREOF

(75) Inventors: Min Li, Baltimore, MD (US); Sojin Shikano, College Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 600 days.

(21) Appl. No.: 11/435,301

(22) Filed: May 15, 2006

(65) Prior Publication Data
US 2007/0031924 A1     Feb. 8, 2007

Related U.S. Application Data

(63) Continuation of application No. PCT/US2004/039285, filed on Nov. 22, 2004.

(60) Provisional application No. 60/524,380, filed on Nov. 21, 2003.

(51) Int. Cl.
| | |
|---|---|
| C12N 15/11 | (2006.01) |
| C12N 15/85 | (2006.01) |
| C12N 15/63 | (2006.01) |
| C07H 21/04 | (2006.01) |

(52) U.S. Cl. .................... 435/69.1; 435/325; 435/320.1; 536/23.4

(58) Field of Classification Search .................... None
See application file for complete search history.

(56) References Cited

U.S. PATENT DOCUMENTS

| 5,856,155 A | 1/1999 | Li |
| 6,190,856 B1 | 2/2001 | Li |

FOREIGN PATENT DOCUMENTS

| WO | WO-98/23781 | 6/1998 |
| WO | WO-01/14539 A2 | 3/2001 |

OTHER PUBLICATIONS

Shikano et al., Genetic isolation of transport signals directing cell surface expression. Nature Cell Biology, 7:985-992, 2005.*
Nishimura et al. The Journal of Biological Chemistry, vol. 274, No. 22, Issue May 28, 1999, pp. 15937-15964.
Gestwicki et al., Science, 306:865-869 (2004).

* cited by examiner

*Primary Examiner*—Ruixiang Li
(74) *Attorney, Agent, or Firm*—Edwards Angell Palmer & Dodge LLP; Peter F. Corless; Jonathan M. Sparks

(57) ABSTRACT

The invention provides amino acid sequence motifs (e.g., biomolecule partition motifs) that can direct targeting of intracellular polypeptides to and through membranes, including cell surface membranes.

12 Claims, 22 Drawing Sheets

| Group 1 | | Group 2 | | Group 3 | |
|---|---|---|---|---|---|
| #15 | MGAVRGWC | #20 | DMLRSHWC | #4 | RGRSWTY |
| #16 | KCVRSGWC | #22 | RMVYSGWC | #83 | RLRRGWTV |
| #25 | AEVQRVMC | #26 | LSVVERWC | #95 | GHGRRWTV |
| #33 | RTWVRINC | #119 | GYTVSIWC | #135 | RRKTV |
| #49 | GRRLIGWC | #73 | RRAKNEWC | | |
| #65 | MRLWGMWC | #102 | VLFMRMWC | | |
| #68 | SFLSSQWC | #111 | DRVLRLWC | | |
| #28 | MILYSMIC | #20 | VVLAQMIC | | |
| #74 | RNMENWC | #157 | ETLASWQC | | |
| #86 | CRTRGQWC | #53 | EWVWRYLV | | |
| #98 | LKSLKEWC | #78 | RSRGCKTV | | |
| #111 | DRVLRLWG | #94 | MSDRAMTV | | |
| #119 | KALKGVWG | #13 | LWYMSNRG | | |
| #126 | WKLVGSFG | #88 | NYVLGLLA | | |
| #46 | EKMGRLIC | #120 | LVRRSITF | | |
| #39 | ESTRRVTV | #145 | SRDRRKTY | | |
| #66 | GNARSLTV | #163 | EMSTIWWL | | |
| #21 | PGHGSLKG | #192 | IRVSVGLS | | |
| #32 | ERRPHSWG | #204 | PLVLRWIR | | |
| #181 | RCRGVNCK | | | | |
| #186 | SAARYQTS | | | | |
| #36 | MWLVGGIW | | | | |
| #42 | NRETEEHL | | | | |
| #45 | EVAISQRL | | | | |
| #55 | GQRFASWC | | | | |
| #70 | PCRSWPLK | | | | |
| #79 | WFIAGFFS | | | | |
| #80 | GHVRSAPW | | | | |
| #84 | EIGLEMSA | | | | |
| #112 | LPQLSVTW | | | | |
| #121 | TIQTLNQI | | | | |
| #123 | RKRWGMII | | | | |
| #129 | DVESMCRR | | | | |
| #137 | NGNEGQNS | | | | |
| #147 | EVRRRVTW | | | | |
| #148 | EKYLQLLD | | | | |
| #160 | DEAPMMGM | | | | |
| #162 | EVMGAAAW | | | | |
| #165 | MQPRWMVH | | | | |
| #206 | DRLGDDTR | | | | |
| #175 | TMLSKTIY | | | | |
| #179 | GLKWDVRW | | | | |

FIG. 2A

4# RGRSWTY

120# LVRRSITF

83# RLRRGWTY

135# RRKTV

95# GHGRGHSW

145# SRDRRKTY

Kir2.1-RKR-RGRSWTY

Kir2.1-RKR-RGRSWTY-AAA

Native 5WTY-like C-terminal Sequences

―R G R S W T Y ― COOH
 -7 -6 -5 -4 -3 -2 -1

| Criteria | H_sapiens | M_musculus | R_norvegicus | D_melanogaster | C_elegans | S_cerevisiae |
|---|---|---|---|---|---|---|
| None | 27175 | 26510 | 22850 | 18759 | 21136 | 5845 |
| Membrane protein keywords | 3263 | 3521 | 3768 | 285 | 2782 | 581 |
| Pos-2 = T or S | 528 | 578 | 640 | | 348 | 98 |
| Pos-10 to -a contains RR RXR, KK or KXK | 63 | 93 | 120 | 17 | 40 | 11 |
| Pos-4 or -6 contains R or K | 41 | 62 | 86 | | 25 | 7 |

FIG. 7A

BIOMOLECULE PARTITION MOTIFS AND USES THEREOF

RELATED APPLICATIONS/PATENTS & INCORPORATION BY REFERENCE

This application is a continuation of PCT/US04/39285, filed on Nov. 22, 2004 which claims the benefit of U.S. Provisional Application Ser. No. 60/524,380, filed on Nov. 21, 2003, the entire contents of the aforementioned applications are incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself, and, each of these documents or references ("herein-cited references"), as well as each document or reference cited in each of the herein-cited references (including any manufacturer's specifications, instructions, etc.), is hereby expressly incorporated herein by reference.

BACKGROUND OF THE INVENTION

Membrane proteins represent approximately 30% of the proteome in both prokaryotes and eukaryotes (Wallin and von Heijne, 1998). One of the important steps in membrane protein kinesis is trafficking to the correct site of action. Abnormal protein folding and trafficking is associated with a growing number of diseases (Thomas et al., 1995, Dobson, 2001, Radford et al., 1999). Prominent biogenesis steps include two transport events: anterograde transport and retrograde transport. The former represents a forward progression of vesicle movement toward the cell surface. The latter represents a process of reversal—vesicular trafficking to retrieve selectively marked proteins to the ER (Bonifacino and Glick, 2004).

Due to sequential folding steps and "quality" checks, even slight changes in protein structure or oligomeric state may be detected and, therefore, prevent trafficking to the site of action. The exit from ER to cell surface takes place when the proteins are appropriately assembled. A cell-surface protein contains a "zipcode" that uniquely tags for cell-surface expression. Improper folding or incomplete subunit assembly exposes a molecular feature (structure or sequence) that is recognized by the retention/retrieval machinery. Because little is known about the surface expression "zipcode," either in terms of signal motifs or of the molecular mechanism, the working of these two opposing forces, ER localization vs. surface localization, in mediating membrane protein expression requires further investigation.

Expression of membrane receptors on the cell surface is a highly regulated event. Signal motifs have been identified that are designed to confer spatial localization of newly synthesized proteins to ER for their final activity or to a transitional compartment before assembly with other proteins and trafficking to the cell surface (Mellman and Warren, 2000). Specific sequences, such as KKXX and RXR motifs, have been identified for their roles in conferring ER localization of membrane proteins (Nilsson et al., 1989; Zerangue et al., 1999). Signal motifs that promote surface expression of membrane proteins have also been identified, including DXE (Nishimura and Balch, 1997) and FCYENE (SEQ ID NO: 249) (Ma et al., 2001). These motifs are thought to function at the step of ER exit.

The existing evidence supports the notion that the opposing forces of ER exit (leading to surface expression) and retrieval (conferring ER localization) operate in two sequential biogenesis steps. Consistent with this view, the retrograde transport, a later step than the ER exit step, is naturally dominant. The selective exit from retrograde transport that allows for protein to progress to the cell surface may be achieved by at least three mechanisms. First, the ER localization signals, such as dibasic and RKR motifs, may be masked as a result of macromolecular assembly of multiple subunits. Second, in addition to the physical masking, the ER localization signals are sensitive to the proximity to cytoplasmic leaflets of membrane. Hence, the ER localization efficiency could be modified by re-positioning a signal into a different zone as a result of protein-protein interaction or folding. The third mechanism is to recruit modular proteins which bind competitively with COPI, the retrograde transport machinery.

To explore possible signal motifs and regulatory pathways of exiting from retrograde transport, a genetic screen was designed to evaluate random peptide sequences for their ability to override ER localization activity and to direct surface expression.

SUMMARY OF THE INVENTION

It has now been determined that amino acid sequence motifs, referred to herein as biomolecule partition motifs, can direct targeting of intracellular polypeptides to and through membranes, including cell surface membranes. Addition of a biomolecular partition motif can alter the expression level and subcellular location of the polypeptide.

In one embodiment, the invention provides a recombinant polynucleotide that encodes a cell surface polypeptide comprising a biomolecule partition motif, wherein the biomolecule partition motif is not present in the native polypeptide.

Cell surface polypeptides include but are not limited to antibodies, G-protein-coupled receptors, cytokine receptors, membrane-bound transport proteins and membrane bound enzymes.

In specific embodiments, the biomolecule partition motif can be a SWTY motif (SEQ ID NO: 250).

In another embodiment, the invention provides a transformed cell comprising a recombinant polynucleotide that encodes a cell surface polypeptide and a biomolecule partition motif, wherein the biomolecule partition motif is not present in the native polypeptide.

In yet another embodiment, the invention provides a method of obtaining a polypeptide from the surface of a cell, the method comprising: expressing a polypeptide having at least one non-native biomolecule partition motif in a cell under conditions sufficient to provide the polypeptide to the surface of the cell; and isolating the polypeptide, thereby obtaining the polypeptide from the surface of the cell.

In specific embodiments, a post-translational modification of the polypeptide is modified in comparison to a post-translational modification of the native polypeptide.

In one specific embodiment, the glycosylation pattern of the polypeptide is reduced in comparison to a glycosylation pattern of the native polypeptide. The glycosylation pattern can be an O-linked glycosylation pattern.

In one embodiment, the polypeptide encodes a therapeutic biologic. The therapeutic biologic can be but is not limited to an antibody, GM-CSF, M-CSF, G-CSF, interleukins-1 through 29, TNFα, interferon α, interferon β, interferon γ, insulin, human growth hormone, erythropoietin and fragments thereof.

In yet another embodiment, the invention provides a method of providing a polypeptide to the surface of a cell, the method comprising: attaching a biomolecule partition motif to the C-terminus of a nucleic acid sequence encoding the polypeptide; and introducing the nucleic acid sequence into the cell, wherein the polypeptide is expressed from the nucleic acid sequence, processed in the endoplasmic reticulum, secreted therefrom and inserted into the extracellular membrane, thereby providing the polypeptide to the surface of the cell.

In yet another embodiment, the invention provides a method of expressing a polypeptide on the surface of a cell, the method comprising: expressing polypeptides having at least one non-native biomolecule partition motif in a cell under conditions sufficient to provide the polypeptides to the surface of the cell, wherein the amount of polypeptides on the surface of the cell is increased relative to the amount of polypeptides on the surface of a cell expressing polypeptides that do not have at least one non-native biomolecule partition motif.

In yet another embodiment, the invention provides a method of increasing polypeptide expression on the surface of a cell, the method comprising: attaching at least one biomolecule partition motif to the polypeptides; and providing the polypeptides to the surface of the cell, wherein the amount of polypeptides on the surface of the cell is increased relative to the amount of polypeptides on the surface of a cell expressing polypeptides that do not have the at least one biomolecule partition motif attached.

In a specific embodiment, the biomolecule partition motif is attached to the polypeptide by a tag having affinity for the polypeptide.

In another specific embodiment, the biomolecule partition motif is attached to the polypeptide through formation of a complex with another polypeptide having the biomolecule partition motif.

In yet another specific embodiment, the polypeptides would form intracellular aggregates without inclusion of the non-native biomolecule partition motif.

In yet another embodiment, the invention provides a method of producing an immunogen on the surface of a cell, the method comprising: expressing a polypeptide encoding an immunogenic determinant and at least one non-native biomolecule partition motif in a cell under conditions sufficient to provide the polypeptide to the surface of the cell, thereby producing an immunogen on the surface of the cell.

In specific embodiments, the immunogen can be derived from viral polypeptides, bacterial polypeptides, fungal polypeptides and fragments thereof.

In yet another embodiment, the invention provides a DNA vaccine composition comprising an expression vector comprising a recombinant polynucleotide that encodes an immunogenic polypeptide and one or more biomolecule partition motifs, wherein the biomolecule partition motifs are not present in the native immunogenic polypeptide, and a suitable pharmaceutical excipient.

In specific embodiments, the immunogenic polypeptide can be a viral polypeptide, bacterial polypeptide, fungal polypeptide or fragments thereof.

In yet another embodiment, the invention provides a method of treating a disorder characterized by intracellular retention of polypeptides in a subject, the method comprising: introducing a biomolecule partition motif into the coding region of a gene that encodes a cell surface polypeptide; and expressing the polypeptide under conditions sufficient to provide the polypeptide to the surface of the cell, thereby treating the disorder in the subject.

In yet another embodiment, the invention provides a method of treating a disorder characterized by intracellular retention of polypeptides in a subject, the method comprising: attaching a biomolecule partition motif to the C-terminus of the polypeptides; and providing the polypeptides to the surface of the cell, thereby treating the disorder in the subject.

The disorders can be but are not limited to acute coronary syndrome, cystic fibrosis, Alzheimer's disease, diabetes mellitus, nephrogenic diabetes, Dubin-Johnson Syndrome and autosomal dominant retinitis pigmentosa.

The polypeptides can be but are not limited to a potassium channel (e.g., the hERG potassium channel), β-amyloid protein, cystic fibrosis transmembrane regulator, p-glycoprotein, insulin receptor, water channel aquaporin-2, multi drug resistance protein and rhodopsin.

Other aspects of the invention are described in or are obvious from the following disclosure, and are within the ambit of the invention.

DETAILED DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which:

FIG. 1A schematically depicts the hypothesis of cell surface expression potential (SEP). The plot displays a hypothetical distribution of sequences from a random peptide library (vertical axis) as a function of their ability to confer either surface expression or intracellular retention (horizontal axis). The shape and symmetry of the graph need not be as diagrammed. Two dashed lines represent hypothetical thresholds of SEP values for ER localization signals (such as RKR) and forward transport signals (such as DXE and FCYENE (SEQ ID NO: 249)). The arrows represent their SEP values in reference to the thresholds.

FIG. 2A lists deduced amino acid sequences from an X8 random peptide screen. The sequences are grouped according to their ability to confer surface expression of Kir2.1-RKR, with Group 1 showing essentially no detectable surface expression (peptides disclosed as SEQ ID NOS 266-286 in the left most column respectively in order of appearance and peptides disclosed as SEQ ID NOS 287-307 in the adjacent right hand column respectively in order of appearance), Group 2 capable of directing surface expression at a level similar to that of wild-type Kir2.1 or Kir2.1-RAA control (SEQ ID NOS 308-321, 9, 10, & 322-324 respectively in order of appearance), and Group 3 conferring surface expression levels higher than that of wild-type (SEQ ID NOS 1, 6, 7, & 8 respectively in order of appearance).

Figure 2B:
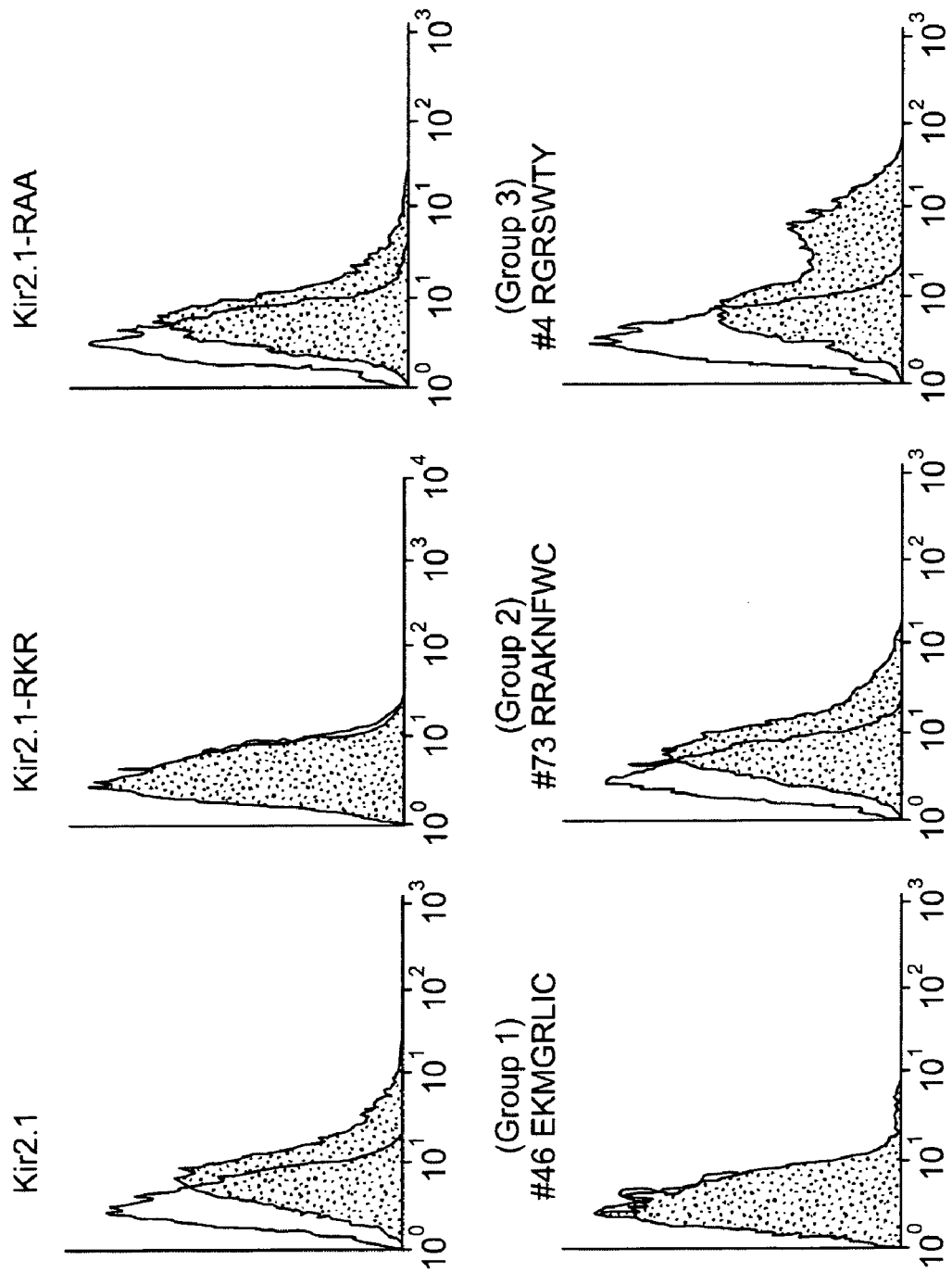

FIG. 2B shows flow cytometry analyses of HA-tagged Kir2.1 channel in HEK293 cells. The top three panels show Kir2.1, Kir2.1-RKR and Kir2.1-RAA expression as indicated. Grey areas are staining signals. Mock-transfected cells stained with primary and secondary antibodies served as background (unfilled areas). The lower three panels are flow cytometry signals from selected clones of Groups 1 (SEQ ID NO: 280), 2 (SEQ ID NO: 312) and 3 (SEQ ID NO: 1). The deduced amino acid sequences are as indicated.

Figure 2C:
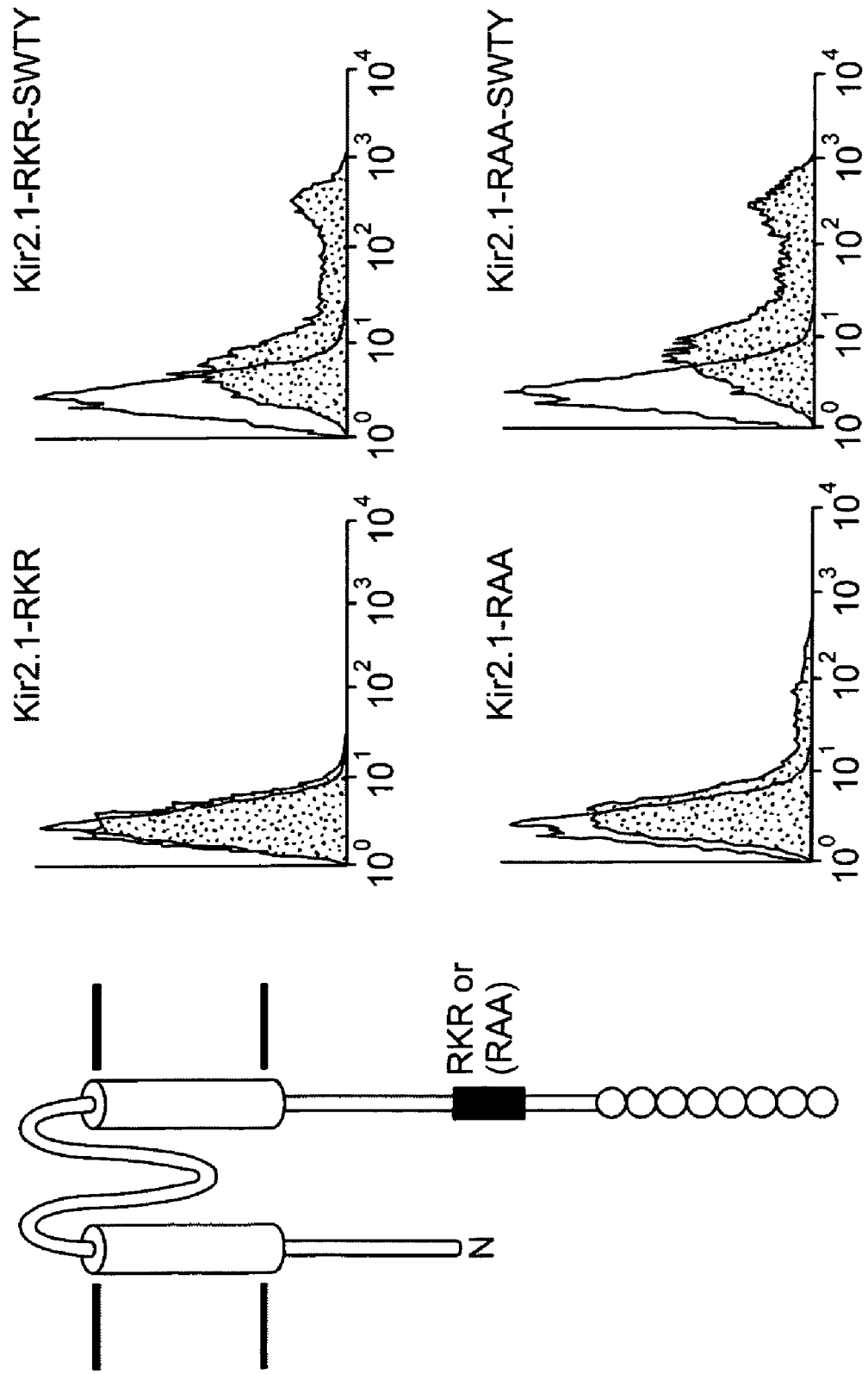

FIG. 2C depicts, on the left, a schematic diagram of Kir2.1-RKR-SWTY (peptide disclosed as SEQ ID NO: 251) and, on the right, flow cytometry analyses comparing surface expression of SWTY-tagged Kir2.1 (peptide disclosed as SEQ ID NO: 250) with the RKR or the RAA motif (RKR-SWTY peptide disclosed as SEQ ID NO: 251 & RAA-SWTY peptide disclosed as SEQ ID NO: 257).

Figure 2D:
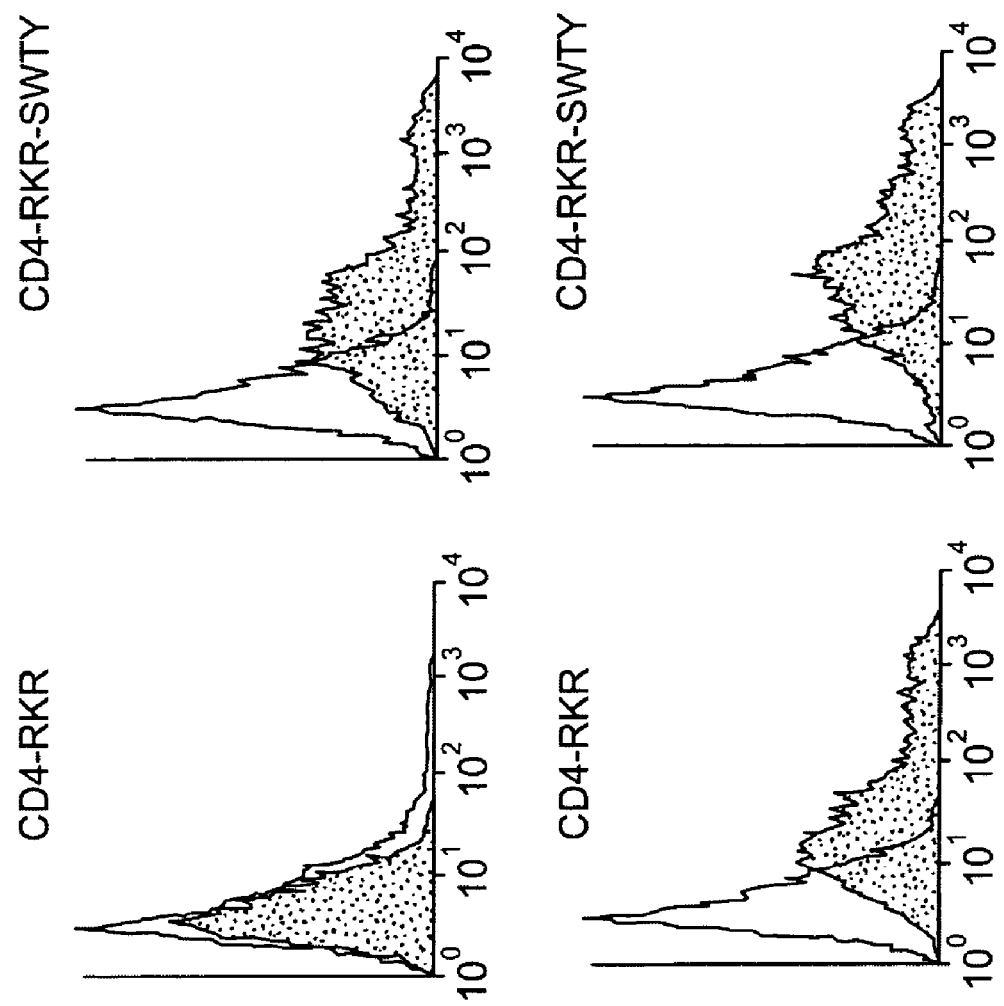
Figure 2D:
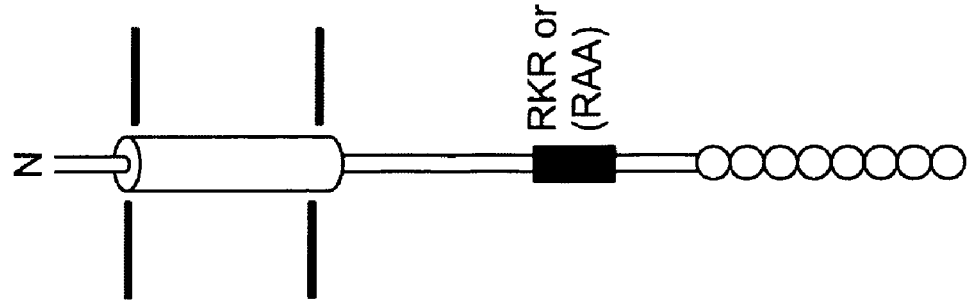

FIG. 2D depicts, on the left, a schematic diagram of CD4-RKR-SWTY (peptide disclosed as SEQ ID NO: 251) and, on the right, flow cytometry analyses comparing surface expression of SWTY-tagged CD4 (peptide disclosed as SEQ ID NO: 250) with the RKR or the RAA motif (RKR-SWTY peptide disclosed as SEQ ID NO: 251 & RAA-SWTY peptide disclosed as SEQ ID NO: 257).

Figure 3A:
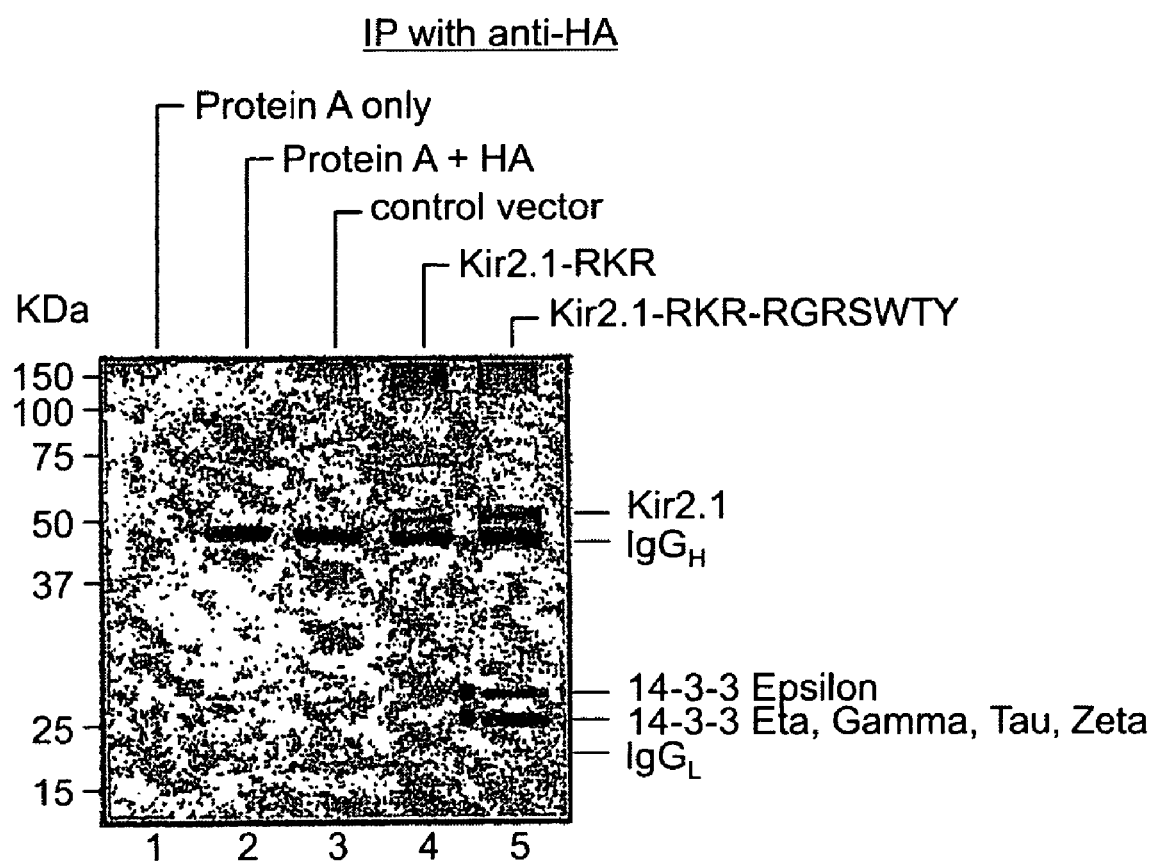

FIG. 3A shows an image of a silver staining gel of proteins isolated from immunoprecipitation of transfected HEK293 cells. Lane 1 shows protein A alone; lane 2 shows protein A plus anti-HA antibody; lanes 3-5 show anti-HA precipitation from lysates of cells transfected with mock vector (lane 3), Kir2.1-RKR construct (lane 4) or Kir2.1-RKR-RGRSWTY (peptide disclosed as SEQ ID NO: 252) construct (lane 5). The proteins confirmed by MALDI-TOF are identified on the right, and molecular weight standards in kDa are shown on the left.

Figure 3B:
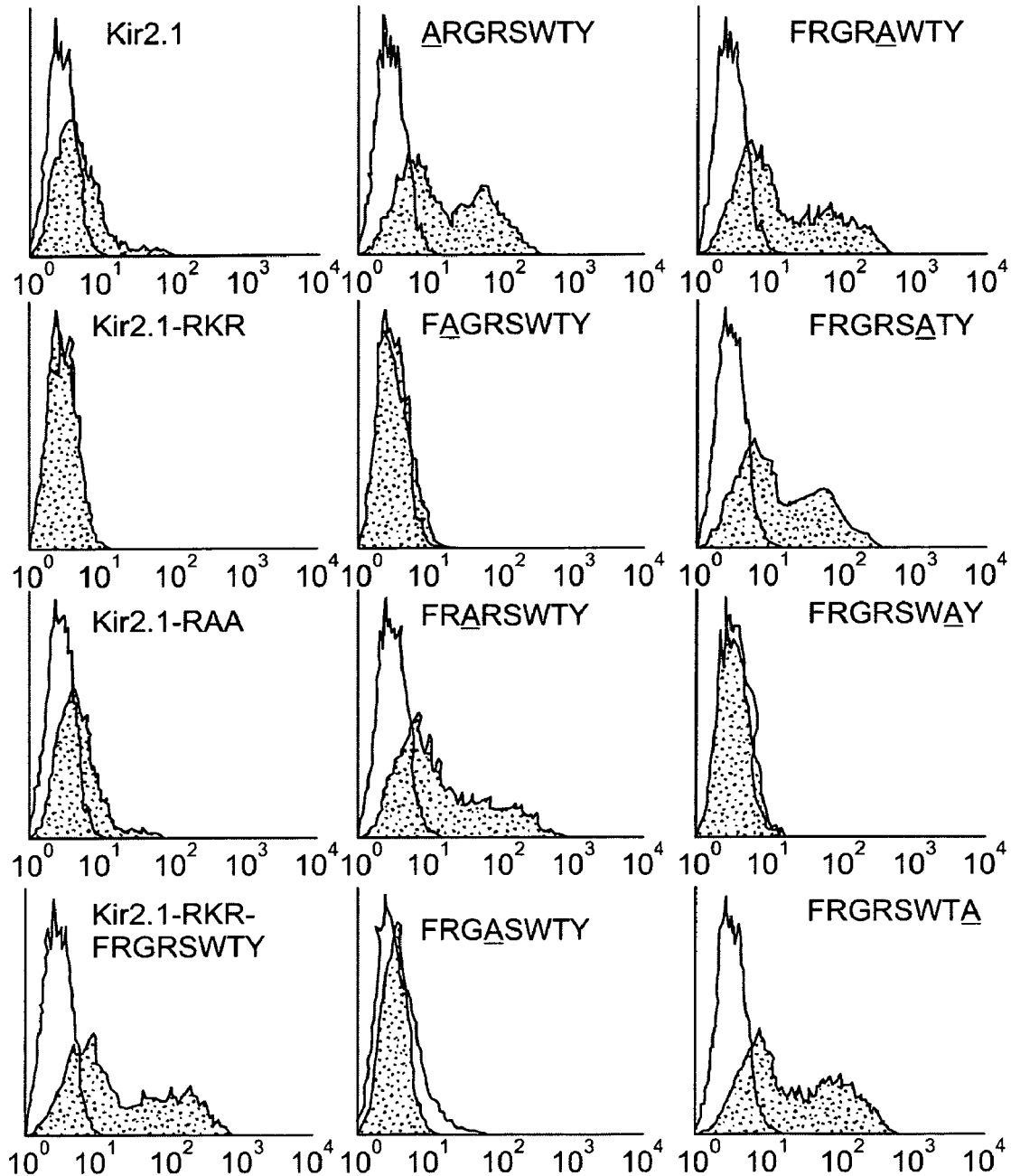

FIG. 3B shows histograms from flow cytometry analyses determining the surface expression of HA-tagged Kir2.1 using anti-HA antibody. The left four panels show control constructs of Kir2.1, Kir2.1-RKR, Kir2.1-RAA and Kir2.1-RKR-RGRSWTY (peptide disclosed as SEQ ID NO: 252) (RKR-FRGRSWTY peptide disclosed as SEQ ID NO: 329). The remaining eight panels (SEQ ID NOS 325, 326, 3, 327, 328, 4, 5, & 330 respectively in order of appearance) display the expression of Ala-substituted mutants as indicated by the underlined positions.

Figure 3C:
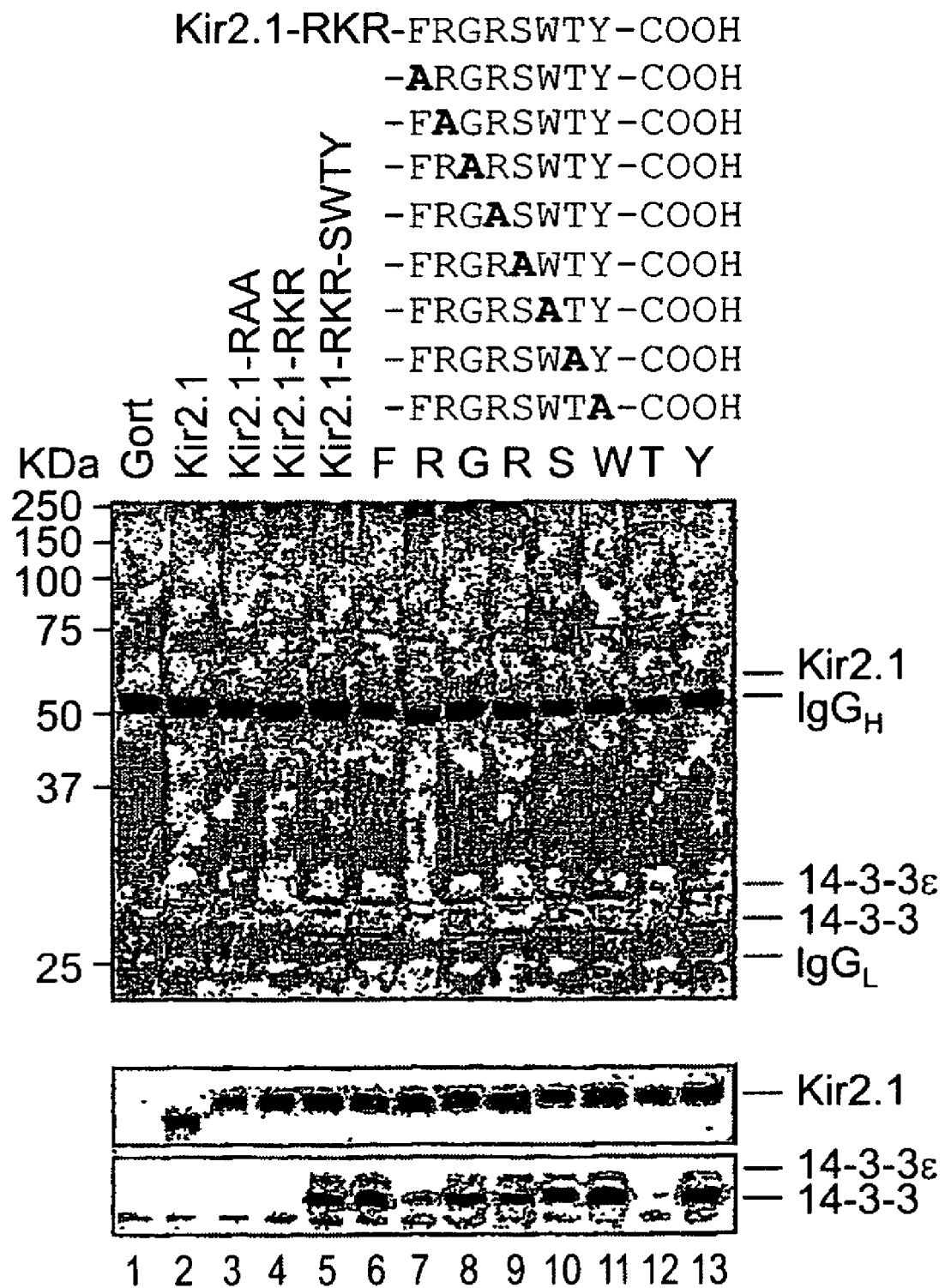

FIG. 3C shows immunoprecipitation with anti-HA antibody. Lanes 1 through 5 correspond to the immunoprecipitates of transfected cell lysates from control vector, Kir2.1, Kir2.1-RAA, Kir2.1-RKR and Kir2.1-RKR-RGRSWTY (peptide disclosed as SEQ ID NO: 252) (RKR-SWTY peptide disclosed as SEQ ID NO: 251). Lanes 6 to 13 are from Ala-substituted mutants. The top panel constitutes an image of the silver staining gel (peptides above disclosed as SEQ ID NOS 2, 325, 3, 328, 5, 326, 327, 4, & 330 respectively in order of appearance). The 14-3-3 proteins were identified by MALDI-TOF and are shown on the right, and molecular weight standards in kDa are shown on the left. The middle panel constitutes an immunoblot of the same material probed with anti-Kir2.1 antibody. The bottom panel is an immunoblot using anti-14-3-3 antibody, which cross-reacts to all seven isoforms.

Figure 4A:
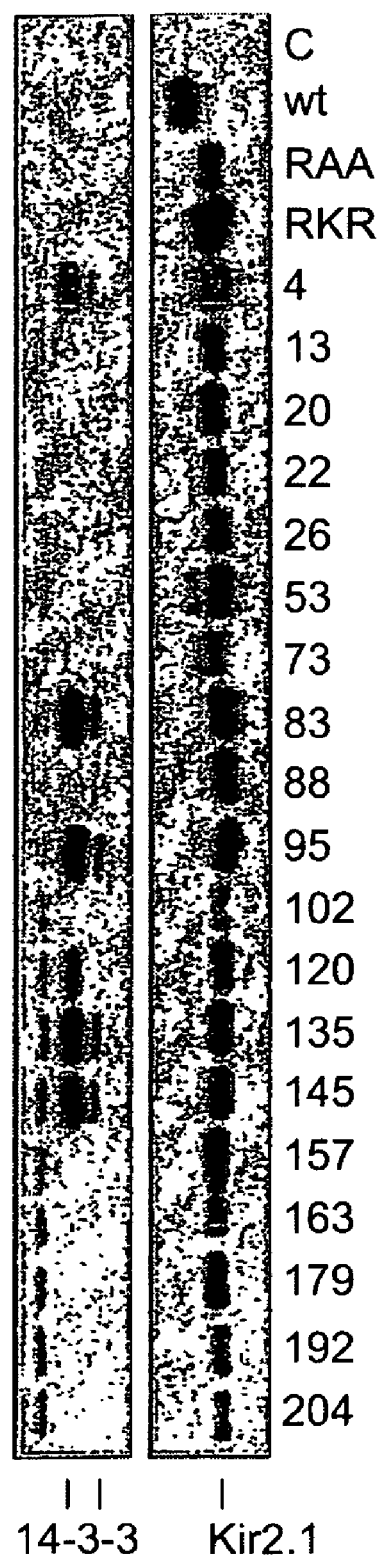

FIG. 4A constitutes immunoblot detection of Kir2.1 and 14-3-3. HEK293 cells were transiently transfected with the indicated clones, and the corresponding lysates were subject to immunoprecipitation using anti-HA antibody. The Kir2.1 was detected by anti-Kir2.1 antibody (upper panel). The same materials were probed with anti-14-3-3 antibody (lower panel).

Figure 4B:
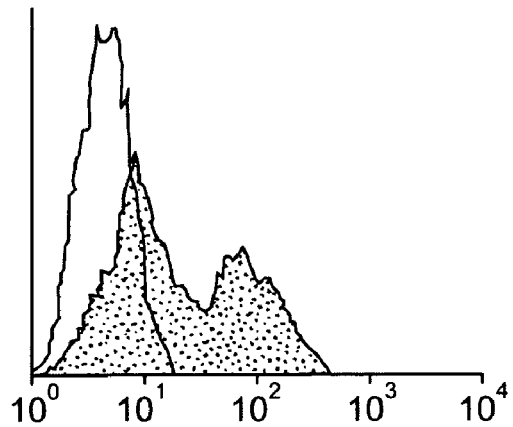
Figure 4B:
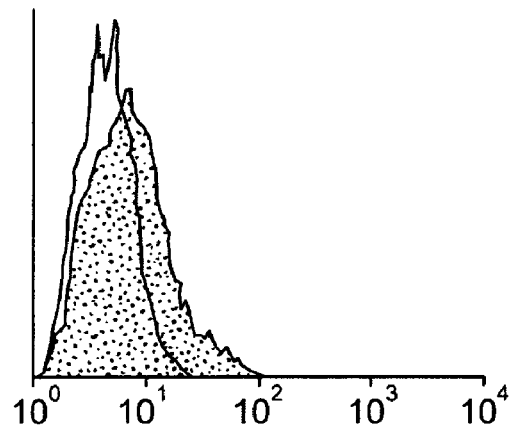
Figure 4B:
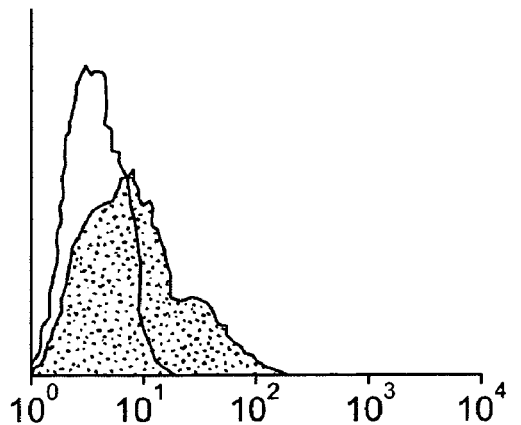
Figure 4B:
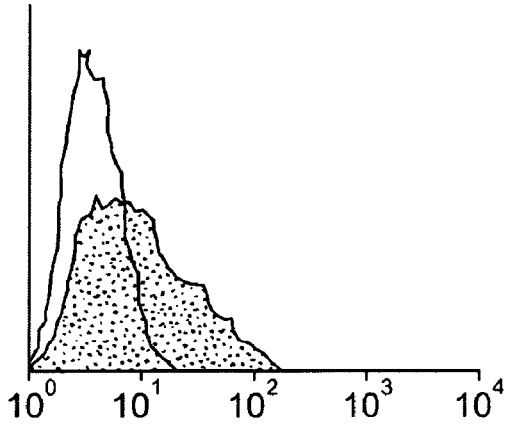
Figure 4B:
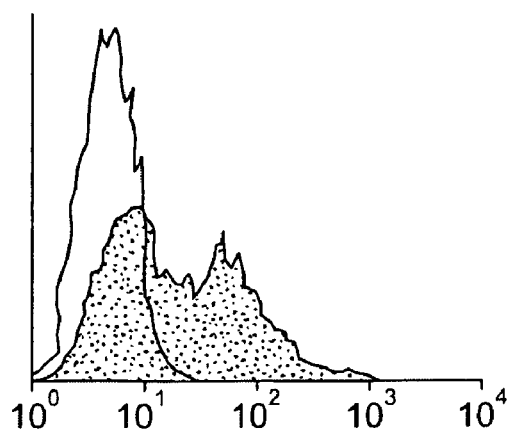
Figure 4B:
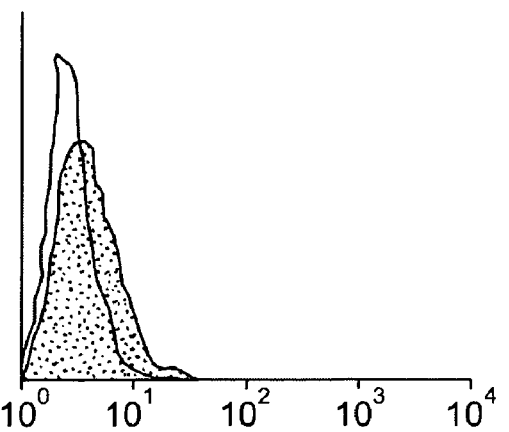

FIG. 4B shows flow cytometry analyses of surface expression of Kir2.1 fusions with SWTY-like motifs (peptides disclosed in the left column are SEQ ID NOS 1, 6, & 332 respectively in order of appearance, peptides disclosed in the right column are SEQ ID NOS 9, 8, & 10 respectively in order of appearance). The filled areas are signals detected by anti-HA, and the unfilled areas represent background. The corresponding clones are as indicated.

Figure 4C:
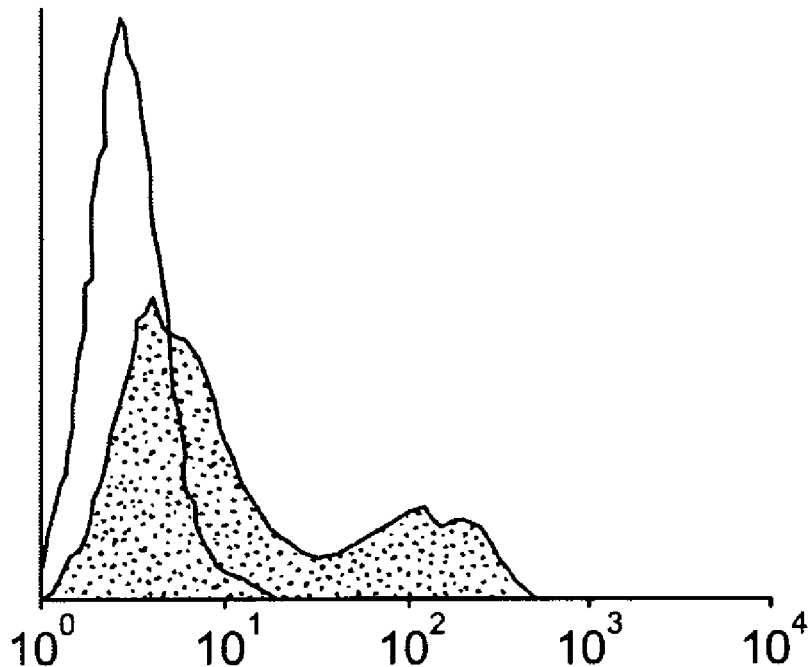
Figure 4C:
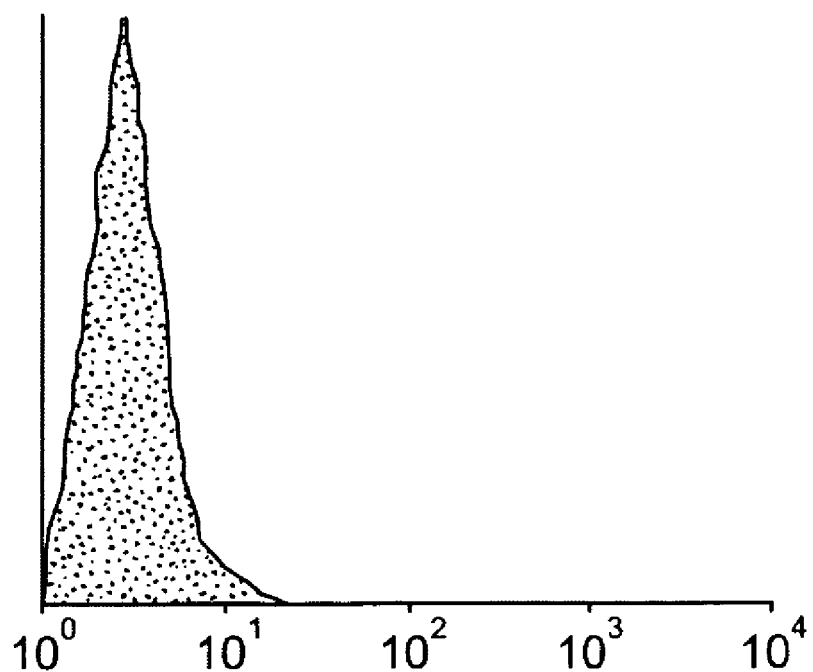

FIG. 4C shows flow cytometry analyses of surface expression of Kir2.1-SWTY (peptide disclosed as SEQ ID NO: 250) and Kir2.1-SWTY-AAA (peptide disclosed as SEQ ID NO: 253). The filled areas are signals detected by anti-HA, and the unfilled areas represent background. The corresponding clones are as indicated (SEQ ID NOS 252 & 331).

Figure 4D:
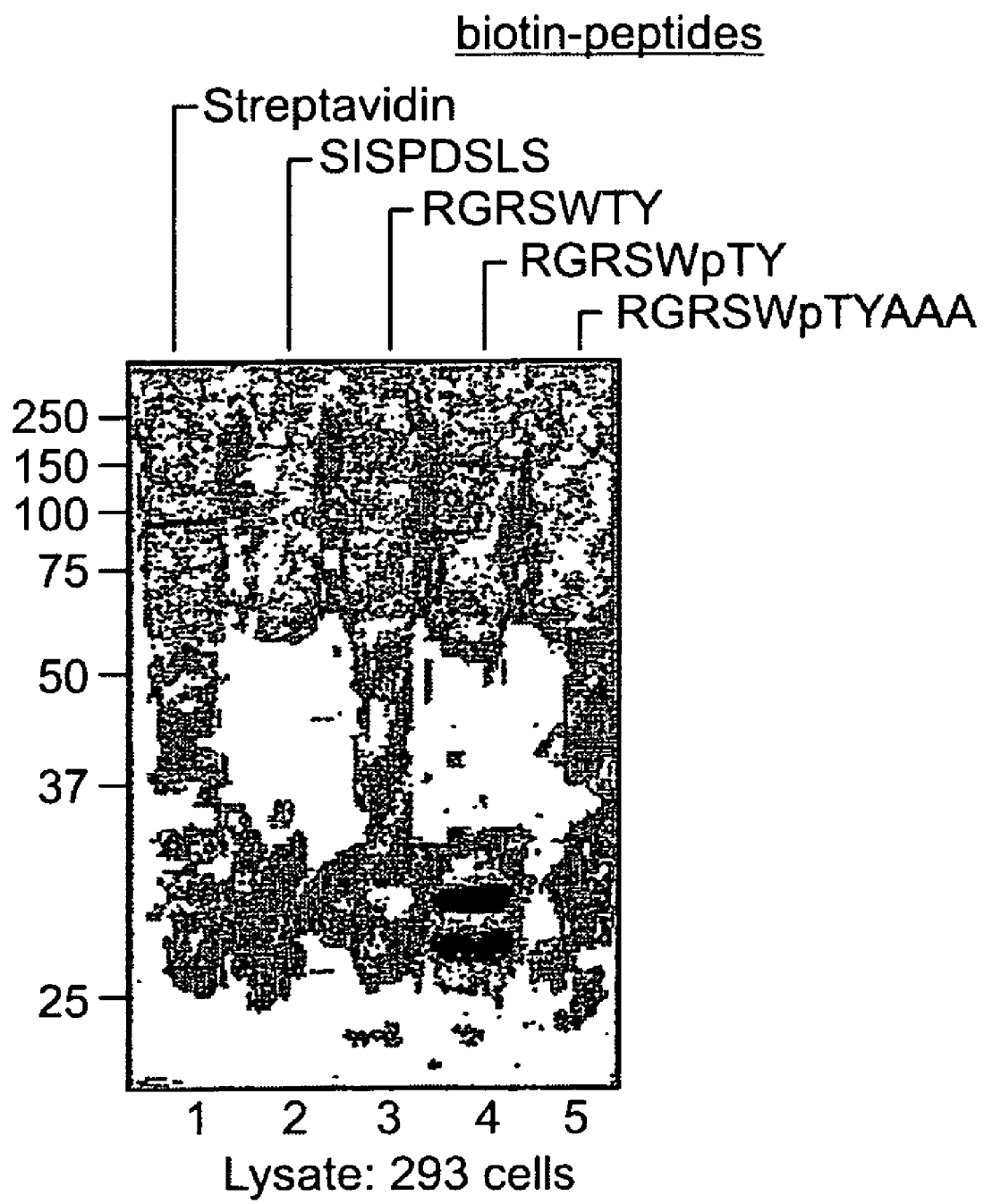

FIG. 4D shows affinity precipitation of 14-3-3 proteins from HEK293 cells, using synthetic peptides corresponding to a control sequence (SISPDSLS) (SEQ ID NO: 254) and three forms of the SWTY sequence (SEQ ID NO: 250) (RGR-SWTY (SEQ ID NO: 1), RGRSWpTY (SEQ ID NO: 255), and RGRSWpTYAAA (SEQ ID NO: 256)). Streptavidin-conjugated beads with bound biotin peptides were used to bind and precipitate interacting proteins. The pull-down materials were visualized by silver stain. The peptide sequences used are shown on the top. Molecular weight standards (kDa) are shown on the left.

Figure 5A:
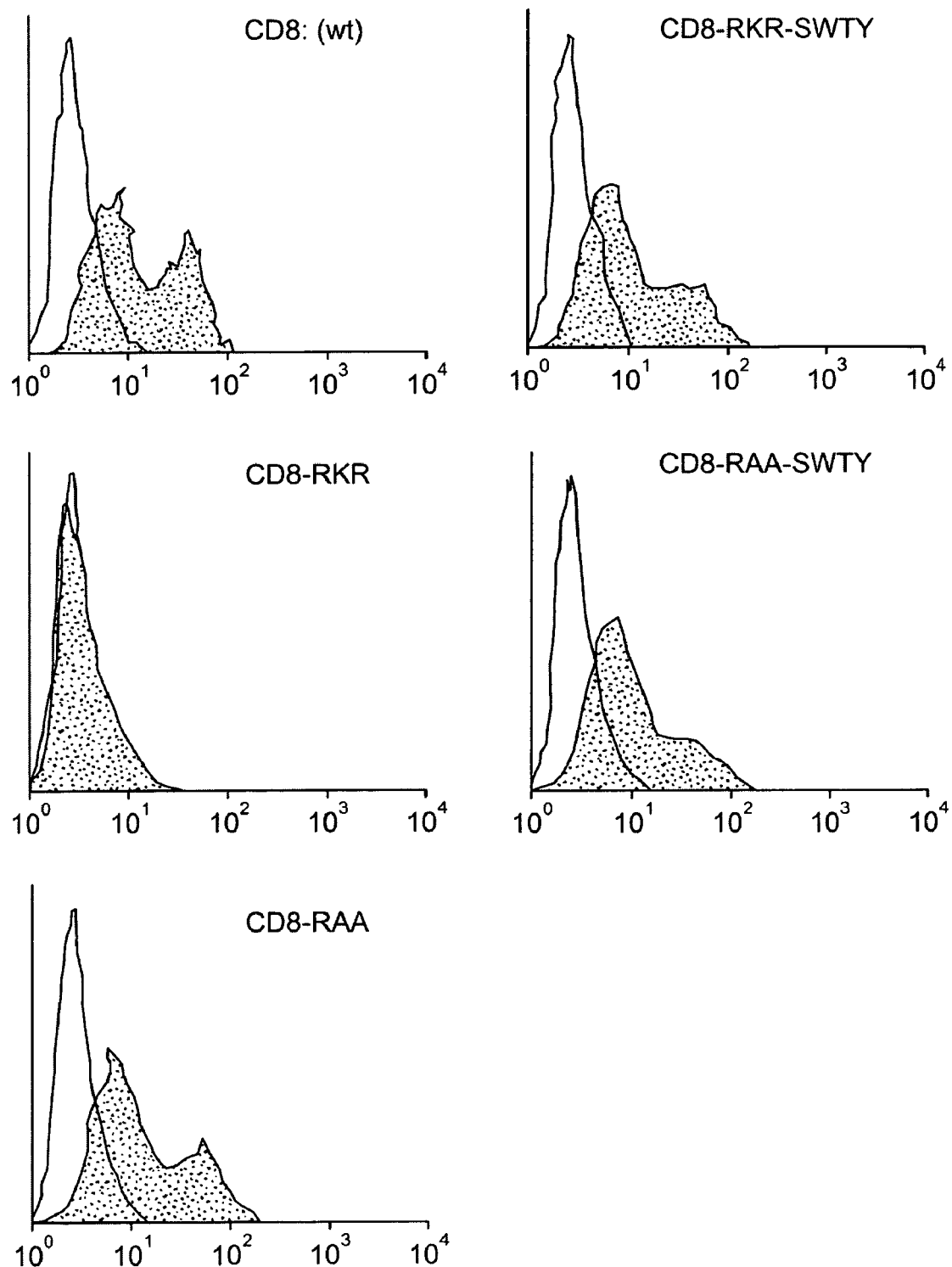

FIG. 5A shows histograms from flow cytometry analyses for surface expression of CD8 proteins in the wild-type form and as part of a fusion with RKR, RAA, RKR-SWTY (SEQ ID NO: 251), or RAA-SWTY (SEQ ID NO: 257). The filled areas represent CD8 signals, and the unfilled areas represent the signals from mock transfected cells.

Figure 5B:
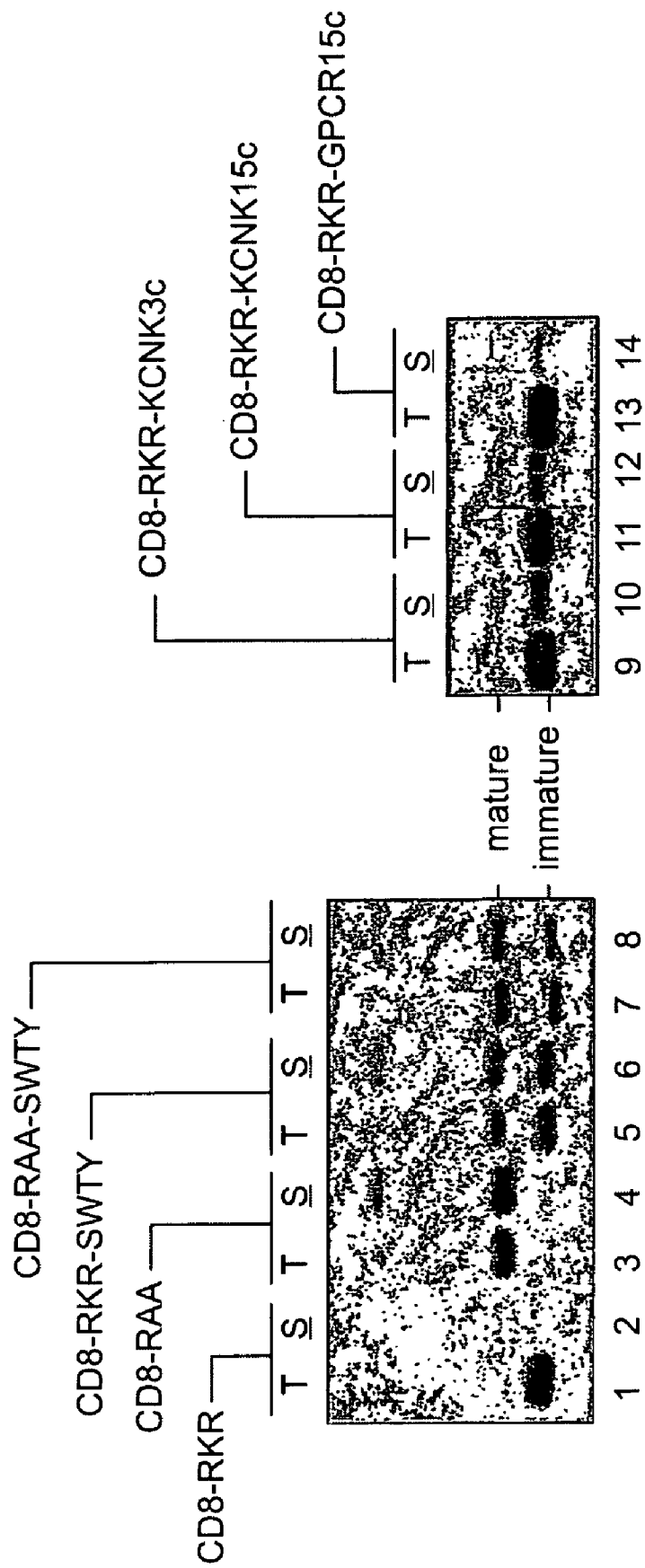

FIG. 5B depicts immunoblot detection of CD8 and CD8 fusion proteins (SEQ ID NOS 251 & 257) in total cell lysate or surface fraction. Total (T) and surface (S) fractions were prepared from HEK293 cells transfected with the indicated clones and blotted with anti-HA antibody. CD8 proteins with different extents of O-linked glycosylation are indicated as mature and immature, respectively. The signals of approximately 50 KDa are IgG heavy chains. Lanes 9 to 14 show total cell lysate vs. surface expression for CD8 with the native C-terminal sequences of KCN15, KCNK3, and GPCR15.

Figure 5C:
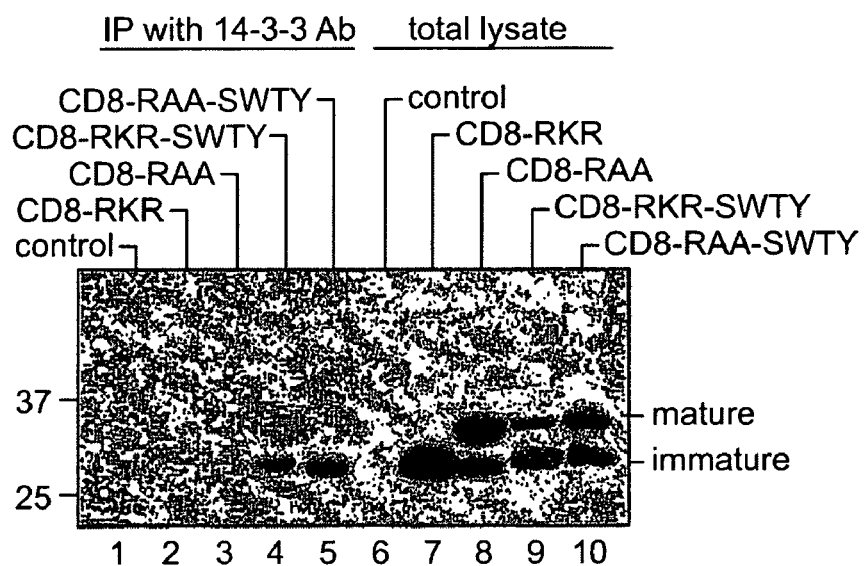

FIG. 5C shows the results of co-immunoprecipitation of CD8 proteins with 14-3-3. Total lysates from cells transfected with various CD8 constructs as indicated were immunoprecipitated by anti-14-3-3 Ab (lanes 1-5) (peptides disclosed as SEQ ID NOS 251 & 257), and the eluates were subsequently blotted with anti-HA Ab. Blots of total lysates are shown in lanes 6-10 (peptides disclosed as SEQ ID NOS 251 & 257). Molecular weight standards (kDa) are shown on the left.

Figure 6A:
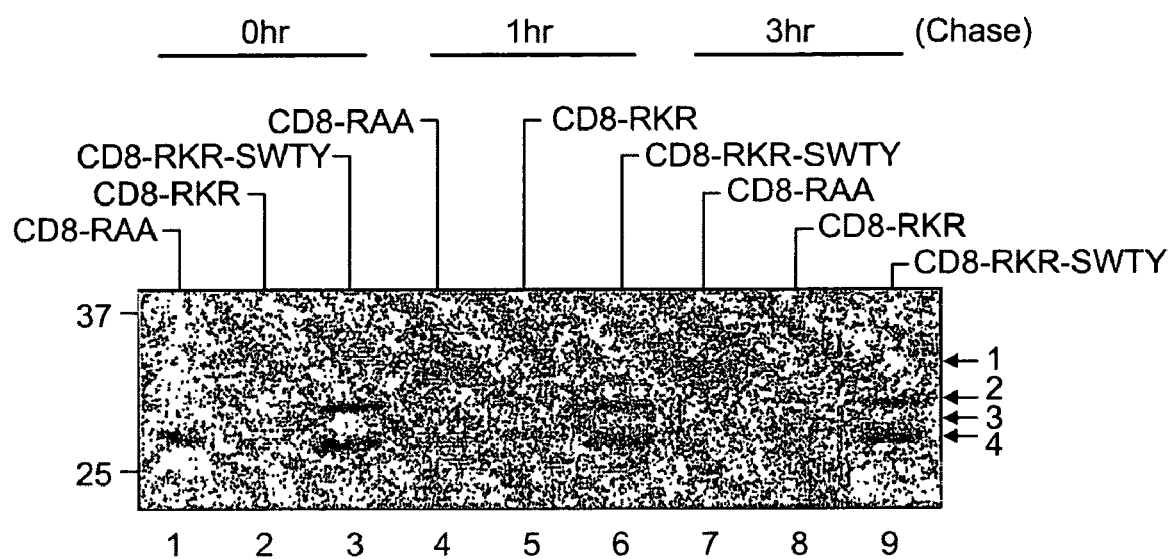

FIG. 6A shows the autoradiography results of pulse-chase analyses performed of CD8 and Kir2.1 proteins with SWTY motif (RKR-SWTY peptide disclosed as SEQ ID NO: 251). The cell lysates were immunoprecipitated with anti-CD8 antibody. Arrows 1 and 3 indicate the mature and immature forms of CD8, respectively, and arrows 2 and 4 indicate the 14-3-3 isoforms. Molecular weight standards (kDa) are shown on the left.

Figure 6B:
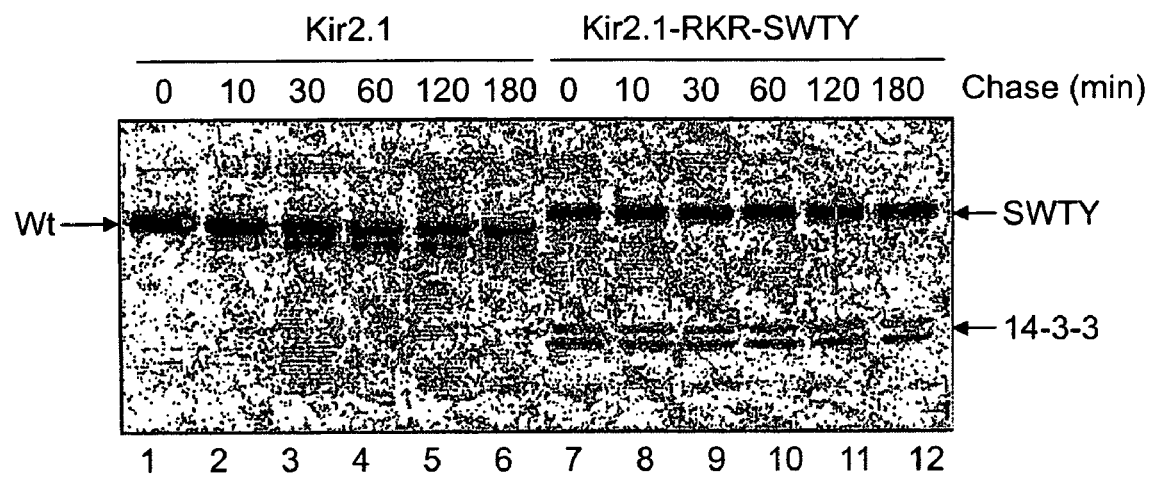

FIG. 6B shows the autoradiography results of pulse-chase analyses performed using cell lines stably expressing wild type Kir2.1 and Kir2.1-RKR-SWTY (peptide disclosed as SEQ ID NO: 251). The cells were pulsed for 10 min at 37° C., chased at 37° C. for the indicated periods, and the cell lysates were immunoprecipitated with anti-HA antibody. The signals between 25 and 37 kDa (the strong upper and lower bands) represent 14-3-3 isoforms that were co-immunoprecipitated with Kir2.1-RKR-SWTY (peptide disclosed as SEQ ID NO: 251).

Figure 6C:
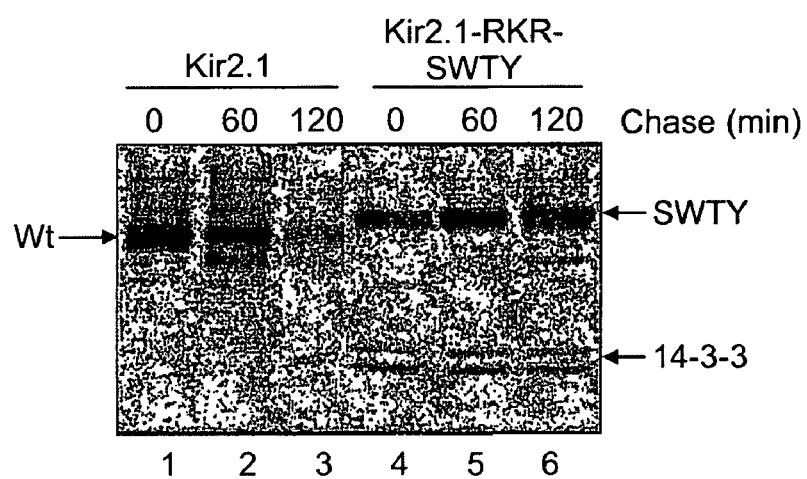

FIG. 6C shows the results of pulse-chase studies of the surface fraction of Kir2.1 and Kir2.1-RKR-SWTY (peptide disclosed as SEQ ID NO: 251) stable cell lines. The stably transfected cells at indicated chase periods after pulse were incubated with anti-HA Ab first, lysed, and the Kir2.1 proteins were precipitated by protein A beads. The wild type (wt) and SWTY-fused Kir2.1 channel peptides (peptide disclosed as SEQ ID NO: 250) are as indicated by arrow.

Figure 6D:
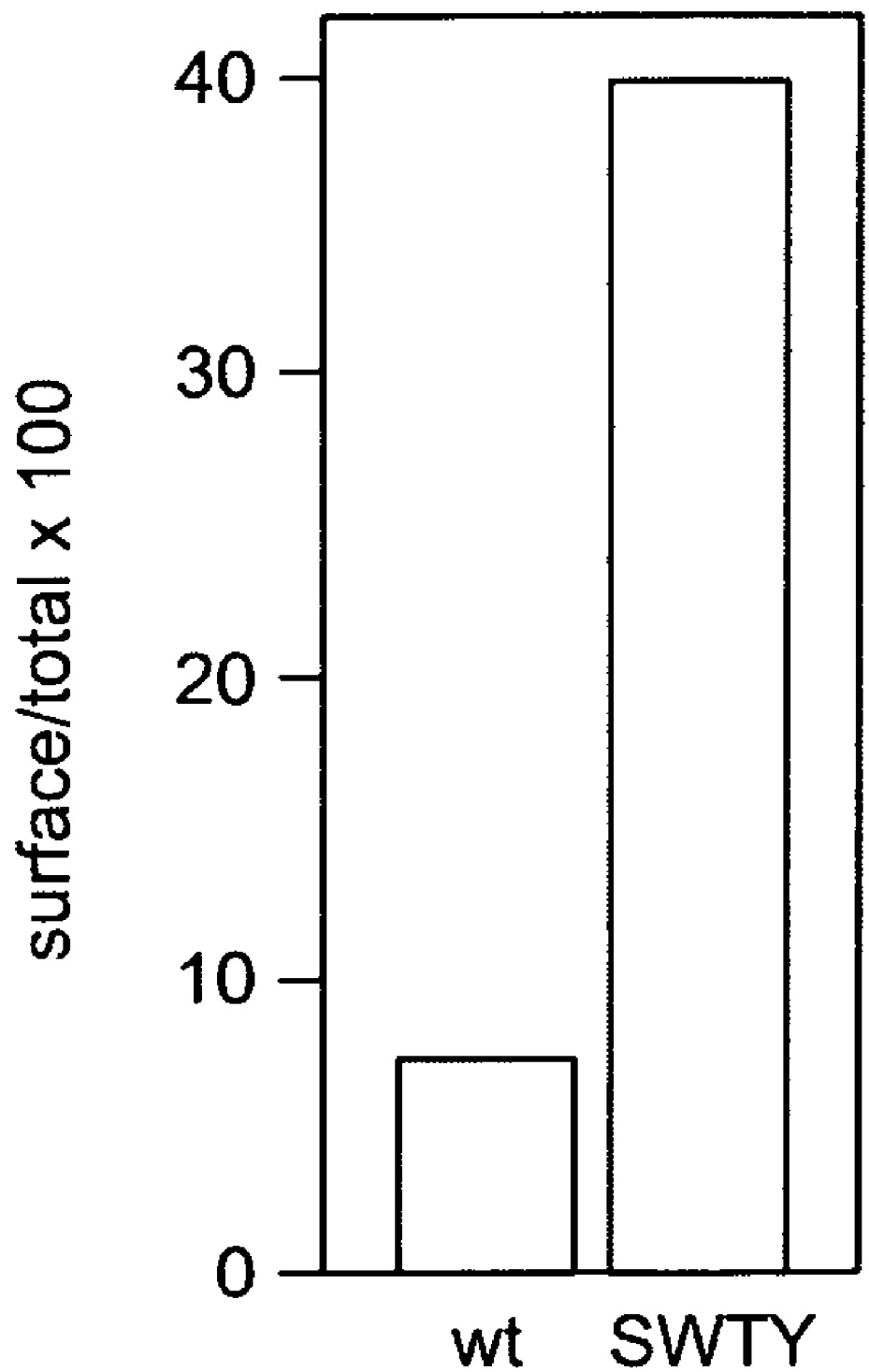

FIG. 6D constitutes a bar graph quantification of radioactively labeled Kir2.1. The ratios of radioactive signals of surface-immunoprecipitated material vs. total immunoprecipitated material are quantified. The ratios for wt and SWTY (SEQ ID NO: 250) at 120 min afterpulse are displayed in histograms.

FIG. 7A summarizes the filtering criteria (for filtering native SWTY-like C-terminal sequences (peptide disclosed as SEQ ID NO: 250), i.e., for similarity to RGRSWTY (SEQ ID NO: 1)) and hits from different species upon sequential applications of filtering criteria. A comprehensive set of all non-redundant proteins of six organisms was screened for C-terminal sequences similar to RGRSWTY (SEQ ID NO: 1). Screening criteria were based on data from flow cytometry and co-immunoprecipitation. The specific criteria used are listed on the left. The number of genes matching each sequentially filtered criteria are listed. Redundant splice variants of one gene are registered as one hit.

Figure 7B:
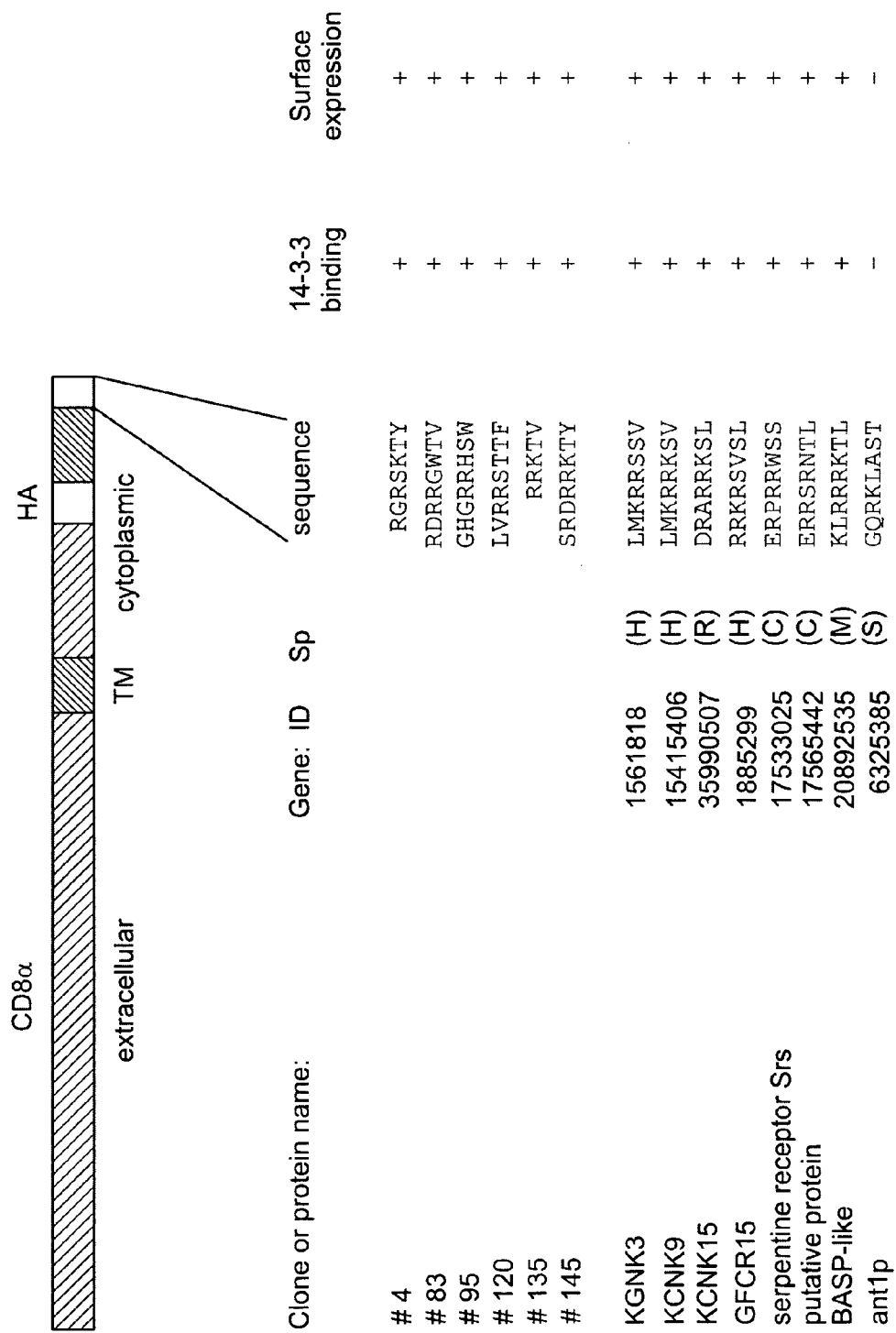

FIG. 7B shows, in the upper panel, a schematic diagram of the CD8 construct which includes the HA epitope, the RKR motif, and the fused SWTY (SEQ ID NO: 250) or SWTY-like sequences (peptide disclosed as SEQ ID NO: 250). Below, the sequences from either random peptide library or from selected genes identified from bioinformatics search (SEQ ID NOS 1, 6, 7, 9, 8, & 10-18 respectively in order of appearance) are aligned according to their C-terminal positions and identified by clone number or protein name, ID, and species. Their ability to bind to 14-3-3 and to override RKR signal were determined by co-immunoprecipitation and flow cytometry analyses. The co-IP and flow cytometry results are summarized as indicated.

Figure 8A:
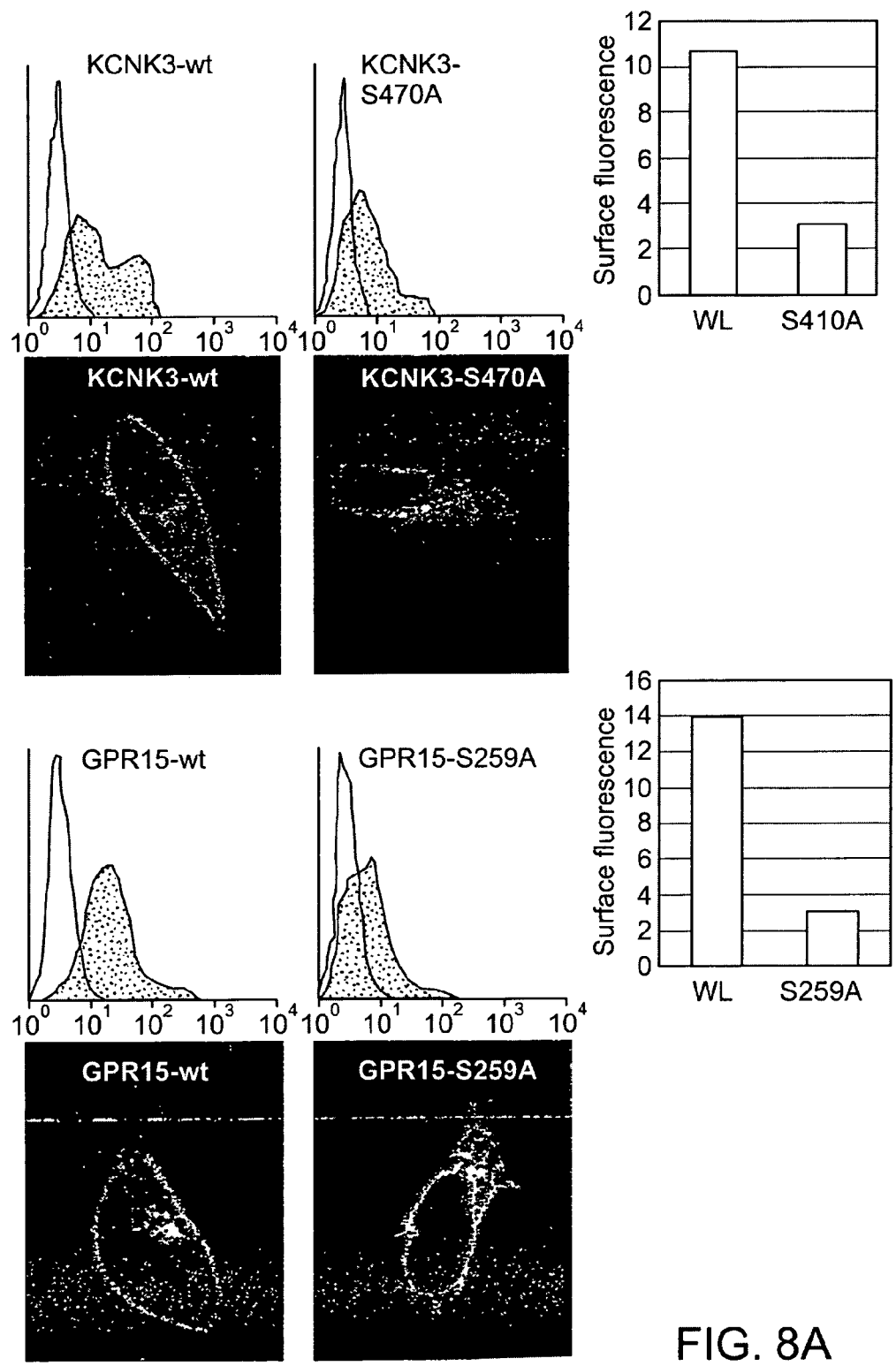

FIG. 8A shows histograms from flow cytometry analyses for surface expression of HA-tagged KCNK3 and GPR15 with and without mutation of serine to alanine at the C-terminal -2 position (upper two panels of each upper and lower set of four pictures). The filled areas represent KCNK3 or GPR15 signals, and the unfilled areas represent signals from mock-transfected cells. The bar graphs to the right of the histograms show the quantitation of surface expression. The mean fluorescence intensity for wild-type and mutant (S410A or S259A) proteins were measured by FCM analyses and subtracted with that of mock-transfected cells. Sublocalization was analyzed by confocal microscopy (lower panels of each upper and lower set of four pictures). The transfected cells were permeabilized and visualized for KCNK3 and GPR15 by anti-HA antibody.

Figure 8B:
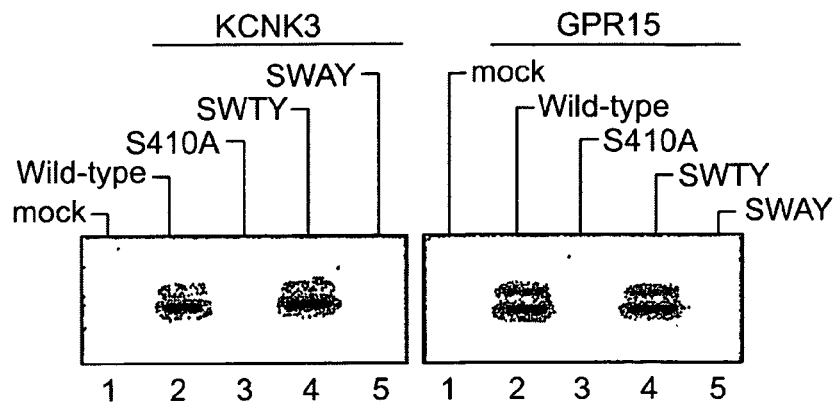

FIG. 8B shows the results of co-immunoprecipitation of 14-3-3 with KCNK3 (peptides disclosed as SEQ ID NOS 250 & 264) and GPR15 (peptides disclosed as SEQ ID NOS 250 & 264). Total lysates from transfected cells as indicated were immunoprecipitated by anti-HA antibody, and the eluates were blotted with anti-14-3-3 antibody.

Figure 8C:
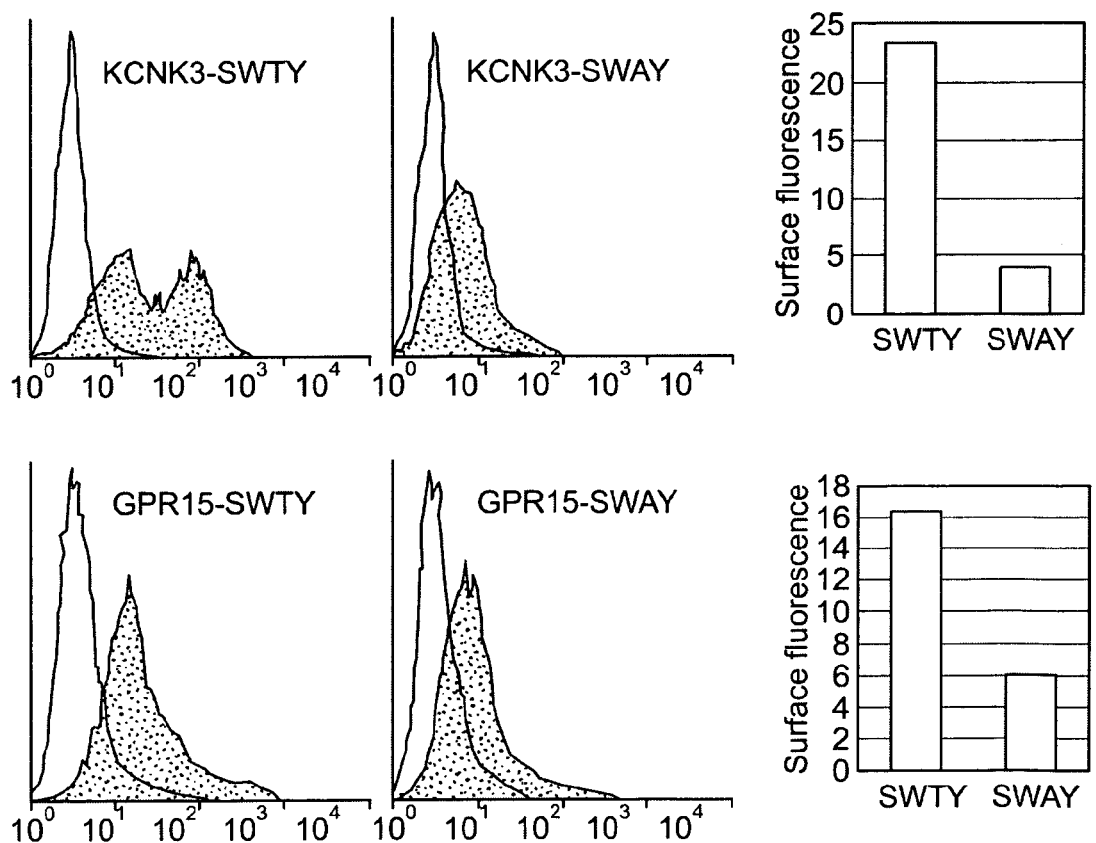

FIG. 8C shows histograms from flow cytometry analyses for surface expression of KCNK3 and GPR15 with their C-terminal sequences (RRSSV (SEQ ID NO: 258) or RRKRSVSL (SEQ ID NO: 14)) replaced with RGRSWTY (SEQ ID NO: 1) or RGRSWAY (SEQ ID NO: 259). (SWTY disclosed as SEQ ID NO: 250, SWAY disclosed as SEQ ID NO: 264) Also shown is bar graph quantitation of the surface fluorescence measured for each (peptides disclosed as SEQ ID NOS 250 & 264).

Figure 9:
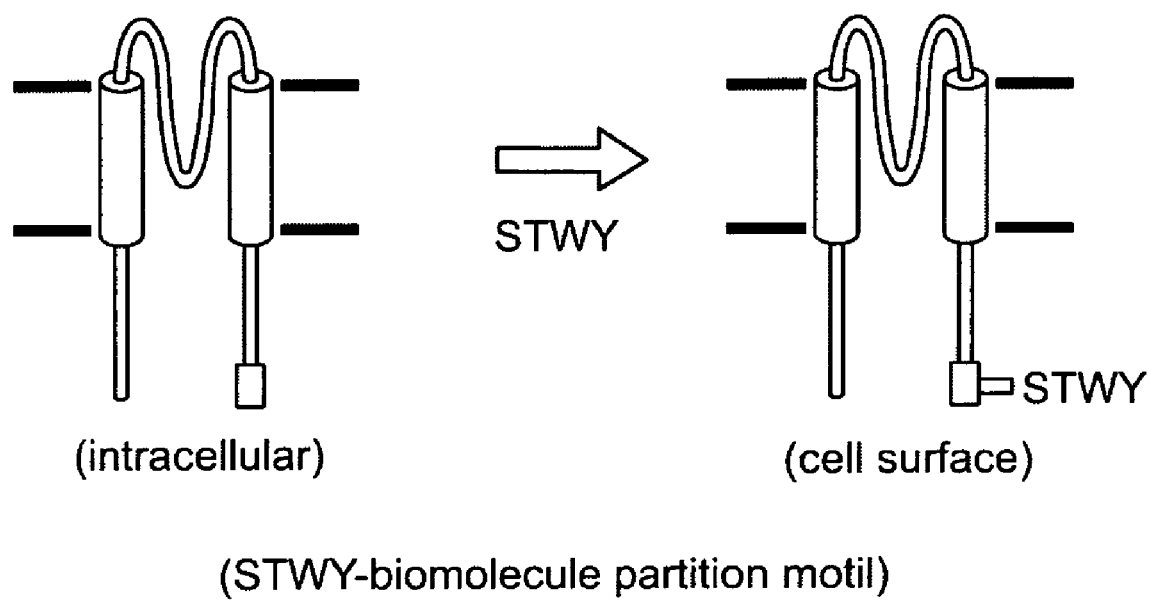

FIG. 9 shows a schematic diagram of protein re-partition induced by an interaction with a modified biomolecule partition motif. A transmembrane protein is first shown to be localized in an intracellular compartment. Upon interaction with a tag that associates with a SWTY motif (SEQ ID NO: 250), the complex repartitions, resulting in elevated expression on the cell surface.

DETAILED DESCRIPTION OF THE INVENTION

I. Definitions

A "biomolecule partition motif" is an amino acid sequence motif comprising between about 5 to about 20 contiguous amino acids that bind to 14-3-3 proteins and are located in the cytoplasmic portion of a membrane targeted polypeptide. A membrane targeted polypeptide is a polypeptide delivered to or through a membrane.

A "SWTY motif" (SEQ ID NO: 250) is one kind of biomolecule partition motif. A SWTY motif (SEQ ID NO: 250) is an amino acid sequence motif comprising between about 5 to about 10 contiguous amino acids having either a serine or threonine amino acid residue at the -2 position relative to the carboxy terminus and having amino acid residues that can be phosphorylated in positions -3 to -10, preferably at position -2, relative to the carboxy terminus. In specific embodiments, the SWTY motif (SEQ ID NO: 250) contains at least 2 amino acid residues of the sequence RGRSWTY (SEQ ID NO: 1) in positions -7, -6, -5, X, -3, -2 and -1, respectively, relative to the carboxy terminus (e.g., R (-7), G (-6), R (-5), S (-4), W (-3), T (-2) Y (-1)-COOH). In other specific embodiments, the SWTY motif contains at least 2 amino acid residues of the sequence FRGRSWTY (SEQ ID NO: 2) in positions -8 through -1, respectively, relative to the carboxy terminus and optionally having an alanine substitution at any single position (e.g., F (-8), A (-7), G (-6), R (-5), S (-4), W (-3), T (-2) Y (-1)-COOH; F (-8), R (-7), R (-6), R (-5), S (-4), W (-3), A (-2) Y (-1)-COOH or F (-8), R (-7), G (-6), A (-5), S (-4), W(-3), T (-2) Y (-1)-COOH).

An "endoplasmic reticulum" is a membrane bounded compartment in the cytoplasm of eukaryotic cells, where lipids are synthesized and membrane-bound proteins are made.

A "cell surface polypeptide" is any polypeptide in contact with the extracellular membrane in which some portion of the polypeptide, or modification attached to the polypeptide (e.g., a lipid), is externally located (i.e., external relative to the extracellular membrane). The portion of the cell surface polypeptide that is externally located is said to be "extracellular." Contact with the extracellular membrane can be direct or indirect (e.g., by protein-protein interaction, lipid linkage or otherwise). Cell surface polypeptides include, for example, transmembrane proteins which have an intracellular domain, a transmembrane domain and an extracellular domain. Cell surface polypeptides of the invention can associate, or form complexes, with other polypeptides that may or may not also have a biomolecule partition motif.

An "extracellular membrane" is a double layer of lipid molecules (i.e., a lipid bilayer) and associated proteins that encloses all cells.

The term "native" as used herein refers to a naturally occurring polypeptide, or amino acid sequence thereof, that has not been manipulated by recombinant or affinity based techniques. Accordingly, native polypeptides and amino acid sequences of the invention have not been altered to include additional sequences, such as sequences encoding a SWTY motif (SEQ ID NO: 250).

A "non-native biomolecule partition motif" refers to a biomolecule partition motif that has been added directly or indirectly to a naturally occurring polypeptide by recombinant techniques.

A "non-native SWTY motif" (SEQ ID NO: 250) refers to a SWTY motif (SEQ ID NO: 250) that has been added directly or indirectly to a naturally occurring polypeptide by recombinant techniques.

As used here in, the term "recombinant" is used to describe nucleic acid sequences (or the amino acid sequences encoded thereby) that have been joined to other nucleic acid sequences by genetic modification (e.g., enzymatic or chemical processes).

A "fusion polypeptide" as used herein is a polypeptide joined to another polypeptide or amino acid sequence (e.g., biomolecule partition motif) by peptide-bond formation or affinity-based techniques.

A "coding region" refers to a region of a gene that contains nucleic acid sequences that are transcribed into messenger RNA (mRNA). The term "encode" describes a nucleic acid sequence that is transcribed into messenger RNA (mRNA) and ultimately, yields an amino acid sequence that forms a polypeptide.

A "post-translational modification" is any enzymatic modification of a polypeptide occurring after translation has commenced. Post-translational modifications include but are not limited to glycosylation, amino acid modification or substitution, bond breakage or formation (e.g., sulfide bonding) and linkage formation (e.g., farnesylation, acetylation).

An "O-linked glycosylation pattern" is generated by linkage of sugars to the OH group of selected serine or threonine side chains in the golgi apparatus.

An "immunogen" is a molecule that provokes an immune response.

An "immunogenic determinant" is a specific region of an immunogenic molecule that binds to an antibody or a T cell receptor.

As used herein, a "test agent" is any experimental compound that binds to a cell surface polypeptide.

The term "obtaining" as in "obtaining the diagnostic agent" is intended to include purchasing, synthesizing or otherwise acquiring the diagnostic agent (or indicated substance or material).

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Additional definitions are provided in context throughout the disclosure.

II. Methods and Compositions of the Invention

The present invention is predicated on the discovery of biomolecule partition motifs, which have the ability to mediate delivery of polypeptides into or through a membrane, such as an extracellular membrane, nuclear membrane or organelle membrane. Benefits associated with biomolecule partition motifs of the invention are applicable to a diverse range of cell-based technologies and therapeutics.

Providing polypeptides to an extracellular membrane, for example, can result in increased levels of cell surface expression. Increasing cell surface expression can result in an increased yield of the polypeptide upon isolation from a cell. Increasing cell surface expression can also provide increased access to the polypeptides. Such improvements are useful in biomedical applications involving drug screening, antibody generation and vaccine production.

Biomolecule partition motifs of the invention can also be useful in the development of therapeutic biologics. Addition of the motif can alter post-translational modification of a polypeptide in ways that enhance its overall clinical effect. For example, biomolecule partition motifs can reduce or otherwise alter glycosylation to reduce adverse inflammatory reactions.

Biomolecule partition motifs of the invention are also useful for providing mutated or defective polypeptides that would otherwise be retained in the endoplasmic reticulum to a membrane, thereby restoring function. In clinical applications, mutated polypeptides causing genetic defects associated with targeting defects can be properly targeted by the addition of a biomolecule partition motif, thereby restoring function in vivo and alleviating symptoms associated with such disorders.

A biomolecule partition motif is an amino acid sequence motif comprising between about 5 to about 20 contiguous amino acids that bind to 14-3-3 proteins and are located in the cytoplasmic portion of a membrane targeted polypeptide. The 14-3-3 family of proteins contains monomers of 9 antiparellel alpha helices organized as two structural domains (for detailed reviews, see H. Fu et al. (2000) Annu. Rev. Pharmacol. Toxicol. 40:617-47 and Yaffe, M. B., (2002) FEBS Letters 513 (2002) 53-57, the contents of which are incorporated herein by reference). When in dimer form, a large, negatively charged channel 35 angstroms broad, 35 angstroms wide, and 20 angstroms deep is created. 14-3-3 proteins act by binding to specific target proteins at optionally phosphorylated binding sites. In specific embodiments, a biomolecule partition motif can override an RKR signal. An RKR signal is an amino acid sequence that causes a polypeptide to be retained in the endoplasmic reticulum (Shikano and Li, 2003). An RKR signal is one of several endoplasmic reticulum localization signals known in the art.

Biomolecule partition motifs of the invention include but are not limited to RGRSWTY (SEQ ID NO: 1) FRGRSWTY (SEQ ID NO: 2) FAGRSWTY (SEQ ID NO: 3) FRGRSWAY (SEQ ID NO: 4) FRGASWTY (SEQ ID NO: 5) RLRRGWTV (SEQ ID NO: 6) GHGRRHSW (SEQ ID NO: 7) RRKTV (SEQ ID NO: 8) LVRRSITF (SEQ ID NO: 9) SRDRRKTY (SEQ ID NO: 10) LMKRRSSV (SEQ ID NO: 11) LMKRRKSV (SEQ ID NO: 12) LRARRKSI (SEQ ID NO: 13) RRKRSVSL (SEQ ID NO: 14) ERHRRWSS (SEQ ID NO: 15) EHRSRNTL (SEQ ID NO: 16) KLRRRKTL (SEQ ID NO: 17) GQRKLAST (SEQ ID NO: 18) QRSIWGKKSQ (SEQ ID NO: 19) FLGKKKTKTD (SEQ ID NO: 20) KANIPKAKSA (SEQ ID NO: 21) IKKNDLKKSN (SEQ ID NO: 22) NIDALLKKTE (SEQ ID NO: 23) NIDALLKKTE (SEQ ID NO: 24) KKNKKRKFTK (SEQ ID NO: 25) LPWKRKKTTI (SEQ ID NO: 26) KVVEKAKYSL (SEQ ID NO: 27) RRLQPAKSTF (SEQ ID NO: 28) RRLQPAKSTF (SEQ ID NO: 29) IKKLWCKTSA (SEQ ID NO: 30) IKKLWCKTSA (SEQ ID NO: 31) PYVCKCKLTN (SEQ ID NO: 32) TYVCKCKFTN (SEQ ID NO: 33) IKLLNEKKTS (SEQ ID NO: 34) GRRRGGKATT (SEQ ID NO: 35) KKILGGKCSQ (SEQ ID NO: 36) ETLCRKKLSG (SEQ ID NO: 37) FGKGTKKTSH (SEQ ID NO: 38) FKKMVKKSTL (SEQ ID NO: 39) IKKCTKDTSK (SEQ ID NO:

40) IKKCTKDTSK (SEQ ID NO: 41) IKKCTKDTSK (SEQ ID NO: 42) IKKCTKDTSK (SEQ ID NO: 43) IKVLIKKISL (SEQ ID NO: 44) IKVLIKKISL (SEQ ID NO: 45) KKLWSKTLTK (SEQ ID NO: 46) KKLWSKTLTK (SEQ ID NO: 47) RILYKKKISL (SEQ ID NO: 48) RMIKRKILSQ (SEQ ID NO: 49) RVICTKKISL (SEQ ID NO: 50) RVICTKKISL (SEQ ID NO: 51) RVLCKKKITM (SEQ ID NO: 52) RVLCKKNISL (SEQ ID NO: 53) RVLCKKQISL (SEQ ID NO: 54) RVLFKKKISL (SEQ ID NO: 55) RVLIKKKISL (SEQ ID NO: 56) RVLIKKKISL (SEQ ID NO: 57) RVLYKKKISL (SEQ ID NO: 58) RVLYKKKISL (SEQ ID NO: 59) TLLCRKKSSL (SEQ ID NO: 60) TLLCRKKSSL (SEQ ID NO: 61) VKKTLKRITS (SEQ ID NO: 62) VKKTLKRITS (SEQ ID NO: 63) VKKTLKRITS (SEQ ID NO: 64) VKKTLKRITS (SEQ ID NO: 65) VKKTMKRITS (SEQ ID NO: 66) VKKTMKRITS (SEQ ID NO: 67) VMAMVKRKSS (SEQ ID NO: 68) SAKKMLKISV (SEQ ID NO: 69) SAKKMLKISV (SEQ ID NO: 70) SLKKMLKITI (SEQ ID NO: 71) SLKKMLKITI (SEQ ID NO: 72) KKSLRNRISI (SEQ ID NO: 73) KKSLRNRISI (SEQ ID NO: 74) RNRPWPKDSY (SEQ ID NO: 75) DKNLRQRNTN (SEQ ID NO: 76) LKRSRQRFSS (SEQ ID NO: 77) ACERKRDITY (SEQ ID NO: 78) AVQSKRRKSK (SEQ ID NO: 79) DISRRRKLTK (SEQ ID NO: 80) DISRRRKLTK (SEQ ID NO: 81) DRLRARRKSI (SEQ ID NO: 82) EFSRGRKLTK (SEQ ID NO: 83) ERRLQRQQTT (SEQ ID NO: 84) HILRRRLFSQ (SEQ ID NO: 85) HRLHIRRKSI (SEQ ID NO: 86) KGALRRIMSR (SEQ ID NO: 87) KGALRRIMSR (SEQ ID NO: 88) KGALRRITTK (SEQ ID NO: 89) KGALRRITTK (SEQ ID NO: 90) KKLICRVASL (SEQ ID NO: 91) LLFHRRILSS (SEQ ID NO: 92) LLSHRRILSS (SEQ ID NO: 93) LLSHRRILSS (SEQ ID NO: 94) MKKLWRKCSS (SEQ ID NO: 95) MKKLWRKCSS (SEQ ID NO: 96) NIFSRRLCSQ (SEQ ID NO: 97) NILSRRLCSQ (SEQ ID NO: 98) NILSRRLCSQ (SEQ ID NO: 99) NILSRRLCSQ (SEQ ID NO: 100) NTLSRRLCSH (SEQ ID NO: 101) QDYTRRCGTT (SEQ ID NO: 102) RGLMKRRSSV (SEQ ID NO: 103) VKLIRRKISS (SEQ ID NO: 104) VKRRKRSVSL (SEQ ID NO: 105) VKRTMRRITM (SEQ ID NO: 106) VKRTMRRITM (SEQ ID NO: 107) GRRGGSRLTE (SEQ ID NO: 108) HRWRKSRRTI (SEQ ID NO: 109) RYKKSTRVTF (SEQ ID NO: 110) SKVQKTKNTT (SEQ ID NO: 111) SKVQKTKNTT (SEQ ID NO: 112) KFCKGKTPSC (SEQ ID NO: 113) STPGRSRNSL (SEQ ID NO: 114) FLVFRDRVSL (SEQ ID NO: 115) KFIGRERRTS (SEQ ID NO: 116) NMVNKHKFSH (SEQ ID NO: 117) DLVRRKLASK (SEQ ID NO: 118) DLVRRKLASK (SEQ ID NO: 119) GVLGKKKISL (SEQ ID NO: 120) HRALQKKRSV (SEQ ID NO: 121) KKLWCKTLTT (SEQ ID NO: 122) KRQLGKKMSC (SEQ ID NO: 123) KRQLGKKMSC (SEQ ID NO: 124) KVIAKKFLTK (SEQ ID NO: 125) MKKSWKRITS (SEQ ID NO: 126) MKKSWKRITS (SEQ ID NO: 127) NALTIKKESE (SEQ ID NO: 128) NLFSCKKGSI (SEQ ID NO: 129) NSTGKKILSR (SEQ ID NO: 130) PQKSKKDRTQ (SEQ ID NO: 131) RIIGSKKISL (SEQ ID NO: 132) RRSLLKERSM (SEQ ID NO: 133) RRSLLKERSM (SEQ ID NO: 134) RRVLWKQRSL (SEQ ID NO: 135) RVICSKKISL (SEQ ID NO: 136) RVICSKKISL (SEQ ID NO: 137) RVIFSKKISL (SEQ ID NO: 138) RVISSKKISL (SEQ ID NO: 139) RVLCKKEISL (SEQ ID NO: 140) SPRNRKEKSS (SEQ ID NO: 141) SSRTKKLKSP (SEQ ID NO: 142) SSRTKKLKSP (SEQ ID NO: 143) SSTGKKILSR (SEQ ID NO: 144) SSTGKKILSR (SEQ ID NO: 145) SSTGKKILSR (SEQ ID NO: 146) VKKTIKRITS (SEQ ID NO: 147) VKKTWKRITS (SEQ ID NO: 148) VKKTWKRLTC (SEQ ID NO: 149) VKKTWKRLTC (SEQ ID NO: 150) VRVLIKKISL (SEQ ID NO: 151) NFSSRLRITH (SEQ ID NO: 152) NFSSRLRITH (SEQ ID NO: 153) RNRPWPKDSY (SEQ ID NO: 154) DKNLRQRNTN (SEQ ID NO: 155) AAKLRRRKTL (SEQ ID NO: 156) AVQSKRRKSK (SEQ ID NO: 157) DRPRARRKSI (SEQ ID NO: 158) ERRLQRQRTT (SEQ ID NO: 159) HRLHLRRKSI (SEQ ID NO: 160) IRRRKRSVSL (SEQ ID NO: 161) IRRRKRSVSL (SEQ ID NO: 162) KKKLFRFDTQ (SEQ ID NO: 163) KTLNRRIFSS (SEQ ID NO: 164) KTLSRRLCSH (SEQ ID NO: 165) LLCHRRKFSP (SEQ ID NO: 166) NVLSRRLCSQ (SEQ ID NO: 167) QDYTRRCGTT (SEQ ID NO: 168) RGLMKRRSSV (SEQ ID NO: 169) VCEKRRNITH (SEQ ID NO: 170) VKLVRRKISS (SEQ ID NO: 171) DIREKSKCSG (SEQ ID NO: 172) HRWRKSRRTI (SEQ ID NO: 173) KKDKDVRVTW (SEQ ID NO: 174) RRRADVRITG (SEQ ID NO: 175) KRRCLCKLSS (SEQ ID NO: 176) EEKKDERKTD (SEQ ID NO: 177) KGKSGERVTS (SEQ ID NO: 178) FKKLIGKKSQ (SEQ ID NO: 179) KKMTRGRQSS (SEQ ID NO: 180) KVLWRGRDSG (SEQ ID NO: 181) ILLKKHKSSH (SEQ ID NO: 182) CPPKRKEKSS (SEQ ID NO: 183) ERRLQKQQTS (SEQ ID NO: 184) FGKGAKKTSH (SEQ ID NO: 185) IRRYQKKATA (SEQ ID NO: 186) KKYGLKPPTL (SEQ ID NO: 187) KRMLEKKRTS (SEQ ID NO: 188) KRMLEKKRTS (SEQ ID NO: 189) LIENLKKASQ (SEQ ID NO: 190) SPRNKKEKSS (SEQ ID NO: 191) SVLTIKKESE (SEQ ID NO: 192) YRALQKKRTM (SEQ ID NO: 193) YSICEKKFSM (SEQ ID NO: 194) YSICEKKFSM (SEQ ID NO: 195) YSICEKKFSM (SEQ ID NO: 196) RNRPWPKDSY (SEQ ID NO: 197) DKNLRQRNTN (SEQ ID NO: 198) DKNLRQRNTN (SEQ ID NO: 199) HLVKRQRPSP (SEQ ID NO: 200) ARRRKRSVSL (SEQ ID NO: 201) AVQSKRRKSK (SEQ ID NO: 202) HLLNRRFFSK (SEQ ID NO: 203) HLPNRRFFSK (SEQ ID NO: 204) LQVRQRLGSL (SEQ ID NO: 205) QDYTRRCGST (SEQ ID NO: 206) QRLMKRRKSV (SEQ ID NO: 207) RGLMKRRSSV (SEQ ID NO: 208) RVMQRRQDSR (SEQ ID NO: 209) RVMQRRQDSR (SEQ ID NO: 210) RVMQRRQDSR (SEQ ID NO: 211) SRRSSRCGTP (SEQ ID NO: 212) TLPRKRMSSI (SEQ ID NO: 213) KVWGRSRASR (SEQ ID NO: 214) RRQRKSRRTI (SEQ ID NO: 215) KAKAAAKKSD (SEQ ID NO: 216) LENPAAKKTV (SEQ ID NO: 217) VDNFDAKKTE (SEQ ID NO: 218) EHAKEDKKTK (SEQ ID NO: 219) KKSEDEKISN (SEQ ID NO: 220) KKMQNFRVST (SEQ ID NO: 221) FEVEEKLKTC (SEQ ID NO: 222) FPNVIKKKST (SEQ ID NO: 223) KLSKIKLVSC (SEQ ID NO: 224) MVGSSKAKSE (SEQ ID NO: 225) NAPSKKSISY (SEQ ID NO: 226) RKTLKKQLSR (SEQ ID NO: 227) RRSEQKAQTE (SEQ ID NO: 228) SILVVKKVTS (SEQ ID NO: 229) SSSNGKKNSR (SEQ ID NO: 230) EVRPTQKKTK (SEQ ID NO: 231) ENSRSRNKSE (SEQ ID NO: 232) EYNQRRILSL (SEQ ID NO: 233) SGKRERKKSE (SEQ ID NO: 234) WPERHRRWSS (SEQ ID NO: 235) YSASRRASSA (SEQ ID NO: 236) QKNTESKKTK (SEQ ID NO: 237) SLEHRSRNTL (SEQ ID NO: 238) NNGKETKKTK (SEQ ID NO: 239) and IKRKNVRHTN (SEQ ID NO: 240) HCVPRDLSWLDLEANMCL (SEQ ID NO: 241) ECDAAEGAEN (SEQ ID NO: 242) EAEAGEGGEN (SEQ ID NO: 243) QQDEEAGEGN (SEQ ID NO: 244) QDDDGGEGNN (SEQ ID NO: 245) ALQDVEDENQ (SEQ ID NO: 246) DEGDAGEGEN (SEQ ID NO: 247) GGEAPQEPQS (SEQ ID NO: 248).

The nucleic acid molecules and polypeptides of the invention are first isolated and subsequently modified by recombinant techniques, or other processes, to add one or more desired biomolecule partition motifs. As used herein with respect to nucleic acid molecules, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. The isolated nucleic acid molecules can be readily manipulated by recombinant DNA techniques well known in the art. The practice of the present invention employs, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology", "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

In one embodiment, nucleic acid molecules of the invention are operably linked to a gene expression sequence which directs the expression of the nucleic acid molecule within a eukaryotic or prokaryotic cell. The "gene expression sequence" is any regulatory nucleotide sequence, such as a promoter sequence or promoter-enhancer combination, which facilitates the efficient transcription and translation of the nucleic acid molecule to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of Moloney murine leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined nucleic acid. The gene expression sequences optionally include enhancer sequences or upstream activator sequences as desired.

The nucleic acid sequence and the gene expression sequence are said to be "operably linked" when they are covalently linked in such a way as to place the transcription and/or translation of the coding sequence under the influence or control of the gene expression sequence. If it is desired that the sequence be translated into a functional protein, two DNA sequences are said to be operably linked if induction of a promoter in the 5' gene expression sequence results in the transcription of the nucleic acid sequence and if the nature of the linkage between the two DNA sequences does not (1) result in the introduction of a frame-shift mutation, (2) interfere with the ability of the promoter region to direct the transcription of the sequence, or (3) interfere with the ability of the corresponding RNA transcript to be translated into a protein. Thus, a gene expression sequence would be operably linked to a nucleic acid sequence if the gene expression sequence were capable of effecting transcription of that nucleic acid sequence such that the resulting transcript might be translated into the desired protein or polypeptide.

The nucleic acid molecules can be delivered to the eukaryotic or prokaryotic cells alone or in association with a vector. In its broadest sense, a "vector" is any vehicle capable of facilitating: (1) delivery of a nucleic acid molecule or polypeptide to a target cell, (2) uptake of a nucleic acid or polypeptide by a target cell, or (3) expression of a nucleic acid molecule or polypeptide in a target cell. Vectors can be provided to cells by transduction or transfection techniques that are well known in the art. Preferably, the vectors transport the nucleic acid or polypeptide into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand (e.g. a receptor, an antigen recognized by an antibody). In this manner, the vector (containing a nucleic acid) can be selectively delivered to a specific cell. In general, the vectors useful in the invention are divided into two classes: biological vectors and chemical/physical vectors. Biological vectors are typically more useful for delivery and/or uptake of nucleic acids. Chemical/physical vectors are typically more useful for delivery and/or uptake of nucleic acids.

Biological vectors include, but are not limited to, plasmids, phagemids, viruses, other vehicles derived from viral or bacterial sources that have been manipulated by the insertion or incorporation of the nucleic acid sequences of the invention, and free nucleic acid fragments which can be linked to the nucleic acid sequences of the invention. Viral vectors are a preferred type of biological vector and include, but are not limited to, nucleic acid sequences from the following viruses: retroviruses, such as Moloney murine leukemia virus; Harvey murine sarcoma virus; murine mammary tumor virus; Rous sarcoma virus; adenoviruses; adeno-associated virus; SV40-type viruses; polyoma viruses; poxviruses; retroviruses; Epstein-Barr virus; papilloma viruses; herpes virus; vaccinia virus; and polio virus. One can readily employ other vectors not named but known in the art.

Selected viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., "*Gene Transfer and Expression, A Laboratory Manual*," W.H. Freeman C.O., New York (1990) and Murry, E. J. Ed. "*Methods in Molecular Biology*," vol. 7, Humana Press, Inc., Clifton, N.J. (1991).

Another virus for certain applications is the adeno-associated virus, a double-stranded DNA virus. The adeno-associated virus can be engineered to be replication-deficient and is capable of infecting a wide range of cell types and species. It has further advantages, such as heat and lipid solvent stability, high transduction frequencies in cells of diverse lineages, and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA encoding a polypeptide or fragment thereof. The heterologous DNA is placed under operable control of transcriptional elements to permit the expression of the heterologous DNA in the host cell.

Systems for mRNA expression in mammalian cells include those such as pRc/CMV or pcDNA1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of a plasmid as a multicopy extrachromosomal element. Another expression vector is the pEF-BOS plasmid containing the promoter of polypeptide Elongation Factor 1α:, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992).

Various techniques may be employed for introducing nucleic acids into cells. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid according to the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

In addition to the biological vectors, chemical/physical vectors may be used to deliver a nucleic acid molecule or polypeptide to a target cell and facilitate uptake thereby. As used herein, a "chemical/physical vector" refers to a natural or synthetic molecule, other than those derived from bacteriological or viral sources, capable of delivering the isolated nucleic acid molecule or polypeptide to a cell.

One such chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vesicles which are useful as delivery vectors in vivo or in vitro. It has been shown that large unilamellar vesicles (LUV), which range in size from 0.2-4.0μ can encapsulate large macromolecules. RNA, DNA, and intact virions can be encapsulated within the aqueous interior and be delivered to cells in a biologically active form (Fraley, et al., *Trends Biochem. Sci.*, v. 6, p. 77 (1981)). In order for a liposome to be an efficient nucleic acid transfer vector, one or more of the following characteristics should be present: (1) encapsulation of the nucleic acid of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Ligands which may be useful for targeting a liposome to a particular cell will depend on the particular cell or tissue type. Additionally when the vector encapsulates a nucleic acid, the vector may be coupled to a nuclear targeting peptide, which will direct the nucleic acid molecules to the nucleus of the host cell.

Liposomes are commercially available from Gibco BRL, Carlsbad, Calif., for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications.

Other exemplary compositions that can be used to facilitate uptake by a target cell of the nucleic acid molecule include calcium phosphate and other chemical mediators of intracellular transport, microinjection compositions, electroporation and homologous recombination compositions (e.g., for integrating a nucleic acid molecule into a preselected location within a target cell chromosome).

The invention also embraces so-called expression kits, which allow the artisan to prepare a desired expression vector or vectors. Such expression kits include at least separate portions of the previously discussed coding sequences. Other components may be added, as desired, as long as the previously mentioned sequences, which are required, are included.

It will also be recognized that the invention embraces the use of cDNA sequences in expression vectors to transfect host cells and cell lines, be these prokaryotic (e.g., *E. coli*), or eukaryotic (e.g., COS cells, yeast expression systems and recombinant baculovirus expression in insect cells). Especially useful are mammalian cells such as human, pig, goat, primate, etc. The cells may be of a wide variety of tissue types, and may be primary cells and cell lines. The expression vectors require that the pertinent sequence, i.e., those nucleic acids described supra, be operably linked to a promoter.

Cells containing the nucleic acids and polypeptides of the invention can be cultured according to standard cell culture techniques. In small scale, the cultures can be contained in culture plates, flasks, and dishes. In larger scale, the cultures can be contained in roller bottles, spinner flasks and other large scale culture vessels such as fermenters. Culturing in a three-dimensional, porous, solid matrix may also be used.

A variety of methodologies well-known to the skilled practitioner can be utilized to obtain isolated polypeptides of the invention from a cell. The polypeptide may be purified from cells by chromatographic means or immunological recognition. Those skilled in the art also can readily follow known methods for isolating polypeptides.

Polypeptides of the invention can be isolated directly from a membrane, such as a cell surface membrane. As used herein with respect to polypeptides, "isolated" means separated from its native environment and present in sufficient quantity to permit its identification or use. Isolation can be achieved, for example, from purification as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art.

Polypeptides of the invention can be isolated from a non-homogenous proteinaceous solution such as a cell homogenate obtained by the disaggregation of a layer of cells or a tissue and forming cell suspensions. The entire culture can be homogenized and subjected to the steps described below for isolation. The cultures can be filtered to remove cells and cell debris. The collected supernatant can be fractionated according to standard chromatographic procedures to facilitate isolation of the desired polypeptide. One of ordinary skill in the art will be familiar with such procedures that include, but are not limited to, size-exclusion chromatography, FPLC, HPLC, gel filtration chromatography, ion-exchange chromatography, hydrophobic chromatography, immune-affinity chromatography, etc.

Where the isolated polypeptide is a therapeutic polypeptide having an altered post-translational modification, assays known in the art relative to each polypeptide can be employed to evaluate the impact of the modification on solubility, stability, efficacy, immunogenicity and so on. Several therapeutic biologics are currently FDA approved, including interferons interferon alfa-2a (Roferon-A®, Hoffmann-La Roche, Inc.), peginterferon alfa-a (Pegasys®, Hoffmann-La Roche, Inc.), interferon alfa-2b (Intron A®, Schering-Plough Corporation), PEGylated interferon alfa-2b (PEG-Intron™, Schering-Plough Corporation), interferon alfa-n1 (Wellferon®, GlaxoSmithKline), interferon alfa-n3 (Alferon N®, Interferon Sciences, Inc.), interferon beta-1a (Avonex®, Biogen, Inc.; and Rebif®, Serono, Inc.), interferon beta-1b (Betaseron®, Chiron Corp. and Berlex Laboratories), interferon gamma-1b (Actimmune®), Intermune Pharmaceuticals, Inc.). In addition, GM-CSF has been approved by the FDA under the tradename of Leukine® (Berlex Laboratories) and IL-2 has been approved for use under the tradename Proleukin® (Chiron Corp®). Both approved and pre-clinical therapeutics can benefit from the addition of biomolecule partition motifs which alter undesirable post-translational modifications.

In specific embodiments, the therapeutic polypeptide is immunogenic and suitable for use in vaccine compositions or in the generation of antibodies, as described elsewhere herein.

Polypeptides of the invention can associate, or form complexes, with other polypeptides which may or may not also have a biomolecule partition motif. Where a polypeptide having a biomolecule partition motif forms a complex with a polypeptide that does not, the polypeptide having a biomolecule partition motif can direct transport of the entire complex to or through a membrane.

The invention also embraces methods for identifying or characterizing agents (e.g., test agents) which bind selectively to the cell surface polypeptides. Cells of the invention will have an increased level of cell surface expression which is advantageous in screening for agents or assessing binding properties of selected agents (e.g., test agents). Some of the agents are inhibitors of a particular function. Assays can be performed to screen and/or determine whether an inhibitor has the ability to inhibit a functional activity of the cell, and also, to determine whether the inhibition is selective.

Any known binding assay may be employed to determine whether a test agent binds to a cell surface polypeptide of the invention. For example, the putative binding agent may be immobilized on a surface and then contacted with a labeled cell surface polypeptide. The amount of cell surface polypeptide which interacts with the putative binding agent or the amount which does not bind to the putative binding agent may then be quantitated to determine whether the putative binding agent binds to cell surface polypeptide.

For determining the binding of a test agent to a cell surface polypeptide, an assay mixture containing the test agent (or a control agent) is incubated under conditions which permit binding to the cell surface polypeptide. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times can be minimized to facilitate rapid, high throughput screening, and typically are between 1 minute and 10 hours.

After incubation, the level of specific binding between the cell surface polypeptides and the test agents is detected by any convenient method available to the user. A separation step is often used to separate bound from unbound components. The separation step may be accomplished in a variety of ways. In some embodiments, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Test agents may be derived from a variety of sources. For example, test agents can be derived from screening degenerate peptide libraries which can be readily prepared in solution, in immobilized form or as phage display libraries. Combinatorial libraries also can be synthesized of peptides containing one or more amino acids. Libraries can be further synthesized of peptides and non-peptide synthetic moieties. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents to be tested.

Typically, a plurality of assays are run in parallel with different agent concentrations to obtain a different response to the various concentrations. Typically, one of these concentrations serves as a negative control, i.e., at zero concentration of agent or at a concentration of agent below the limits of assay detection. Test agents encompass numerous chemical classes, although typically they are organic compounds. In specific embodiments, the test agents are small organic compounds, i.e., those having a molecular weight of more than 50 yet less than about 2500. Test agents comprise functional chemical groups necessary for structural interactions with polypeptides of the invention, and typically include at least an amine, carbonyl, hydroxyl or carboxyl group, preferably at least two of the functional chemical groups and more preferably at least three of the functional chemical groups. The test agents can comprise cyclic carbon or heterocyclic structure and/or aromatic or polyaromatic structures substituted with one or more of the above-identified functional groups. Test agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids having non-natural bonds or subunits are also contemplated.

A variety of other reagents also can be included in the assay mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components.

The polypeptides of the invention can also be used in the generation of antibodies or a functionally active immunogen binding antibody fragment. Methods of the invention are ideally suited for the generation of antibodies, as inclusion of the biomolecule partition motif provides cell surface expression of any desired immunogen from which a variety of antibodies can be obtained by conventional methods known in the art.

Antibodies are well known to those of ordinary skill in the science of immunology. As used herein, the term "antibody" means not only intact antibody molecules but also fragments of antibody molecules retaining immunogen binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments which lack the Fc fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv) and fusion polypeptides. Preferably, the antibodies of the invention are monoclonal. Alternatively the antibody may be a polyclonal antibody. The preparation and use of polyclonal antibodies is also known to one of ordinary skill in the art. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "$F(ab')_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing cell surface polypeptides of the invention, or a fragments thereof, as an immunogen. One method of obtaining antibodies is to immunize suitable host animals with an immunogen and to follow standard procedures for polyclonal or monoclonal production. The immunogen will be derived from, for example, a viral, bacterial or other pathogenic organism, and will contain a biomolecule partition motif to facilitate presentation of the immunogen on the cell surface. Methods of the invention increase the expression levels of an immunogen on a cell surface, thereby enhancing the immunogenic response. Methods of the invention can also provide immunogens that may otherwise be trapped and degraded in the endoplasmic reticulum, thereby providing unique immunogens and thus, unique antibodies.

Immunization of a suitable host can be carried out in a number of ways. Nucleic acid sequences encoding cell surface polypeptides of the invention can be provided to the host in a delivery vehicle that is taken up by immune cells of the host. The cells will in turn express the polypeptide on the cell surface, as mediated by the biomolecule partition motif, generating an immunogenic response in the host. Alternatively, nucleic acid sequences encoding polypeptides of the invention can be expressed in cells in vitro, followed by isolation of the polypeptide and administration of the polypeptide to a suitable host in which antibodies are raised. In specific embodiments, the polypeptide is provided as a vaccine (e.g., a DNA or polypeptide vaccine) and the immunogenic response in the host is sufficient to protect against an infectious pathogen.

Using either approach, antibodies can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently obtained from hybridoma cells engineered to express an antibody. Such antibodies can first be obtained from polypeptides of the invention as previously described. Methods of making hybridomas are well known in the art. The hybridoma cells can be cultured in a suitable medium, and spent medium can be used as an antibody source. Polynucleotides encoding the antibody can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition; e.g., Pristane.

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205. In one another version, the heavy chain and light chain C regions are replaced with human sequence. In another version, the CDR regions comprise amino acid sequences for recognition of antigen of interest, while the variable framework regions have also been converted to human sequences. See, for example, EP 0329400. It is well established that non-CDR regions of a mammalian antibody may be replaced with corresponding regions of non-specific or hetero-specific antibodies while retaining the epitope specificity of the original antibody. This technique is useful for the development and use of humanized antibodies in which non-human CDRs are covalently joined to human FR and/or Fc/pFc' regions to produce a functional antibody. In a third version, variable regions are humanized by designing consensus sequences of human and mouse variable regions, and converting residues outside the CDRs that are different between the consensus sequences.

Construction of phage display libraries for expression of antibodies, particularly the Fab or scFv portion of antibodies, is well known in the art (Heitner, 2001). The phage display antibody libraries that express antibodies can be prepared according to the methods described in U.S. Pat. No. 5,223,409 incorporated herein by reference. Procedures of the general methodology can be adapted using the present disclosure to produce antibodies of the present invention. The method for producing a human monoclonal antibody generally involves (1) preparing separate heavy and light chain-encoding gene libraries in cloning vectors using human immunoglobulin genes as a source for the libraries, (2) combining the heavy and light chain encoding gene libraries into a single dicistronic expression vector capable of expressing and assembling a heterodimeric antibody molecule, (3) expressing the assembled heterodimeric antibody molecule on the surface of a filamentous phage particle, (4) isolating the surface-expressed phage particle using immunoaffinity techniques such as panning of phage particles against a preselected immunogen, thereby isolating one or more species of phagemid containing particular heavy and light chain-encoding genes and antibody molecules that immunoreact with the preselected immunogen. The preselected immunogen can be provided by or obtained from cells of the invention that express polypeptides with a biomolecule partition motif on the cell surface, or in other cellular membranes.

Single chain variable region fragments are made by linking light and heavy chain variable regions by using a short linking peptide. Any peptide having sufficient flexibility and length can be used as a linker in a scFv. Usually the linker is selected to have little to no immunogenicity. An example of a linking peptide is $(GGGGS)_3$ (SEQ ID NO: 260), which bridges approximately 3.5 nm between the carboxy terminus of one variable region and the amino terminus of another variable region. Other linker sequences can also be used. All or any portion of the heavy or light chain can be used in any combination. Typically, the entire variable regions are included in the scFv. For instance, the light chain variable region can be linked to the heavy chain variable region. Alternatively, a portion of the light chain variable region can be linked to the heavy chain variable region, or a portion thereof. Compositions comprising a biphasic scFv could be constructed in which one component is a polypeptide that recognizes an immunogen and another component is a different polypeptide that recognizes a different antigen, such as a T cell epitope.

ScFvs can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect or mammalian cells, or prokaryotic, such as *Escherichia coli*, and the protein expressed by the polynucleotide can be isolated using standard protein purification techniques.

A particularly useful system for the production of scFvs is plasmid pET-22b(+) (Novagen, Madison, Wis.) in *E. coli*. pET-22b(+) contains a nickel ion binding domain consisting of 6 sequential histidine residues, which allows the expressed protein to be purified on a suitable affinity resin. Another example of a suitable vector for the production of scFvs is pcDNA3 (Invitrogen, San Diego, Calif.) in mammalian cells, described above.

Expression conditions should ensure that the scFv assumes functional and, preferably, optimal tertiary structure. Depending on the plasmid used (especially the activity of the promoter) and the host cell, it may be necessary or useful to modulate the rate of production. For instance, use of a weaker promoter, or expression at lower temperatures, may be necessary or useful to optimize production of properly folded scFv in prokaryotic systems; or, it may be preferable to express scFv in eukaryotic cells.

In another aspect, the invention provides vaccine compositions and methods for making and using the same. The vaccine composition can comprise a nucleic acid of the invention having a biomolecule partition motif (i.e., a "DNA vaccine") and encoding a pathogenic polypeptide or fragment thereof. Immunization of a suitable host can be carried out, for example, by providing the nucleic acid to the host in a delivery vehicle that is taken up by immune cells of the host.

The cells will in turn express the polypeptide on the cell surface, as mediated by the biomolecule partition motif, producing the desired immunogenic response in the host, thereby immunizing the host against the pathogenic organisms.

Typically, DNA vaccine compositions of the invention are formulated with suitable pharmaceutical excipients. DNA vaccine compositions of the invention can optionally include adjuvants, however enhanced immunogenicity of the compositions may eliminate the need for additional immunostimulation.

Alternatively, vaccine compositions of the invention can comprise polypeptides of the invention, or fragments thereof, containing a biomolecule partition motif that has been included to enhance cell surface expression of the polypeptide prior to its isolation and incorporation into the vaccine composition. Optionally, the biomolecule partition motif can be removed from the immunogenic polypeptide prior to incorporation into the vaccine composition.

Vaccine compositions of the invention are suitable for administration to a variety of hosts, including but not limited to mammals, animals (e.g., domestic and farm animals) and humans of all ages.

Nucleic acid and polypeptide sequences of the invention for use in vaccine compositions can encode immunogenic polypeptides, or fragments thereof, derived from infectious pathogens. Examples of infectious virus include: Retroviridae (e.g., human immunodeficiency viruses, such as HIV-1, also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever virus); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herperviridae (herpes simplex virus (HSV) 1 and 2, varicella zoster virus, cytomegalovirus (CMV), herpes viruses); Poxviridae (variola virsues, vaccinia viruses, pox viruses); and Iridoviridae (e.g., African swine fever virus); and unclassified viruses (e.g., the etiological agents of Spongiform encephalopathies, the agent of delta hepatitides (thought to be a defective satellite of hepatitis B virus), the agents of non-A, non-B hepatitis (class 1 —internally transmitted; class 2 —parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria* sps (e.g., *M. tuberculosis, M. avium, M. Intracellulare, M kansaii, M gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter erogenes, Klebsiella pneuomiae, Pasturella multicoda, Bacteroides* sp., *Fusobacterium nucleatum, Sreptobacillus moniliformis, Treponema pallidium, Treponema pertenue, Leptospira*, and *Actinomeyces israelli.*

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium falciparum* and *Toxoplasma gondii.*

Vaccine compositions of the invention can comprise nucleic acid and polypeptide sequences encoding immunogenic polypeptides, or fragments thereof derived from any infectious pathogens, including those described herein. Inclusion of a biomolecule partition motif will increase cell surface expression of the immunogens, thereby enhancing selection and isolation of the immunogenic polypeptide prior to host administration or, when administered as a DNA vaccine, enhancing the immunogenic response in vivo.

An effective amount of the vaccine composition is one in which a sufficient immunological response to the vaccine is raised to protect a host exposed to an infectious pathogen. Preferably, the host is protected to an extent in which from one to all of the adverse physiological symptoms or effects of the disease to be prevented are found to be significantly reduced.

The vaccine composition can be administered in a single dose, or in repeated doses. Dosages may contain, for example, from 1 to 1,000 micrograms of immunogen, but should not contain an amount of immunogen sufficient to result in an adverse reaction or physiological symptoms of infection. Methods are known in the art for determining suitable dosages of active immunogenic agent.

The composition containing the present vaccine may be administered in conjunction with an adjuvant or with an acceptable carrier which may prolong or sustain the immunological response in the host. An adjuvant is a substance that increases the immunological response to the present vaccine when combined therewith. The adjuvant may be administered at the same time and at the same site as the vaccine or at a different time, for example, as a booster. Adjuvants also may advantageously be administered to the host in a manner or at a site or location different from the manner, site or location in which the vaccine is administered. Adjuvants include aluminum hydroxide, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete adjuvant, Freund's complete adjuvant, and the like. Toxin-based adjuvants, such as diphtheria toxin, tetanus toxin and pertussis toxin, may be inactivated prior to use, for example, by treatment with formaldehyde.

Vaccine compositions are ideally administered directly to a host not yet exposed to the relevant pathogen. Vaccine compositions can be administered orally or parenterally. Examples of parenteral routes of administration include intradermal, intramuscular, intravenous, intraperitoneal, subcutaneous and intranasal routes of administration. When administered as a solution, the vaccine compositions can be prepared in the form of an aqueous solution, a syrup, an elixir, or a tincture. Such formulations are known in the art, and are prepared by dissolution of the antigen and other appropriate additives in the appropriate solvent systems. Such solvents include water, saline, ethanol, ethylene glycol, glycerol, Al fluid, etc. Suitable additives known in the art include certified dyes, flavors, sweeteners, and antimicrobial preservatives, such as thimerosal (sodium ethylmercurithiosalicylate). Such solutions may be stabilized, for example, by addition of partially hydrolyzed gelatin, sorbitol, or cell culture medium, and may be buffered by methods known in the art, using reagents known in the art, such as sodium hydrogen phosphate, sodium dihydrogen phosphate, potassium hydrogen phosphate and/or potassium dihydrogen phosphate.

Liquid formulations may also include suspensions and emulsions. The preparation of suspensions, for example using a colloid mill, and emulsions, for example using a homogenizer, is known in the art.

Parenteral dosage forms, designed for injection into body fluid systems, require proper isotonicity and pH buffering to the corresponding levels of host body fluids. Parenteral formulations must also be sterilized prior to use. Isotonicity can be adjusted with sodium chloride and other salts as needed. Other solvents, such as ethanol or propylene glycol, can be used to increase solubility of ingredients of the composition and stability of the solution. Further additives which can be used in the present formulation include dextrose, conventional antioxidants and conventional chelating agents, such as ethylenediamine tetraacetic acid (EDTA).

It is well within the level of ordinary skill in the art to adjust administration routes, dosages and formulations to achieve the desired result for a particular host.

In another aspect, biomolecule partition motifs of the invention are useful for rescue of mutated or otherwise defective polypeptides that are unable to reach a membrane. Abnormal protein folding and trafficking is associated with a growing number of diseases. Diseases such as Alzheimer's and prion-related diseases (such as Creutzfeldt-Jacob diseases or Scrapie) are characterized by the presence of high levels of insoluble protein aggregates in brain tissue. These plaques appear to be aggregates of misfolded β-amyloid or prion proteins. In cystic fibrosis, 70% of such patients arise due to the deletion of a single amino acid (ΔF508) in the cystic fibrosis transmembrane conductance regulator (CFTR). This mutation causes the CFTR protein to reside in ER thus unable to traffick to the site of action on the cell surface. Elongation of the QT interval during cardiac action potential could cause Torsade de Pointes which may lead to cardiac sudden death. There are also a number of mutations that have been identified in the human ether-a-go-go related gene (hERG), which encode a pore-forming subunit of the potassium channel. A subset of these mutations causes the HERG protein reside in ER, reducing the potassium current density, thereby causing prolongation of the QT interval. In addition, more than 50% of the drugs were withdrawn from the market because of their side effect which caused QT-interval prolongation. Most of these drugs have been shown to inhibit the HERG potassium channel currents and an unknown number of them affecting the cell-surface trafficking of the HERG potassium channel. Proper targeting of these polypeptides by the addition of a biomolecule partition motif can restore function and alleviate symptoms associated with these disorders.

Genetic alteration of a host cell includes all transient and stable changes of the cellular genetic material which are created by the addition of exogenous genetic material. Examples of genetic alterations include any gene transfer procedure, such as introduction of a functional nucleic acid sequence to replace a mutated or deleted sequence or introduction of a nucleic acid sequence that encodes a therapeutic gene product having one or more biomolecule partition motifs. Thus, according to methods of the invention, one or more biomolecule partition motifs can be incorporated into the genomic locus of the defective gene by homologous recombination or viral integration. Thus, a nucleic acid sequence encoding the gene of interest and one or more biomolecule partition motifs can be either stably or extrachromosomally expressed in a cell, thereby restoring or gaining function in the cell.

Thus, as will be apparent to one of ordinary skill in the art, a variety of suitable methods are available for transferring nucleic acids of the invention comprising corrective genetic material into cells. For example, the selection of an appropriate vector to deliver a therapeutic agent for a particular condition amenable to gene replacement therapy and the optimization of the conditions for insertion of the selected expression vector into the cell, are within the scope of one of ordinary skill in the art without the need for undue experimentation.

The promoter associated with delivery vectors characteristically has a specific nucleotide sequence necessary to initiate transcription. Optionally, the exogenous genetic material further includes additional sequences (i.e., enhancers) required to obtain the desired gene transcription activity. For the purpose of this discussion an "enhancer" is simply any nontranslated DNA sequence which works contiguous with the coding sequence (in cis) to change the basal transcription level dictated by the promoter. Preferably, the exogenous genetic material is introduced into the cell genome immediately downstream from the promoter so that the promoter and coding sequence are operatively linked so as to permit transcription of the coding sequence. A preferred retroviral expression vector includes an exogenous promoter element to control transcription of the inserted exogenous sequence. Such exogenous promoters include both constitutive and inducible promoters.

Naturally-occurring constitutive promoters control the expression of essential cell functions. As a result, a sequence under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR) (Scharfmann et al., 1991, Proc. Natl. Acad. Sci. USA, 88:4626-4630), adenosine deaminase, phosphoglycerol kinase (PGK), pyruvate kinase, phosphoglycerol mutase, the actin promoter (Lai et al., 1989, Proc. Natl. Acad. Sci. USA, 86:10006-10010), and other constitutive promoters known to those of skill in the art. In addition, many viral promoters function constitutively in eukaryotic cells. These include: the early and late promoters of SV40; the long terminal repeats (LTRS) of Moloney Leukemia Virus and other retroviruses; and the thymidine kinase promoter of Herpes Simplex Virus, among many others. Accordingly, any of the above-referenced constitutive promoters can be used to control transcription of a heterologous nucleic acid sequence.

Nucleic acid sequences of the invention that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic polypeptide in the genetically modified cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid of the invention, the expression vector preferably includes a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

The selection and optimization of a particular expression vector for expressing a nucleic acid sequence in an isolated cell is accomplished by obtaining the sequence, preferably with one or more appropriate control regions (e.g., promoter, insertion sequence); preparing a vector construct comprising the vector into which is inserted the sequence; transfecting or transducing cultured cells in vitro with the vector construct; and determining whether the expression product is present in the cultured cells.

In the present invention, the preferred method of introducing exogenous genetic material into cells is by transducing the cells in situ on the matrix using replication-deficient retroviruses. Replication-deficient retroviruses are capable of directing synthesis of all virion proteins, but are incapable of making infectious particles. Accordingly, these genetically altered retroviral vectors have general utility for high-efficiency transduction of genes in cultured cells, and specific utility for use in the method of the present invention. Retroviruses have been used extensively for transferring genetic material into cells. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with the viral particles) are provided in the art.

The major advantage of using retroviruses is that the viruses insert efficiently a single copy of the gene encoding the therapeutic agent into the host cell genome, thereby permitting the exogenous genetic material to be passed on to the progeny of the cell when it divides. In addition, gene promoter sequences in the LTR region have been reported to enhance expression of an inserted coding sequence in a variety of cell types. The major disadvantages of using a retrovirus expression vector are (1) insertional mutagenesis, i.e., the insertion of the nucleic acid sequence into an undesirable position in the target cell genome which, for example, leads to unregulated cell growth and (2) the need for target cell proliferation in order for the therapeutic gene carried by the vector to be integrated into the target genome. Despite these apparent limitations, delivery of a nucleic acid sequence via a retrovirus can be efficacious if the efficiency of transduction is high and/or the number of target cells available for transduction is high.

Yet another viral candidate useful as an expression vector for transformation of cells is the adenovirus, a double-stranded DNA virus. Like the retrovirus, the adenovirus genome is adaptable for use as an expression vector for gene transduction, i.e., by removing the genetic information that controls production of the virus itself. Because the adenovirus functions usually in an extrachromosomal fashion, the recombinant adenovirus does not have the theoretical problem of insertional mutagenesis. On the other hand, adenoviral transformation of a target cell may not result in stable transduction. However, more recently it has been reported that certain adenoviral sequences confer intrachromosomal integration specificity to carrier sequences, and thus result in a stable transduction of the exogenous genetic material.

Thus, as will be apparent to one of ordinary skill in the art, a variety of suitable methods are available for transferring genetic material of interest into cells. The selection of an appropriate vector to deliver a nucleic acid sequence encoding a polypeptide having a biomolecule partition motif for a particular condition amenable to gene replacement therapy and the optimization of the conditions for insertion of the selected expression vector into the cell, are within the scope of one of ordinary skill in the art without the need for undue experimentation.

In another aspect, addition of a biomolecule partition motif can be achieved by providing a cell with a biomolecule partition motif linked to a tag, wherein the tag has affinity to a polypeptide of interest (e.g., proteins having trafficking defects associated with human diseases). The methodology is well known in the art, see, for example Gestwicki et al., (2004) Science, 29:306, 865-9, the contents of which are incorporated herein by reference. Delivery of such a bipartite molecule may be achieved by passive diffusion or facilitated transduction.

Specific embodiments of the invention are further described by way of the following non-limiting Examples:

EXAMPLES

Example 1

Genetic Screen for Trafficking Motifs

Figure 1A:
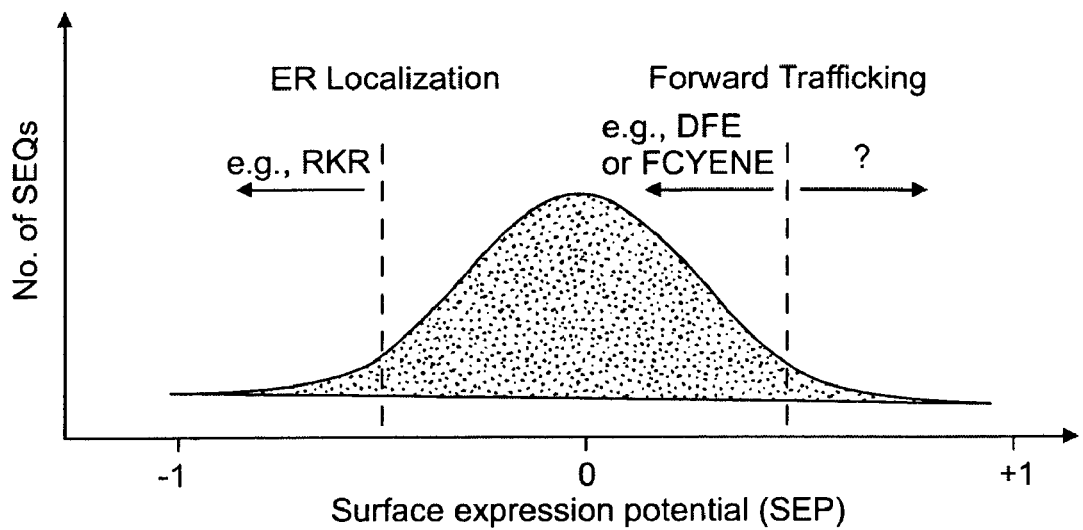
FIG. 1B shows a yeast growth test of the Kir2.1 inward rectifier potassium channel with different fusion peptides, Kir2.1-RKR and Kir2.1-RAA, in the presence of 4 mM potassium vs. 100 mM potassium.
FIG. 1C shows, on the left, a schematic diagram of the Kir2.1 reporter with its native forward transport sequence motif, FCYENE (SEQ ID NO: 249), and, on the right, growth comparison of ~10,000 library transformants in media containing 4 mM or 100 mM potassium as indicated. The circled areas illustrate colonies grown in a selection plate.

Within a random pool of peptide sequences, it was predicted that each would possess a certain degree of surface expression potential (SEP), which could then be assigned an arbitrary number. Within a diversity space of random amino acid sequences, one would predict a large majority of sequences would have no effects in either forward trafficking (i.e., the ability to facilitate surface expression) or retention (i.e., the ability to confer intracellular localization in ER or Golgi). Hence a plot of number of sequences against SEP value would display a large number of sequences clustered near zero (FIG. 1A). Those close to a value of +1, e.g., DXE or FCYENE (SEQ ID NO: 249) (Ma et al., 2001; Nishimura and Balch, 1997), would have strong forward trafficking potential. Conversely, those with a value close to −1, e.g., the RKR motif, would have strong retention/retrieval potential (FIG. 1A). The ability of a protein to express on the cell surface would be the net of these two opposing forces, which are subject to other regulatory factors including accessibility (Schwappach et al., 2000) and zoning of a signal motif (Shikano and Li, 2003). Because the existing forward transport sequences are recessive, neither the DXE nor FCYENE motifs (SEQ ID NO: 249) would have an SEP value positive enough to supersede the negative potential of RKR, hence resulting in intracellular localization.

To isolate potential sequence motifs which mediate forward trafficking of membrane proteins and have a SEP value larger than that of DXE or FCYENE (SEQ ID NO: 249), a genetic screen was developed using the Kir2.1 inward rectifier potassium channel as a reporter protein. This system takes advantage of the fact that yeast cells require TRK1 and TRK2 in order to survive in normal potassium media (~4 mM). The mutant phenotype of a double knockout (SGY1528) may be complemented with a number of mammalian potassium channels, including Kir2.1 (Tang et al., 1995). Fusion of Kir2.1 with an ER localization signal such as the RKR motif from Kir6.2 potassium channel leads to effective intracellular localization in mammalian cells (Shikano and Li, 2003). Accordingly, Kir2.1 was fused with the RKR motif from Kir6.2 potassium channel.

A. Molecular biology: The yeast expression vector for mammalian Kir2.1 was generated by cloning mouse Kir2.1 cDNA in pADNS vector at HindIII and NotI. The artificial PstI site was inserted at the C-terminus of Kir2.1 by replacing the last residue (I) with the PstI sequence (LQ). The DNA fragment encoding the C-terminal 36 amino acids of mouse Kir6.2 (LLDALTLASSRGPLRKRSVAVAKAKPKFSISPD-SLS) (SEQ ID NO: 261) was generated by annealing and extending the complementary oligonucleotides with PstI and NotI overhangs and then ligating to Kir2.1.

Figure 1B:
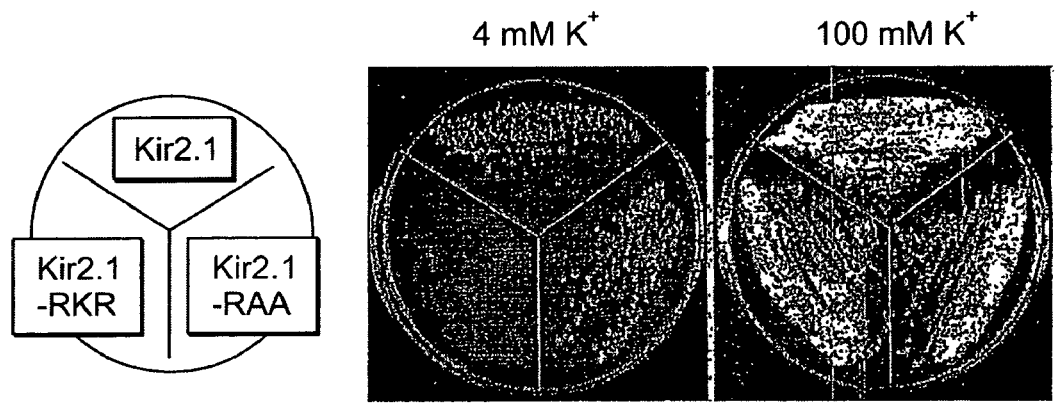

B. Growth test of fusion peptide: The ability of the fused RKR motif to complement growth of SGY1528 at 4 mM potassium concentration was tested. RKR was then specifically mutated to RAA to test its ability to reverse the effect and allow renewed surface expression (FIG. 1B).

The fusion of the RKR motif to Kir2.1 supersedes the forward transport effect conferred by Kir2.1's native forward transport sequence motif, FCYENE (SEQ ID NO: 249), and dominantly relocates the protein to the ER compartment. Using this reporter system, the existence of sequence motifs with the ability to confer surface expression by overriding the retention effect caused by the RKR ER localization signal was confirmed.

Figure 1C:
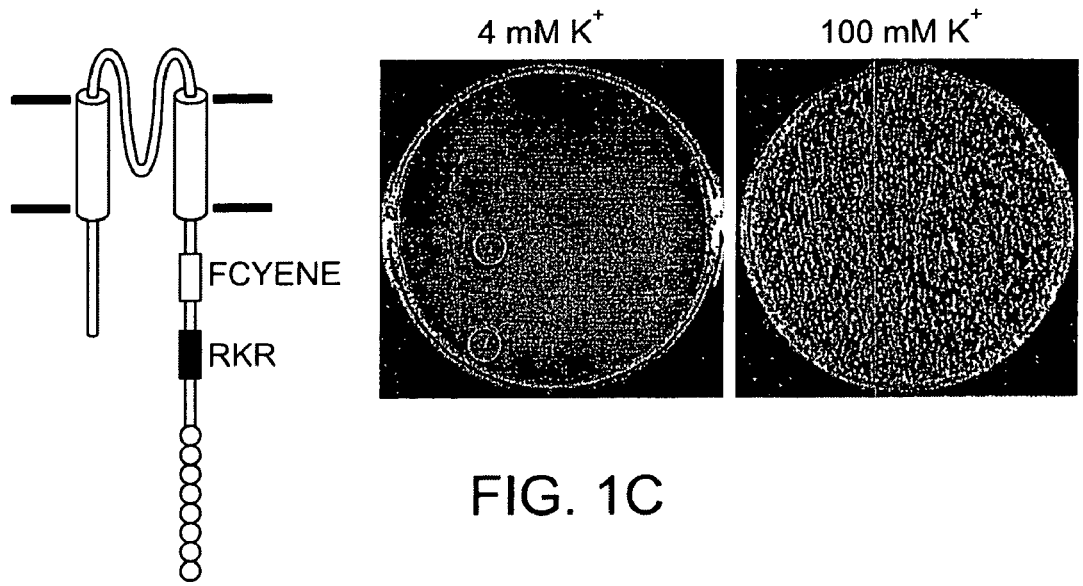

Kir2.1 has a native forward transport sequence motif, FCYENE (SEQ ID NO: 249), which was shown to confer an increase in steady state expression on the cell surface (FIG. 1C, left panel) (Ma et al., 2001). The fusion of the RKR motif to Kir2.1 supersedes the forward transport effect and dominantly relocates the protein to the ER compartment, in good agreement with current belief that an ER localization signal is dominant over a forward transport signal. Using this reporter system, the existence of sequence motifs with the ability to confer surface expression by overriding the retention effect caused by the RKR ER localization signal was tested for.

C. Library selection: With the combined advantages of positive selection of activity under a biological threshold and clonal expression of reporter proteins, a random peptide library was constructed for yeast growth selection. Eight (8) amino acid random peptides were chosen in light of two considerations: first, the epitope was required to be long enough to encode sufficient diversity space in order to allow for specific recognition by an interacting protein (Chung et al., 2003); second, based on structural information, most proteins have their C-terminus exposed, and many spatial localization signals are found at the C-terminus (Chung et al., 2002).

The Sac1 site was engineered 9aa downstream of the RKR signal (this caused mutation of PK to EL) to replace SISPD-SLS (SEQ ID NO: 254) with the DNA fragments encoding the X8 random peptide library. The X8 library DNA fragments were generated by annealing and extending the sense strand (5'-GAGCTCTTT(NNK)8TA000GGCCGCTACAT-ACA, where N indicates any of A, T, C, G and K indicates either of G or T) and anti-sense strand (5'-TGTATGTAGCG-GCCGCCTA) (SEQ ID NO: 262) oligonucleotides that were synthesized to randomly encode 8 amino acids preceded by Phe with Sac1 and NotI overhangs. E. coli were transformed with Kir2.1-RKR-X8 library plasmids by electroporation and plated at 10,000 colonies/plate to isolate the plasmids.

D. Yeast screening for surface Kir2.1 expressing clones: SGY1528 (MATa; ade2-1; cant-100; his3-11,15; leu2-3,112; trpl-1; ura3-1; trkl: HIS3; trk2: TRP1) does not grow on low potassium media but can be rescued by heterologous expression of Kir2.1. Yeast were transformed with pADNS plasmids and grown on dropout media without leucine, supplemented with 100 mM KCl. Transformants were then plated on 4 mM KCl media to test for complementation.

Example 2

Characterization of Dominant Surface Expression Signals

A. Screening of the X8 library: For screening of the X8 library, yeast were transformed with 300 µg of Kir2.1-RKR-X8 library plasmids, and approximately $2 \times 10^6$ clones of transformants (as estimated by growth on 100 mM KCl) were directly plated on 4 mM KCl plates. After 5 days of culture the rescued colonies were picked and further grown on separate plates for plasmid isolation. To confirm the growth dependence on the plasmid, the isolated plasmids were re-transformed to SGY1528 and tested for growth on 4 mM KCl plates. Those found to grow at 4 mM potassium were subject to retransformation. From approximately 200 clones that were confirmed for the growth upon re-transformation, the X8 sequences were analyzed. 67 distinct sequences were isolated. To identify those with activity in mammalian cells, the sequences were transferred to a mammalian cell expression vector and individually expressed via transient transfection in HEK293 cells. The mammalian expression vectors were constructed by transferring the chimeric Kir2.1 cDNAs to a pcDNA3.1(+) vector (Invitrogen, Carlsbad, Calif.) at HindIII and NotI. For detection of surface expression, the HA epitope (YPYDVPDYA) (SEQ ID NO: 263) was inserted at position 117 of Kir2.1. This HA was reported to cause no obvious effect on channel properties (Zerangue et al., 1999).

B. Flow cytometry analyses of HA-tagged Kir2.1 channel in HEK293 cells: The surface expression of an otherwise ER-localized HA-tagged Kir2.1-RKR protein was evaluated by anti-HA antibody and quantified with flow cytometry. The transfected HEK293 cells were harvested by incubation with 0.5 mM EDTA-PBS for 10 min at 37° C. and washed with Hanks' Balanced Salt Solution supplemented with 5 mM HEPES (pH 7.3) and 2% FBS (staining medium). All the Ab incubations and washings were performed in staining medium at 4° C. For surface Kir2.1 channel, the cells were stained with rat monoclonal high-affinity anti-HA (Roche Applied Sciences, IN) followed by FITC-conjugated goat anti-rat IgG (Vector, Burlingame, Calif.). The stained cells were examined for surface expression with FACSCalibur (BD Biosciences, San Jose, Calif.).

Based on their effectiveness in conferring the surface expression of Kir2.1-RKR, these sequences may be divided into three groups (FIG. 2, A & B). Group 1 essentially shows no detectable surface expression, similar to that of the reporter fusion of Kir2.1-RKR. This group may represent those motifs possessing activity specific in yeast or a different mechanism to rescue the yeast growth. Group 2 sequences are those capable of directing surface expression at a level similar to that of the wild type Kir2.1 or Kir2.1-RAA control. Group 3 comprises motifs conferring surface expression levels higher than that of wild type. This represents a gain of function by potentiating the surface expression of the channel protein.

Both electrophysiological recording and rubidium flux assay were carried out to compare voltage activation and other biophysical properties of Kir2.1-RKR-SWTY (peptide disclosed as SEQ ID NO: 251) (clone #4) with wild type Kir2.1 channels. The RGRSWTY (SEQ ID NO: 1) (#4) motif (termed SWTY (SEQ ID NO: 250)) was selected for further analyses because of its potency in potentiating surface expression. To test whether the SWTY (SEQ ID NO: 250) effect is RKR-dependent, the expression of Kir2.1-RKR-SWTY (peptide disclosed as SEQ ID NO: 251) was compared to that of Kir2.1-RAA-SWTY (peptide disclosed as SEQ ID NO: 257) via flow cytometry.

The flow cytometry data indicate that the expression levels were essentially identical (FIG. 2C, right panels). More importantly, both constructs, regardless of RKR or RAA, displayed comparably higher surface expression levels than that of wild type. These results support that RGRSWTY (SEQ ID NO: 1) conferred a gain of function and did not exert the effect by simply masking RKR activity, which would have resulted in a surface expression level similar to that of wild type Kir2.1.

C. SWTY motif (SEQ ID NO: 250) specificity: To evaluate whether the SWTY motif (SEQ ID NO: 250) is reporter-specific, CD4, a type I membrane protein with robust surface expression, was fused with the RKR or RAA motif, and the surface expression was measured in the presence vs. absence of the SWTY motif (SEQ ID NO: 250). A CD4 (HA)$_3$ vector encoding human $CD_4$ extracellular and transmembrane domains attached with three HA repeats was generated as described (Shikano and Li, 2003). The 36aa sequence of Kir6.2 was cloned into the C-terminus of CD4 (HA)$_3$ at BamHI and EcoRI.

The transfected HEK293 cells were harvested by incubation with 0.5 mM EDTA-PBS for 10 min at 37° C. and washed with Hanks' Balanced Salt Solution supplemented with 5 mM HEPES (pH 7.3) and 2% FBS (staining medium). All the antibody incubations and washings were performed in staining medium at 4° C. For surface CD4, FITC-conjugated anti-human CD4 mAb (DAKO, Carpinteria, Calif.) was used. The stained cells were examined for surface expression with FACSCalibur (BD Biosciences, San Jose, Calif.).

A fusion of CD4 with the RKR motif dramatically reduced the surface expression to a background level. Similar to Kir2.1, mutation of RKR to RAA restored the surface expression. In the presence of the SwTYmotif(SEQ ID NO: 250), CD4 surface expression no longer showed any effect from RKR, indicating that SWTY (SEQ ID NO: 250) was again effective and overriding the effect of RKR (FIG. 2D). The surface expression in CD4-RKR-SWTY (peptide disclosed as SEQ ID NO: 257) or CD4-RAA-SWTY (peptide disclosed as SEQ ID NO: 257) were slightly higher than that of CD4-RAA but less pronounced compared to Kir2.1, presumably due to the already robust expression of CD4, although one cannot rule out that different oligomeric states of CD4 and Kir2.1 affect elevated surface expression. Together, the results demonstrate that the SWTY motif (SEQ ID NO: 250) is effective in overriding RKR-mediated ER localization in both the tetrameric Kir2.1 channel and monomeric CD4 surface antigen.

Example 3

Interaction Between Phosphorylated SWTY (SEQ ID NO: 250) and 14-3-3 Proteins

A. Immunoprecipitation: To test whether the SWTY motif (SEQ ID NO: 250) functions by recruiting protein machinery that actively mediates the surface expression of membrane protein, HEK293 cells were transfected with a control vector, HA-tagged Kir2.1-RKR and Kir2.1-RKR-SWTY (peptide disclosed as SEQ ID NO: 251), respectively. The transfected cells were harvested, lysed and immunoprecipitated with anti-HA antibody. For immunoprecipitation, transfected cells were washed with PBS once and lysed with lysis buffer (1% NP40, 25 mM Tris, 150 mM NaCl, pH 7.50) with protease inhibitor cocktails for 20 min at 4° C. After spinning for 20 min at 11,000 g, the supernatant was mixed with protein A-conjugated agarose beads which were pre-incubated with 1 µg of anti-HA Ab or anti-14-3-3R Ab (Santa Cruz). After 5 hour incubation, the beads were washed 5 times with lysis buffer and then boiled with 2× sample buffer for SDS-PAGE analysis.

The immunoprecipitated materials were fractionated and visualized by silver stain (FIG. 3A). A scale-up immunoprecipitation combined with matrix-assisted laser desorption/ionisation-time (MALDI-TOF) of flight mass spectrometry was performed. The biotin-conjugated peptides for SWTY (SEQ ID NO: 250) and control sequences were synthesized (Abgent, San Diego, Calif.) and immobilized on streptavidin-sepharose beads. The cell lysate of HEK293 was incubated with the peptide-immobilized beads for 5 hour and washed 5 times with lysis buffer. The beads were boiled, and the eluate was analyzed for 14-3-3 by SDS-PAGE followed by silver staining. The specific interaction between Kir2.1-RKR-SWTY (peptide disclosed as SEQ ID NO: 251) and 14-3-3 isoforms identified as two SWTY-specific bands (SEQ ID NO: 250) was further confirmed using recombinantly expressed 14-3-3 isoforms in cells or in purified forms.

C. 14-3-3 binding and surface expression analysis: To test the possibility of a link of the surface expression to the binding to 14-3-3, a series of Ala substitutions scanning the FRGRSWTY motif (SEQ ID NO: 2) was constructed to determine the residues critical for the effects. The surface expression of individual Ala substitution mutants was examined via flow cytometry. FIG. 3B shows a series of flow cytometry experiments examining the surface expression of individual Ala substitution mutants. Of the eight mutants, FAGRSWTY (SEQ ID NO: 3) and FRGRSWAY (SEQ ID NO: 4) were most effective, completely abolishing the surface expression (FIG. 3B). FRGASWTY (SEQ ID NO: 5) also displayed a noticeable reduction of surface expression, comparable to the level of wild-type Kir2.1 or Kir2.1-RAA. Thus, the -2 Thr and upstream Arg residues are important for elevated surface expression.

Immunoprecipitations were performed using cells transfected with vector controls and Kir2.1-RKR-SWTY (SEQ ID NO: 251) mutants with Ala substitutions. For immunoprecipitation, transfected cells were washed with PBS once and lysed with lysis buffer (1% NP40, 25 mM Tris, 150 mM NaCl, pH 7.50) with protease inhibitor cocktails for 20 minutes at 4° C. After spinning for 20 minutes at 11,000 g, the supernatant was mixed with protein A-conjugated agarose beads which were pre-incubated with 1 µg of anti-HA antibody or anti-14-3-3R antibody (Santa Cruz). After 5 hour incubation, the beads were washed 5 times with lysis buffer and then boiled with 2× sample buffer for SDS-PAGE analysis.

The resultant immunoprecipitates were separated on SDS-PAGE and visualized by silver stain (FIG. 3C, upper panel). The immunoprecipitates were also blotted with antibodies against Kir2.1 and 14-3-3 (FIG. 3C, lower panels). For blotting of Kir2.1 proteins in the surface fraction, the cells were harvested with EDTA-PBS and incubated with the corresponding antibodies for 20 min at 4° C. in staining medium, washed extensively, and then lysed with 1% NP40 buffer. The supernatant after centrifuge was incubated with protein A-conjugated beads for 5 hr at 4° C. and the bound proteins were eluted by boiling the beads.

The samples resolved in SDS-PAGE gels were transferred to nitrocellulose and blotted with corresponding primary antibodies followed by HRP-conjugated secondary antibodies. The rabbit polyclonal anti-Kir2.1 antibody was raised against the C-terminal cytoplasmic region corresponding to amino acids 188-428. The immunoblots were developed with the ECL system (Amersham-Pharmacia, Piscataway, N.J.).

The silver staining patterns of cells transfected with different Kir2.1 expression vectors including wild-type, RAA, RKR and RKR-SWTY (SEQ ID NO: 251) were compared. 14-3-3 binding of the two of the eight mutants most effective in abolishing surface expression was measured. The observed reduction of 14-3-3 was further substantiated by immunoblot against 14-3-3.

For blotting of Kir2.1 proteins in the surface fraction, the cells were harvested with EDTA-PBS and incubated with the corresponding antibodies for 20 min at 4° C. in staining medium, washed extensively, and then lysed with 1% NP40 buffer. The supernatant after centrifuge was incubated with protein A-conjugated beads for 5 hour at 4° C and the bound proteins were eluted by boiling the beads. The samples resolved in SDS-PAGE gels were transferred to nitrocellulose and blotted with corresponding primary antibodies followed by HRP-conjugated secondary antibodies. The rabbit polyclonal anti-Kir2.1 antibody was raised against the C-terminal cytoplasmic region corresponding to amino acids 188-428. The immunoblots were developed with the ECL system (Amersham-Pharmacia, Piscataway, N.J.).

When comparing the silver staining patterns of cells transfected with different Kir2.1 expression vectors including wild-type, RAA, RKR and RKR-SWTY (SEQ ID NO: 251), the 14-3-3 species were only detectable in SWTY (SEQ ID NO: 250) transfected cells (FIG. 3C, lanes 1 to 5). The silver staining patterns of the Ala scanning mutants showed differential 14-3-3 intensities correlating with the ability of mutants to bind to 14-3-3 isoforms. Specifically, both FAGRSWTY (SEQ ID NO: 3) and FRGRSWAY (SEQ ID NO: 4) displayed marked reduction of 14-3-3 binding (FIG. 3C, lanes 7 and 12). The reduction of 14-3-3 was further substantiated by immunoblot against 14-3-3, which also showed a reduction (lane 7) and loss of signal (lane 12). The expression level of Kir2.1 remained relatively consistent as shown by immunoblot using anti-HA, arguing against the possibility that any fluctuations of Kir2.1 protein expression were responsible for the differential surface expression and binding to 14-3-3. This result is in agreement with the flow cytometry data, hence establishing the link of surface expression level to efficiency of 14-3-3 binding (FIG. 3B).

D. Interaction between 14-3-3 and SWTY-related motifs (SEQ ID NO: 250): To explore any potentially shared properties in 14-3-3 binding for various isolated clones in Group 2 and 3 (two of the three groups of clones previously found to grow at 4 mM Potassium and conferring some degree of surface expression of Kir2.1-RKR), transient transfection was performed to express a selection of 19 clones from these two groups (FIG. 4A). The anti-HA precipitated materials were fractionated and detected with either anti-Kir2.1 antibody (upper panel) or anti-14-3-3 antibody (lower panel).

The clones found to interact with 14-3-3 (FIG. 4A) possess clearly shared features including Ser or Thr at the -2 position. To determine the potential preference in positioning at -2 for Thr or Ser, a mutated form of Kir2.1-RKR-SWTY (peptide disclosed as SEQ ID NO: 251) was constructed and expressed which has three additional alanines fused to the C-terminus. Flow cytometry analyses were performed to determine the effect of the mutation on SWTY-mediated surface expression (peptide disclosed as SEQ ID NO: 250) (FIG. 4C). To determine whether the phosphorylation of -2 Thr or Ser plays a role, an affinity pull down experiment was carried out using synthetic peptides corresponding to a control sequence (SISPDSLS) (SEQ ID NO: 254), and three forms of the SWTY sequence (SEQ ID NO: 250): RGRSWTY (SEQ ID NO: 1), RGRSWpTY (SEQ ID NO: 255) and RGR-SWpTYAAA (SEQ ID NO: 256). Upon affinity binding with HEK293 cell lysates, the resultant materials after extensive wash were separated by SDS gel and detected by silver staining.

Flow cytometry analyses revealed that adding AAA to the C-terminus of SWTY (SEQ ID NO: 250) abolished SWTY-mediated surface expression (peptide disclosed as SEQ ID NO: 250) (FIG. 4C). To determine whether the phosphorylation of -2 Thr or Ser plays a role, an affinity pull down experiment was carried out using synthetic peptides corresponding to a control sequence (SISPDSLS) (SEQ ID NO: 254), and three forms of the SWTY sequence (SEQ ID NO: 250): RGRSWTY (SEQ ID NO: 1), RGRSWPTY (SEQ ID NO: 255) and RGRSWpTYAAA (SEQ ID NO: 256). Upon affinity binding with HEK293 cell lysates, the resultant materials after extensive wash were separated by SDS gel and detected by silver staining. The results indicate that RGR-SWpTY (SEQ ID NO: 255) was most capable of precipitating the 14-3-3 (FIG. 4D, lane 4). Hence, the phosphorylation at the -2 position of SWTY motif (SEQ ID NO: 250) is important for the 14-3-3 interaction.

Example 4

Regulation of Glycosylation by SWTY Motifs (SEQ ID NO: 250)

A. Surface expression of CD8 proteins: To test the correlation of glycosylation and surface expression level, the SWTY motif (SEQ ID NO: 250) was fused to CD8 antigen, and experiments were performed to determine the distribution of protein expression and extent of CD8 glycosylation via flow cytometry. CD8HA vectors were constructed by replacing the CD4 sequence in CD4(HA) vectors with full-length human CD8a sequence. A mutagenesis of the FRGR-SWTY sequence (SEQ ID NO: 2) in clone#4 was performed by annealing and extending complementary oligonucleotides that contained individual mutations. Native X8 sequences were cloned into a CD8 vector by inserting between SfiI and XhoI sites, following oligo extension by Klenow enzyme.

The transfected HEK293 cells were harvested by incubation with 0.5 mM EDTA-PBS for 10 min at 37° C. and washed with Hanks' Balanced Salt Solution supplemented with 5 mM HEPES (pH 7.3) and 2% FBS (staining medium). All the antibody incubations and washings were performed in staining medium at 4° C. For CD8, mouse anti-human CD8 mAb (Santa Cruz, Santa Cruz, Calif.) was followed by FITC-conjugated goat anti-mouse IgG (Vector Laboratories, Burlingame, CA). The stained cells were examined for surface expression with FACSCalibur (BD Biosciences, San Jose, Calif.).

Flow cytometry analyses showed robust surface expression of wild-type CD8, whereas RKR-fusion essentially abolished the surface expression (FIG. 5A). The RKR-specific effect was again demonstrated by the point mutations of RAA, which did not cause any detectable reduction of surface expression. The lack of further increase of surface expression compared to wildtype by SWTY (SEQ ID NO: 250) is presumably due to the already robust surface expression of CD8, similar to that of CD4 (FIG. 2D).

B. Immunoblot detection of CD8 proteins: Protein expression and potential mobility shift were determined by immunoblot analyses of both total cell lysates and the surface localized receptor immunoprecipitated by anti-CD8 specific for an extracellular epitope.

For blotting of CD8 proteins in the surface fraction, the cells were harvested with EDTA-PBS and incubated with the corresponding antibodies for 20 min at 4° C in staining medium, washed extensively, and then lysed with 1% NP40 buffer. The supernatant after centrifuge was incubated with protein A-conjugated beads for 5 hours at 4° C and the bound proteins were eluted by boiling the beads. The samples resolved in SDS-PAGE gels were transferred to nitrocellulose and blotted with corresponding primary antibodies followed by HRP-conjugated secondary antibodies. The immunoblots were developed with the ECL system (Amersham-Pharmacia, Piscataway, N.J.).

The CD8 protein was compared with either RKR or RAA to determine in what form CD8-RKR and CD8-RAA can be found in the total cell lysates. Similar analyses were performed of CD8-RKR (or RAA) with a fused SWTY motif (SEQ ID NO: 250). CD8 surface expression conferred was also studied for the native C-terminal sequences of KCNK15, KCNK3 and GPCR15, which are homologous to that of SWTY (SEQ ID NO: 250) (FIG. 7), as well as for the other 14-3-3 binding positive sequences (data not shown).

Comparison of the CD8 protein with either RKR or RAA revealed that CD8-RKR can be found only in total lysate in an immature form. In contrast, the majority of CD8-RAA was present in a mature form indicative of glycosylation. Consistently, the mature form was detected by surface immunoprecipitation (FIG. 5B, lanes 1 to 4). The absence of any immature signal detected in CD8-RKR from the cell surface immunoprecipitation indicates the specific recognition of surface receptors by antibody. Performing similar analyses of CD8-RKR (or RAA) with a fused SWTY motif (SEQ ID NO: 250) revealed a substantial reduction of the mature form and an increase of immature form in total lysates, giving rise to a reversed ratio of banding intensity compared to CD8-RAA lacking the SWTY motif (SEQ ID NO: 250) (FIG. 5B, lanes 3 & 5). Furthermore, surface immunoprecipitation revealed almost equal amounts of mature and immature form were precipitated. Comparable ratios of the two forms were obtained from the CD8-RAA-SWTY construct (peptide disclosed as SEQ ID NO: 257) (FIG. 5B, lanes 7 & 8). Provided that the surface expression levels of CD8-RAA, CD8-RKR-SWTY (peptide disclosed as SEQ ID NO: 251), and CD8-RAA-SWTY (peptide disclosed as SEQ ID NO: 257) are essentially identical (FIG. 5A), the evidence supports the SWTY-dependent (peptide disclosed as SEQ ID NO: 250) surface expression of CD8 that possesses no or much reduced O-linked glycosylation. Furthermore, the native C-terminal sequences of KCNK15, KCNK3 and GPCR15, which are homologous to that of SWTY (SEQ ID NO: 250) (FIG. 7), also confer surface expression of CD8 with a substantial reduction of O-glycosylation (FIG. 5B, lanes 9 to 14). Similarly, the other 14-3-3 binding positive sequences in FIG. 4B have the same effects on CD8 glycosylation (data not shown).

C. Co-immunoprecipitation of CD8 proteins with 14-3-3: To determine a potentially causal link between surface expression of immature form and 14-3-3 binding, cells transfected with various CD8 constructs were subjected to immunoprecipitation with anti-14-3-3 antibody. For immunoprecipitation, transfected cells were washed with PBS once and lysed with lysis buffer (1% NP40, 25 mM Tris, 150 mM NaCl, pH 7.50) with protease inhibitor cocktails for 20 min at 4° C. After spinning for 20 min at 11,000 g, the supernatant was mixed with protein A-conjugated agarose beads which were pre-incubated with 1 μg of anti-HA antibody or anti-14-3-3R antibody (Santa Cruz). After 5 hour incubation, the beads were washed 5 times with lysis buffer and then boiled with 2× sample buffer for SDS-PAGE analysis. The precipitated materials were detected with anti-HA antibody reactive to all CD8 fusions as indicated. FIG. 5C shows that anti-14-3-3 antibody only co-precipitated SWTY-fused constructs (peptide disclosed as SEQ ID NO: 250). Furthermore, the mobility of the coprecipitated forms is identical to that of the immature form (FIG. 5C, lanes 4 & 5), demonstrating a selective association of 14-3-3 protein with the immature form of the CD8-SWTY fusions (peptide disclosed as SEQ ID NO: 250).

D. Pulse-chase of CD8 and Kir2.1 proteins with SWTY motif (SEQ ID NO: 250): To assess the stage of biogenesis at which 14-3-3 begins to engage the SWTY-bearing receptor (peptide disclosed as SEQ ID NO: 250), pulse-chase analyses were performed. 24 hour post transfection with CD8 constructs, HEK293 cells were starved for 1 hour at 37° C. in methionine/cysteine-free medium supplemented with 5% dialyzed FBS. Cells transfected with CD8-RAA, CD8-RKR and CD8-RKR-SWTY (peptide disclosed as SEQ ID NO: 251) were pulsed with $S^{35}$-labeled Met and Cys for 10 min and chased at 0 hour, 1 hour and 3 hour. After washing 4 times with cold PBS, the cells were chased at 37° C. in complete medium supplemented with 2 mM methionine and cysteine for indicated times. The cells were then lysed for immunoprecipitation with anti-HA antibody as described above. The precipitated proteins of total lysate were fractionated on SDS-PAGE and recorded by autoradiography.

Two strong bands, which could be different transitional maturation forms of CD8-RKR-SWTY (peptide disclosed as SEQ ID NO: 251), were detectable for CD8-RKR-SWTY (peptide disclosed as SEQ ID NO: 251) immediately after pulse and have mobilities identical to those of 14-3-3. To determine the identities, similar pulse-chase experiments were performed using cells stably expressing Kir2.1 or Kir2.1-RKR-SWTY (peptide disclosed as SEQ ID NO: 251). For pulse-chase of Kir2.1 proteins, the stable Kir2.1 clones for wild type and RKR-SWTY (SEQ ID NO: 251) were cultured overnight with 5 mM Na-butyrate. After pulse for 10 minutes at 37° C. and chase at 37° C. for indicated times, one set of cells were subjected to quantitation of the surface expressed Kir2.1 proteins by incubating with anti-HA antibody first and then precipitating by Protein A beads. The other set of cells were directly lysed and precipitated by Protein A beads pre-bound with anti-HA antibody. The eluated samples were resolved on SDS-PAGE, transferred to nitrocellulose and then analyzed by autoradiography using phosphoimaging system (Fujifilm, Stamford, Conn.).

FIG. 6A shows that while the immature form of CD8-RAA was detectable immediately after pulse, the corresponding mature form could be detected after 1hr. The CD8-RAA was completely matured at 3 hr (FIG. 6A, lanes 1, 4 & 7). In contrast, CD8-RKR was never matured, consistent with intracellular localization and failure of surface expression (FIG. 6A, lanes 2, 5, & 8). Unique to CD8-RKR-SWTY (peptide disclosed as SEQ ID NO: 251), there were two strong bands detectable immediately after the pulse. Over the course of a 3 hour chase, the lower band, which corresponds to the mobility of immature form of CD8-RKR-SWTY (peptide disclosed as SEQ ID NO: 251), became broadened (FIG. 6A, band marked with arrow #3). But the mature form of CD8-RKR-SWTY (peptide disclosed as SEQ ID NO: 251) was barely visible after a 3 hour chase (FIG. 6A, lanes 3, 6 & 9; marked with arrow #1). Because the surface expression levels of CD8-

RAA and CD8-RKR-SWTY (peptide disclosed as SEQ ID NO: 251) are essentially identical (FIG. 5A), this evidence provides further support for the notion that the immature form of CD8-RKR-SWTY (peptide disclosed as SEQ ID NO: 251) was able to express on the cell surface. The two strong bands, which could be different transitional maturation forms of CD8-RKR-SWTY (peptide disclosed as SEQ ID NO: 251), have mobilities identical to those of 14-3-3. To determine the identities, similar pulse-chase experiments were performed using cells stably expressing Kir2.1 or Kir2.1-RKR-SWTY (peptide disclosed as SEQ ID NO: 251). Similar to the results obtained from the CD8 experiments (FIG. 6A, e.g., lane 3), the two bands were again observed immediately after the pulse, and their presence persisted over the course of a 3 hr chase (FIG. 6B, lanes 7 to 12). In contrast, the two bands were absent in Kir2.1 transfected cells, demonstrating SWTY-dependence (peptide disclosed as SEQ ID NO: 250). Considering the banding intensity/ratio (also see Discussion) and the immunoprecipitation results shown in FIG. 3A, these two bands are most likely the 14-3-3 isoforms. Because no mature form of CD8 was detectable at 0 hr when the 14-3-3 had already bound to CD8-RKR-SWTY (peptide disclosed as SEQ ID NO: 251) (FIG. 6A, lanes 1 & 3), association of SWTY-bearing receptor (peptide disclosed as SEQ ID NO: 250) with 14-3-3 is likely to take place prior to trafficking to Golgi.

To determine whether the surfaced Kir2.1-RKR-SWTY (peptide disclosed as SEQ ID NO: 251) is associated with 14-3-3, the surfaced Kir2.1 and Kir2.1-RKR-SWTY (peptide disclosed as SEQ ID NO: 251) were selectively precipitated under the pulse-chased conditions. The specific co-immunoprecipitation of 14-3-3 from surfaced Kir2.1-RKR-SWTY (peptide disclosed as SEQ ID NO: 251) transfected cells (lanes 4-6) vs. from Kir2.1 transfected cells (lanes 1-3) was investigated. The ratio of surface receptor was compared with total receptor.

FIG. 6C shows the specific coimmunoprecipitation of 14-3-3 only from surfaced Kir2.1-RKR-SWTY (peptide disclosed as SEQ ID NO: 251) transfected cells (lanes 4-6) but not from Kir2.1 transfected cells (lanes 1-3). These results show that the interaction between SWTY motif (SEQ ID NO: 250) and 14-3-3 established early in biogenesis is also detectable in surfaced Kir2.1 channels. Comparison of the ratio of surface receptor vs. total receptor revealed a more than four-fold improvement conferred by the SWTY motif (SEQ ID NO: 250) (FIG. 6D). While the rates of reaching to cell surface were comparable, the signal of Kir2.1-RKR-SWTY (peptide disclosed as SEQ ID NO: 251) was considerably stronger in an extended chase period than that of Kir2.1. These data and the steady state expression analyses support the notion that SWTY (SEQ ID NO: 250) is capable of prolonging the protein half-life on cell surface.

Example 5

SWTY Motifs (SEQ ID NO: 250) in Native Proteins

A. Native SWTY-like sequences: The combination of sequence information, mutagenesis and association with 14-3-3 proteins permits examination of native proteins with SWTY-like sequences (peptide disclosed as SEQ ID NO: 250). For Human (*Homo sapiens*), Mouse (*Mus musculus*), Rat (*Rattus norvegicus*), Worm (*Caenorhabditis elegans*), and Yeast (*Saccharomyces cerevisiae*), NCBI RefSeq protein databases (curated, non-redundant sets including mRNAs and proteins for known genes and for gene models) were downloaded, and searched with a program written in PERL for desired characteristics. Membrane proteins were selected by requiring that the protein names include one of the following keywords: receptor, transporter, transmembrane, membrane, channel, or pore. Bioinformatics analyses were performed to search for proteins with C-termini matching the following criteria: (1) membrane bound, (2) a Ser or Thr at the -2 position, and (3) a positively charged residue at the -4 and/or -5 position. For the Fly (*Drosophila melanogaster*) proteome, proteins annotated as plasma membrane localized by Flybase (http://flybase.bio.indiana.edu/annot/fbann-query.hform) were manually searched for the criteria used with the other organisms (excepting the membrane keyword criterion).

To experimentally demonstrate the activity of the native sequences to override ER localization signal, thereby reaching the cell surface, the CD8 antigen was selected as reporter protein fused with an HA tag and an RKR ER localization motif (FIG. 7B). A list of shown native sequences were tested for surface expression of CD8 by flow cytometry and for 14-3-3 binding by co-immunoprecipitation. The diverse group included human, *C. elegans* and yeast proteins including three potassium channels (KCNK3, KCNK9 and KCNK15) (human), a membrane associated cytosolic protein (BASP-like protein in mouse), a G-protein coupled receptor (GPCR) (human), a novel tetraspan protein (*C. elegans*), and a yeast protein, Ant1p. The CD8 fusion proteins with these sequences were expressed. The flow cytometry analyses were used to determine their ability to overcome ER localization.

B. SWTY-like sequences (peptide disclosed as SEQ ID NO: 250) in action: To test the activity of SWTY-like sequence (peptide disclosed as SEQ ID NO: 250) in the native context, two markedly different proteins: KCNK3, a potassium channel important for controlling membrane potential (Lopes et al., 2000) and GPR15, a G-protein coupled receptor that is a co-receptor for HIV (Maresca et al., 2003; Wade-Evans et al., 2001) were selected. Rat KCNK3 was cloned by PCR into pcDNA3(+) at HindIII and NotI with HA epitope inserted at the position 213 of KCNK3. Human GPR15 was cloned by PCR into pEMV vector at SalI and NotI with HA epitope at the N-terminus.

Flow cytometry after antibody binding was used to detect surface expression resulting from transient expression of wild-type KCNK3 and GRP15 in cultured HEK 293 cells. The transfected HEK293 cells were harvested by incubation with 0.5 mM EDTA-PBS for 10 min at 37° C. and washed with Hanks' Balanced Salt Solution supplemented with 5 mM HEPES (pH 7.3) and 2% FBS (staining medium). All the antibody incubations and washings were performed in staining medium at 4° C. For HA-KCNK3 and HA-GPR15, mouse anti-HA antibodies (Santa Cruz, Santa Cruz, Calif.) binding was detected by AlexaFluor488-conjugated goat anti-mouse IgG (Molecular Probes, Eugene, Oreg.). The stained cells were examined for surface expression with FACSCalibur (BD Biosciences, San Jose, Calif.). Similar analyses were performed upon introduction of point mutations at the C-terminus, S410A for KCNK3, and S259A for GPR15. The localization of KCNK3 and GPR15 proteins was further examined by confocal microscopy.

These two proteins have SWTY-like sequences (peptide disclosed as SEQ ID NO: 250) (FIG. 7B) and transient expression of wild-type KCNK3 and GRP15 in cultured HEK 293 cells resulted in surface expression readily detected by flow cytometry after antibody binding. When point mutations were introduced at the C-terminus, S410A for KCNK3, and S259A for GPR15, considerable reductions of surface expression were detected by flow cytometry (FIG. 8A, upper panels). The localization of KCNK3 and GPR15 proteins was further examined by confocal microscopy. The wild-type proteins were found on the cell surface. In contrast, the mutant proteins displayed a significant accumulation in intracellular compartments. The surface expression of KCNK3-S410A or GPR15-S256A was not detectable (FIG. 8A, lower panels).

C. Conservation of SWTY (SEQ ID NO: 250) function: To determine whether SWTY (SEQ ID NO: 250) functions comparably in KCNK3 and GPR15 proteins, chimeric KCNK3 or GPR15 proteins were tested that were constructed by replacing the C-termini with either RGRSWTY (SEQ ID NO: 1) or RGRSWAY (SEQ ID NO: 259). Comparison of 14-3-3 binding to the wild type and chimeric proteins was carried out using co-immunoprecipitation with anti-HA antibody specific to the tagged KCNK3 and GPR15. The chimeric channel and receptor proteins were then tested for surface expression. Capability of rescuing the surface expression of both KCNK3 and GPR15 was tested for SWTY (SEQ ID NO: 250) and SWAY (SEQ ID NO: 264).

The specific association of 14-3-3 proteins was detected with the wild type KCNK3 and GPR15 but not the C-terminally mutated forms (FIG. 8B, lanes 2 and 3). Similarly, the 14-3-3 proteins were specifically co-immunoprecipitated with SWTY (SEQ ID NO: 250) chimera but not SWAY (SEQ ID NO: 264) chimera (FIG. 8B, lanes 4 and 5). The chimeric channel and receptor proteins were then tested for surface expression. FIG. 8C shows, SWTY (SEQ ID NO: 250), but not SWAY (SEQ ID NO: 264), was capable of rescuing the surface expression of both KCNK3 and GPR15. These results show that the de novo isolated RGRSWTY (SEQ ID NO: 1) is mechanistically equivalent to the two C-terminal sequences of KCNK3 (LMKKRRSSV) (SEQ ID NO: 265) and GPR15 (RRKRSVSL) (SEQ ID NO: 14). Furthermore, these experiments, using two markedly different native proteins, provide direct evidence linking sequence, to phosphorylation, to 14-3-3 binding and then to surface expression.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended numbered claims.

REFERENCES

Bonifacino, J. S., and Glick, B. S. (2004). The mechanisms of vesicle budding and fusion. Cell 116, 153-166.

Bruckner, K., Perez, L., Clausen, H., and Cohen, S. (2000). Glycosyltransferase activity of Fringe modulates Notch-Delta interactions. Nature 406, 411-415.

Chung, J. J., Shikano, S., Hanyu, Y., and Li, M. (2002). Functional diversity of protein C-termini: more than zip-coding? Trends Cell Biol 12, 146-150.

Chung, J. J., Yang, H., and Li, M. (2003). Genome-wide Analyses of Carboxyl-terminal Sequences. Mol Cell Proteomics 2, 173-181.

Clark, K. L., Oelke, A., Johnson, M. E., Eilert, K. D., Simpson, P. C., and Todd, S. C. (2004). CD81 associates with 14-3-3 in a redox-regulated palmitoylation-dependent manner. J Biol Chem 279, 19401-19406.

Ellgaard, L., and Helenius, A. (2003). Quality control in the endoplasmic reticulum. Nat Rev Mol Cell Biol 4, 181-191.

Fu, H., Subramanian, R. R., and Masters, S. C. (2000). 14-3-3 proteins: structure, function, and regulation. Annu Rev Pharmacol Toxicol 40, 617-647.

Jackson, M. R., Nilsson, T., and Peterson, P. A. (1993). Retrieval of transmembrane proteins to the endoplasmic reticulum. J Cell Biol 121, 317-333.

Klausner, R. D., and Sitia, R. (1990). Protein degradation in the endoplasmic reticulum. Cell 62, 611-614.

Lopes, C. M., Gallagher, P. G., Buck, M. E., Butler, M. H., and Goldstein, S. A. (2000). Proton block and voltage gating are potassium-dependent in the cardiac leak channel Kcnk3. J Biol Chem 275, 16969-16978.

Ma, D., Zerangue, N., Lin, Y. F., Collins, A., Yu, M., Jan, Y. N., and Jan, L. Y. (2001). Role of ER export signals in controlling surface potassium channel numbers. Science 291, 316-319.

Ma, D., Zerangue, N., Raab-Graham, K., Fried, S. R., Jan, Y. N., and Jan, L. Y. (2002). Diverse trafficking patterns due to multiple traffic motifs in G protein-activated inwardly rectifying potassium channels from brain and heart. Neuron 33, 715-729.

Maresca, M., Mahfoud, R., Garmy, N., Kotler, D. P., Fantini, J., and Clayton, F. (2003). The virotoxin model of HIV-1 enteropathy: involvement of 37 GPR15/Bob and galactosylceramide in the cytopathic effects induced by HIV-1 gp 120 in the HT-29-D4 intestinal cell line. J Biomed Sci 10, 156-166.

Mellman, I., and Warren, G. (2000). The road taken: past and future foundations of membrane traffic. Cell 100, 99-112.

Miller, E. A., Beilharz, T. H., Malkus, P. N., Lee, M. C., Hamamoto, S., Orci, L., and Schekman, R. (2003). Multiple cargo binding sites on the COPII subunit Sec24p ensure capture of diverse membrane proteins into transport vesicles. Cell 114, 497-509.

Moore, B., and Perez, V. J. (1967). Specific acidic proteins of the nervous system, Prentice-Hall, Englewood Cliffs, N.J.).

Mossessova, E., Bickford, L. C., and Goldberg, J. (2003). SNARE selectivity of the COPII coat. Cell 114, 483-495.

Nilsson, T., Hoe, M. H., Slusarewicz, P., Rabouille, C., Watson, R., Hunte, F., Watzele, G., Berger, E. G., and Warren, G. (1994). Kin recognition between medial Golgi enzymes in HeLa cells. Embo J 13, 562-574.

Nilsson, T., Jackson, M., and Peterson, P. A. (1989). Short cytoplasmic sequences serve as retention signals for transmembrane proteins in the endoplasmic reticulum. Cell 58, 707-718.

Nishimura, N., and Balch, W. E. (1997). A di-acidic signal required for selective export from the endoplasmic reticulum. Science 277, 556-558.

Nufer, O., and Hauri, H. P. (2003). ER export: call 14-3-3. Curr Biol 13, R391-393.

O'Kelly, I., Butler, M. H., Zilberberg, N., and Goldstein, S. A. (2002). Forward transport. 14-3-3 binding overcomes retention in endoplasmic reticulum by dibasic signals. Cell 111, 577-588.

Rothman, J. E., and Wieland, F. T. (1996). Protein sorting by transport vesicles. Science 272, 227-234.

Rubio, M. P., Geraghty, K. M., Wong, B. H., Wood, N. T., Campbell, D. G., Morrice, N., and Mackintosh, C. (2004). 14-3-3-affinity purification of over 200 human phosphoproteins reveals new links to regulation of cellular metabolism, proliferation and trafficking. Biochem J 379, 395-408.

Schroer, T. A. (2000). Motors, clutches and brakes for membrane traffic: a commemorative review in honor of Thomas Kreis. Traffic 1, 3-10.

Schwappach, B., Zerangue, N., Jan, Y. N., and Jan, L. Y. (2000). Molecular basis for K(ATP) assembly: transmembrane interactions mediate association of a K+ channel with an ABC transporter. Neuron 26, 155-167.

Shikano, S., and Li, M. (2003). Membrane receptor trafficking: Evidence of proximal and distal zones conferred by two independent endoplasmic reticulum localization signals. Proc Natl Acad Sci USA 100, 5783-5788.

Snider, M. D., and Rogers, 0. C. (1985). Intracellular movement of cell surface receptors after endocytosis: resialylation of asialo-transferrin receptor in human erythroleukemia cells. J Cell Biol 100, 826-834.

Tang, W., Ruknudin, A., Yang, W. P., Shaw, S. Y., Knickerbocker, A., and Kurtz, S. (1995). Functional expression of a vertebrate inwardly rectifying K+ channel in yeast. Mol Biol Cell 6, 1231-1240.

Wade-Evans, A. M., Russell, J., Jenkins, A., and Javan, C. (2001). Cloning and sequencing of cynomolgus macaque CCR3, GPR15, and STRL33: potential coreceptors for HIV type 1, HIV type 2, and SIV. AIDS Res Hum Retroviruses 17, 371-375.

Wallin, E., and von Heijne, G. (1998). Genome-wide analysis of integral membrane proteins from eubacterial, archaean, and eukaryotic organisms. Protein Sci 7, 1029-1038.

Wurtele, M., Jelich-Ottmann, C., Wittinghofer, A., and Oecking, C. (2003). Structural view of a fungal toxin acting on a 14-3-3 regulatory complex. Embo J 22, 987-994.

Yaffe, M. B. (2002). How do 14-3-3 proteins work?—Gatekeeper phosphorylation and the molecular anvil hypothesis. FEBS Lett 513, 53-57.

Yang, J., Jan, Y. N., and Jan, L. Y. (1995). Determination of the subunit stoichiometry of an inwardly rectifying potassium channel. Neuron 15, 1441-1447.

Yuan, H., Michelsen, K., and Schwappach, B. (2003). 14-3-3 dimers probe the assembly status of multimeric membrane proteins. Curr Biol 13, 638-646.

Zerangue, N., Schwappach, B., Jan, Y. N., and Jan, L. Y. (1999). A new ER trafficking signal regulates the subunit stoichiometry of plasma membrane K(ATP) channels. Neuron 22, 537-548.

The invention claimed is:

1. A recombinant polynucleotide that encodes a cell surface polypeptide comprising a biomolecule partition motif, wherein the biomolecule partition motif comprises the amino acid sequence of SEQ ID NO: 250 and is located at the carboxy terminus of said polypeptide.

2. The recombinant polynucleotide of claim 1, wherein the polynucleotide is a DNA molecule.

3. The recombinant polynucleotide of claim 1, wherein the polynucleotide is an RNA molecule.

4. A recombinant polynucleotide comprising an RNA molecule that is complementary to the RNA molecule of claim 3.

5. The recombinant polynucleotide of claim 1, wherein the biomolecule partition motif is SEQ ID NO: 1 (RKRSWTY).

6. An expression vector comprising a recombinant polynucleotide that encodes a cell surface polypeptide comprising a biomolecule partition motif, wherein the biomolecule partition motif comprises the amino acid sequence of SEQ ID NO: 250 and is located at the carboxy terminus of said polypeptide.

7. The expression vector of claim 6, wherein the recombinant polynucleotide is operatively linked to an enhancer and/or promoter.

8. A transformed cell comprising the recombinant polynucleotide of claim 1.

9. A process for preparing a transformed cell, the process comprising the steps of:
- a) transfecting, electroporating or transforming the cell with a recombinant polynucleotide that encodes a cell surface polypeptide comprising a biomolecule partition motif, wherein the biomolecule partition motif comprises the amino acid sequence of SEQ ID NO: 250 and is located at the carboxy terminus of said polypeptide; and
- b) maintaining the cell of step a) under conditions sufficient for expression of the polypeptide of step a).

10. A transformed cell comprising a recombinant cell surface polypeptide, wherein the recombinant cell surface polypeptide comprises a biomolecule partition motif, wherein the biomolecule partition motif comprises the amino acid sequence of SEQ ID NO: 250 and is located at the carboxy terminus of said polypeptide, and wherein the biomolecule partition motif is not present in the native polypeptide.

11. A method of obtaining a polypeptide from the surface of a cell, the method comprising:
- expressing a polypeptide having at least one biomolecule partition motif in a cell under conditions sufficient to provide the polypeptide to the surface of the cell, wherein the biomolecule partition motif comprises the amino acid sequence of SEQ ID NO: 250 and is located at the carboxy terminus of said polypeptide; and
- isolating the polypeptide, thereby obtaining the polypeptide from the surface of the cell.

12. The method of claim 11, wherein the biomolecule partition motif is SEQ ID NO: 1 (RKRSWTY).

* * * * *

SEQUENCE LISTING

```
<160> NUMBER OF SEQ ID NOS: 332

<210> SEQ ID NO 1
<211> LENGTH: 7
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 1

Arg Gly Arg Ser Trp Thr Tyr
 1               5

<210> SEQ ID NO 2
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 2

Phe Arg Gly Arg Ser Trp Thr Tyr
 1               5

<210> SEQ ID NO 3
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 3

Phe Ala Gly Arg Ser Trp Thr Tyr
 1               5

<210> SEQ ID NO 4
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif
```

-continued

```
<400> SEQUENCE: 4

Phe Arg Gly Arg Ser Trp Ala Tyr
 1               5

<210> SEQ ID NO 5
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 5

Phe Arg Gly Ala Ser Trp Thr Tyr
 1               5

<210> SEQ ID NO 6
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 6

Arg Leu Arg Arg Gly Trp Thr Val
 1               5

<210> SEQ ID NO 7
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 7

Gly His Gly Arg Arg His Ser Trp
 1               5

<210> SEQ ID NO 8
<211> LENGTH: 5
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 8

Arg Arg Lys Thr Val
 1               5

<210> SEQ ID NO 9
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 9

Leu Val Arg Arg Ser Ile Thr Phe
 1               5
```

```
<210> SEQ ID NO 10
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 10

Ser Arg Asp Arg Arg Lys Thr Tyr
 1               5

<210> SEQ ID NO 11
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 11

Leu Met Lys Arg Arg Ser Ser Val
 1               5

<210> SEQ ID NO 12
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 12

Leu Met Lys Arg Arg Lys Ser Val
 1               5

<210> SEQ ID NO 13
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 13

Leu Arg Ala Arg Arg Lys Ser Ile
 1               5

<210> SEQ ID NO 14
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 14

Arg Arg Lys Arg Ser Val Ser Leu
 1               5

<210> SEQ ID NO 15
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 15

Glu Arg His Arg Arg Trp Ser Ser
  1               5

<210> SEQ ID NO 16
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 16

Glu His Arg Ser Arg Asn Thr Leu
  1               5

<210> SEQ ID NO 17
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 17

Lys Leu Arg Arg Arg Lys Thr Leu
  1               5

<210> SEQ ID NO 18
<211> LENGTH: 8
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 18

Gly Gln Arg Lys Leu Ala Ser Thr
  1               5

<210> SEQ ID NO 19
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 19

Gln Arg Ser Ile Trp Gly Lys Lys Ser Gln
  1               5                  10

<210> SEQ ID NO 20
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 20

Phe Leu Gly Lys Lys Lys Thr Lys Thr Asp
  1               5                  10
```

```
<210> SEQ ID NO 21
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 21

Lys Ala Asn Ile Pro Lys Ala Lys Ser Ala
 1               5                  10

<210> SEQ ID NO 22
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 22

Ile Lys Lys Asn Asp Leu Lys Lys Ser Asn
 1               5                  10

<210> SEQ ID NO 23
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 23

Asn Ile Asp Ala Leu Leu Lys Lys Thr Glu
 1               5                  10

<210> SEQ ID NO 24
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 24

Asn Ile Asp Ala Leu Leu Lys Lys Thr Glu
 1               5                  10

<210> SEQ ID NO 25
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 25

Lys Lys Asn Lys Lys Arg Lys Phe Thr Lys
 1               5                  10

<210> SEQ ID NO 26
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 26

Leu Pro Trp Lys Arg Lys Lys Thr Thr Ile
  1               5                  10

<210> SEQ ID NO 27
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 27

Lys Val Val Glu Lys Ala Lys Tyr Ser Leu
  1               5                  10

<210> SEQ ID NO 28
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 28

Arg Arg Leu Gln Pro Ala Lys Ser Thr Phe
  1               5                  10

<210> SEQ ID NO 29
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 29

Arg Arg Leu Gln Pro Ala Lys Ser Thr Phe
  1               5                  10

<210> SEQ ID NO 30
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 30

Ile Lys Lys Leu Trp Cys Lys Thr Ser Ala
  1               5                  10

<210> SEQ ID NO 31
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 31

Ile Lys Lys Leu Trp Cys Lys Thr Ser Ala
  1               5                  10
```

```
<210> SEQ ID NO 32
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 32

Pro Tyr Val Cys Lys Cys Lys Leu Thr Asn
 1               5                  10

<210> SEQ ID NO 33
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 33

Thr Tyr Val Cys Lys Cys Lys Phe Thr Asn
 1               5                  10

<210> SEQ ID NO 34
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 34

Ile Lys Leu Leu Asn Glu Lys Lys Thr Ser
 1               5                  10

<210> SEQ ID NO 35
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 35

Gly Arg Arg Arg Gly Gly Lys Ala Thr Thr
 1               5                  10

<210> SEQ ID NO 36
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 36

Lys Lys Ile Leu Gly Gly Lys Cys Ser Gln
 1               5                  10

<210> SEQ ID NO 37
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 37

Glu Thr Leu Cys Arg Lys Lys Leu Ser Gly
 1               5                  10

<210> SEQ ID NO 38
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 38

Phe Gly Lys Gly Thr Lys Lys Thr Ser His
 1               5                  10

<210> SEQ ID NO 39
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 39

Phe Lys Lys Met Val Lys Lys Ser Thr Leu
 1               5                  10

<210> SEQ ID NO 40
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 40

Ile Lys Lys Cys Thr Lys Asp Thr Ser Lys
 1               5                  10

<210> SEQ ID NO 41
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 41

Ile Lys Lys Cys Thr Lys Asp Thr Ser Lys
 1               5                  10

<210> SEQ ID NO 42
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 42

Ile Lys Lys Cys Thr Lys Asp Thr Ser Lys
 1               5                  10
```

```
<210> SEQ ID NO 43
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 43

Ile Lys Lys Cys Thr Lys Asp Thr Ser Lys
 1               5                  10

<210> SEQ ID NO 44
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 44

Ile Lys Val Leu Ile Lys Lys Ile Ser Leu
 1               5                  10

<210> SEQ ID NO 45
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 45

Ile Lys Val Leu Ile Lys Lys Ile Ser Leu
 1               5                  10

<210> SEQ ID NO 46
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 46

Lys Lys Leu Trp Ser Lys Thr Leu Thr Lys
 1               5                  10

<210> SEQ ID NO 47
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 47

Lys Lys Leu Trp Ser Lys Thr Leu Thr Lys
 1               5                  10

<210> SEQ ID NO 48
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 48

Arg Ile Leu Tyr Lys Lys Lys Ile Ser Leu
 1               5                  10

<210> SEQ ID NO 49
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 49

Arg Met Ile Lys Arg Lys Ile Leu Ser Gln
 1               5                  10

<210> SEQ ID NO 50
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 50

Arg Val Ile Cys Thr Lys Lys Ile Ser Leu
 1               5                  10

<210> SEQ ID NO 51
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 51

Arg Val Ile Cys Thr Lys Lys Ile Ser Leu
 1               5                  10

<210> SEQ ID NO 52
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 52

Arg Val Leu Cys Lys Lys Lys Ile Thr Met
 1               5                  10

<210> SEQ ID NO 53
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 53

Arg Val Leu Cys Lys Lys Asn Ile Ser Leu
 1               5                  10
```

```
<210> SEQ ID NO 54
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 54

Arg Val Leu Cys Lys Lys Gln Ile Ser Leu
 1               5                  10

<210> SEQ ID NO 55
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 55

Arg Val Leu Phe Lys Lys Lys Ile Ser Leu
 1               5                  10

<210> SEQ ID NO 56
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 56

Arg Val Leu Ile Lys Lys Lys Ile Ser Leu
 1               5                  10

<210> SEQ ID NO 57
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 57

Arg Val Leu Ile Lys Lys Lys Ile Ser Leu
 1               5                  10

<210> SEQ ID NO 58
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 58

Arg Val Leu Tyr Lys Lys Lys Ile Ser Leu
 1               5                  10

<210> SEQ ID NO 59
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 59

Arg Val Leu Tyr Lys Lys Ile Ser Leu
 1               5                10

<210> SEQ ID NO 60
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 60

Thr Leu Leu Cys Arg Lys Lys Ser Ser Leu
 1               5                  10

<210> SEQ ID NO 61
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 61

Thr Leu Leu Cys Arg Lys Lys Ser Ser Leu
 1               5                  10

<210> SEQ ID NO 62
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 62

Val Lys Lys Thr Leu Lys Arg Ile Thr Ser
 1               5                  10

<210> SEQ ID NO 63
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 63

Val Lys Lys Thr Leu Lys Arg Ile Thr Ser
 1               5                  10

<210> SEQ ID NO 64
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 64

Val Lys Lys Thr Leu Lys Arg Ile Thr Ser
 1               5                  10
```

```
<210> SEQ ID NO 65
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 65

Val Lys Lys Thr Leu Lys Arg Ile Thr Ser
 1               5                  10

<210> SEQ ID NO 66
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 66

Val Lys Lys Thr Met Lys Arg Ile Thr Ser
 1               5                  10

<210> SEQ ID NO 67
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 67

Val Lys Lys Thr Met Lys Arg Ile Thr Ser
 1               5                  10

<210> SEQ ID NO 68
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 68

Val Met Ala Met Val Lys Arg Lys Ser Ser
 1               5                  10

<210> SEQ ID NO 69
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 69

Ser Ala Lys Lys Met Leu Lys Ile Ser Val
 1               5                  10

<210> SEQ ID NO 70
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 70

Ser Ala Lys Lys Met Leu Lys Ile Ser Val
1               5                   10

<210> SEQ ID NO 71
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 71

Ser Leu Lys Lys Met Leu Lys Ile Thr Ile
1               5                   10

<210> SEQ ID NO 72
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 72

Ser Leu Lys Lys Met Leu Lys Ile Thr Ile
1               5                   10

<210> SEQ ID NO 73
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 73

Lys Lys Ser Leu Arg Asn Arg Ile Ser Ile
1               5                   10

<210> SEQ ID NO 74
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 74

Lys Lys Ser Leu Arg Asn Arg Ile Ser Ile
1               5                   10

<210> SEQ ID NO 75
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 75

Arg Asn Arg Pro Trp Pro Lys Asp Ser Tyr
1               5                   10
```

```
<210> SEQ ID NO 76
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 76

Asp Lys Asn Leu Arg Gln Arg Asn Thr Asn
 1               5                  10

<210> SEQ ID NO 77
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 77

Leu Lys Arg Ser Arg Gln Arg Phe Ser Ser
 1               5                  10

<210> SEQ ID NO 78
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 78

Ala Cys Glu Arg Lys Arg Asp Ile Thr Tyr
 1               5                  10

<210> SEQ ID NO 79
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 79

Ala Val Gln Ser Lys Arg Arg Lys Ser Lys
 1               5                  10

<210> SEQ ID NO 80
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 80

Asp Ile Ser Arg Arg Arg Lys Leu Thr Lys
 1               5                  10

<210> SEQ ID NO 81
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 81

Asp Ile Ser Arg Arg Arg Lys Leu Thr Lys
 1               5                   10

<210> SEQ ID NO 82
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 82

Asp Arg Leu Arg Ala Arg Arg Lys Ser Ile
 1               5                   10

<210> SEQ ID NO 83
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 83

Glu Phe Ser Arg Gly Arg Lys Leu Thr Lys
 1               5                   10

<210> SEQ ID NO 84
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 84

Glu Arg Arg Leu Gln Arg Gln Gln Thr Thr
 1               5                   10

<210> SEQ ID NO 85
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 85

His Ile Leu Arg Arg Arg Leu Phe Ser Gln
 1               5                   10

<210> SEQ ID NO 86
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 86

His Arg Leu His Ile Arg Arg Lys Ser Ile
 1               5                   10
```

```
<210> SEQ ID NO 87
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 87

Lys Gly Ala Leu Arg Arg Ile Met Ser Arg
 1               5                  10

<210> SEQ ID NO 88
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 88

Lys Gly Ala Leu Arg Arg Ile Met Ser Arg
 1               5                  10

<210> SEQ ID NO 89
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 89

Lys Gly Ala Leu Arg Arg Ile Thr Thr Lys
 1               5                  10

<210> SEQ ID NO 90
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 90

Lys Gly Ala Leu Arg Arg Ile Thr Thr Lys
 1               5                  10

<210> SEQ ID NO 91
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 91

Lys Lys Leu Ile Cys Arg Val Ala Ser Leu
 1               5                  10

<210> SEQ ID NO 92
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 92

Leu Leu Phe His Arg Arg Ile Leu Ser Ser
 1               5                  10

<210> SEQ ID NO 93
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 93

Leu Leu Ser His Arg Arg Ile Leu Ser Ser
 1               5                  10

<210> SEQ ID NO 94
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 94

Leu Leu Ser His Arg Arg Ile Leu Ser Ser
 1               5                  10

<210> SEQ ID NO 95
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 95

Met Lys Lys Leu Trp Arg Lys Cys Ser Ser
 1               5                  10

<210> SEQ ID NO 96
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 96

Met Lys Lys Leu Trp Arg Lys Cys Ser Ser
 1               5                  10

<210> SEQ ID NO 97
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 97

Asn Ile Phe Ser Arg Arg Leu Cys Ser Gln
 1               5                  10
```

```
<210> SEQ ID NO 98
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 98

Asn Ile Leu Ser Arg Arg Leu Cys Ser Gln
 1               5                  10

<210> SEQ ID NO 99
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 99

Asn Ile Leu Ser Arg Arg Leu Cys Ser Gln
 1               5                  10

<210> SEQ ID NO 100
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 100

Asn Ile Leu Ser Arg Arg Leu Cys Ser Gln
 1               5                  10

<210> SEQ ID NO 101
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 101

Asn Thr Leu Ser Arg Arg Leu Cys Ser His
 1               5                  10

<210> SEQ ID NO 102
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 102

Gln Asp Tyr Thr Arg Arg Cys Gly Thr Thr
 1               5                  10

<210> SEQ ID NO 103
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 103

Arg Gly Leu Met Lys Arg Arg Ser Ser Val
 1               5                  10

<210> SEQ ID NO 104
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 104

Val Lys Leu Ile Arg Arg Lys Ile Ser Ser
 1               5                  10

<210> SEQ ID NO 105
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 105

Val Lys Arg Arg Lys Arg Ser Val Ser Leu
 1               5                  10

<210> SEQ ID NO 106
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 106

Val Lys Arg Thr Met Arg Arg Ile Thr Met
 1               5                  10

<210> SEQ ID NO 107
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 107

Val Lys Arg Thr Met Arg Arg Ile Thr Met
 1               5                  10

<210> SEQ ID NO 108
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 108

Gly Arg Arg Gly Gly Ser Arg Leu Thr Glu
 1               5                  10
```

```
<210> SEQ ID NO 109
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 109

His Arg Trp Arg Lys Ser Arg Arg Thr Ile
 1               5                  10

<210> SEQ ID NO 110
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 110

Arg Tyr Lys Lys Ser Thr Arg Val Thr Phe
 1               5                  10

<210> SEQ ID NO 111
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 111

Ser Lys Val Gln Lys Thr Lys Asn Thr Thr
 1               5                  10

<210> SEQ ID NO 112
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 112

Ser Lys Val Gln Lys Thr Lys Asn Thr Thr
 1               5                  10

<210> SEQ ID NO 113
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 113

Lys Phe Cys Lys Gly Lys Thr Pro Ser Cys
 1               5                  10

<210> SEQ ID NO 114
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

-continued

```
<400> SEQUENCE: 114

Ser Thr Pro Gly Arg Ser Arg Asn Ser Leu
1               5                   10

<210> SEQ ID NO 115
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 115

Phe Leu Val Phe Arg Asp Arg Val Ser Leu
1               5                   10

<210> SEQ ID NO 116
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 116

Lys Phe Ile Gly Arg Glu Arg Arg Thr Ser
1               5                   10

<210> SEQ ID NO 117
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 117

Asn Met Val Asn Lys His Lys Phe Ser His
1               5                   10

<210> SEQ ID NO 118
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 118

Asp Leu Val Arg Arg Lys Leu Ala Ser Lys
1               5                   10

<210> SEQ ID NO 119
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 119

Asp Leu Val Arg Arg Lys Leu Ala Ser Lys
1               5                   10
```

```
<210> SEQ ID NO 120
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 120

Gly Val Leu Gly Lys Lys Ile Ser Leu
 1               5                  10

<210> SEQ ID NO 121
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 121

His Arg Ala Leu Gln Lys Lys Arg Ser Val
 1               5                  10

<210> SEQ ID NO 122
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 122

Lys Lys Leu Trp Cys Lys Thr Leu Thr Thr
 1               5                  10

<210> SEQ ID NO 123
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 123

Lys Arg Gln Leu Gly Lys Lys Met Ser Cys
 1               5                  10

<210> SEQ ID NO 124
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 124

Lys Arg Gln Leu Gly Lys Lys Met Ser Cys
 1               5                  10

<210> SEQ ID NO 125
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 125

Lys Val Ile Ala Lys Lys Phe Leu Thr Lys
  1               5                  10

<210> SEQ ID NO 126
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 126

Met Lys Lys Ser Trp Lys Arg Ile Thr Ser
  1               5                  10

<210> SEQ ID NO 127
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 127

Met Lys Lys Ser Trp Lys Arg Ile Thr Ser
  1               5                  10

<210> SEQ ID NO 128
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 128

Asn Ala Leu Thr Ile Lys Lys Glu Ser Glu
  1               5                  10

<210> SEQ ID NO 129
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 129

Asn Leu Phe Ser Cys Lys Lys Gly Ser Ile
  1               5                  10

<210> SEQ ID NO 130
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 130

Asn Ser Thr Gly Lys Lys Ile Leu Ser Arg
  1               5                  10
```

```
<210> SEQ ID NO 131
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 131

Pro Gln Lys Ser Lys Lys Asp Arg Thr Gln
 1               5                  10

<210> SEQ ID NO 132
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 132

Arg Ile Ile Gly Ser Lys Lys Ile Ser Leu
 1               5                  10

<210> SEQ ID NO 133
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 133

Arg Arg Ser Leu Leu Lys Glu Arg Ser Met
 1               5                  10

<210> SEQ ID NO 134
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 134

Arg Arg Ser Leu Leu Lys Glu Arg Ser Met
 1               5                  10

<210> SEQ ID NO 135
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 135

Arg Arg Val Leu Trp Lys Gln Arg Ser Leu
 1               5                  10

<210> SEQ ID NO 136
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

<400> SEQUENCE: 136

Arg Val Ile Cys Ser Lys Lys Ile Ser Leu
 1               5                  10

<210> SEQ ID NO 137
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 137

Arg Val Ile Cys Ser Lys Lys Ile Ser Leu
 1               5                  10

<210> SEQ ID NO 138
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 138

Arg Val Ile Phe Ser Lys Lys Ile Ser Leu
 1               5                  10

<210> SEQ ID NO 139
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 139

Arg Val Ile Ser Ser Lys Lys Ile Ser Leu
 1               5                  10

<210> SEQ ID NO 140
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 140

Arg Val Leu Cys Lys Lys Glu Ile Ser Leu
 1               5                  10

<210> SEQ ID NO 141
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 141

Ser Pro Arg Asn Arg Lys Glu Lys Ser Ser
 1               5                  10

```
<210> SEQ ID NO 142
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 142

Ser Ser Arg Thr Lys Lys Leu Lys Ser Pro
 1               5                  10

<210> SEQ ID NO 143
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 143

Ser Ser Arg Thr Lys Lys Leu Lys Ser Pro
 1               5                  10

<210> SEQ ID NO 144
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 144

Ser Ser Thr Gly Lys Lys Ile Leu Ser Arg
 1               5                  10

<210> SEQ ID NO 145
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 145

Ser Ser Thr Gly Lys Lys Ile Leu Ser Arg
 1               5                  10

<210> SEQ ID NO 146
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 146

Ser Ser Thr Gly Lys Lys Ile Leu Ser Arg
 1               5                  10

<210> SEQ ID NO 147
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 147

Val Lys Lys Thr Ile Lys Arg Ile Thr Ser
1               5                   10

<210> SEQ ID NO 148
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 148

Val Lys Lys Thr Trp Lys Arg Ile Thr Ser
1               5                   10

<210> SEQ ID NO 149
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 149

Val Lys Lys Thr Trp Lys Arg Leu Thr Cys
1               5                   10

<210> SEQ ID NO 150
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 150

Val Lys Lys Thr Trp Lys Arg Leu Thr Cys
1               5                   10

<210> SEQ ID NO 151
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 151

Val Arg Val Leu Ile Lys Lys Ile Ser Leu
1               5                   10

<210> SEQ ID NO 152
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 152

Asn Phe Ser Ser Arg Leu Arg Ile Thr His
1               5                   10
```

```
<210> SEQ ID NO 153
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 153

Asn Phe Ser Ser Arg Leu Arg Ile Thr His
 1               5                  10

<210> SEQ ID NO 154
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 154

Arg Asn Arg Pro Trp Pro Lys Asp Ser Tyr
 1               5                  10

<210> SEQ ID NO 155
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 155

Asp Lys Asn Leu Arg Gln Arg Asn Thr Asn
 1               5                  10

<210> SEQ ID NO 156
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 156

Ala Ala Lys Leu Arg Arg Arg Lys Thr Leu
 1               5                  10

<210> SEQ ID NO 157
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 157

Ala Val Gln Ser Lys Arg Arg Lys Ser Lys
 1               5                  10

<210> SEQ ID NO 158
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 158

Asp Arg Pro Arg Ala Arg Arg Lys Ser Ile
 1               5                  10

<210> SEQ ID NO 159
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 159

Glu Arg Arg Leu Gln Arg Gln Arg Thr Thr
 1               5                  10

<210> SEQ ID NO 160
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 160

His Arg Leu His Leu Arg Arg Lys Ser Ile
 1               5                  10

<210> SEQ ID NO 161
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 161

Ile Arg Arg Arg Lys Arg Ser Val Ser Leu
 1               5                  10

<210> SEQ ID NO 162
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 162

Ile Arg Arg Arg Lys Arg Ser Val Ser Leu
 1               5                  10

<210> SEQ ID NO 163
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 163

Lys Lys Lys Leu Phe Arg Phe Asp Thr Gln
 1               5                  10
```

<210> SEQ ID NO 164
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 164

Lys Thr Leu Asn Arg Arg Ile Phe Ser Ser
 1               5                  10

<210> SEQ ID NO 165
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 165

Lys Thr Leu Ser Arg Arg Leu Cys Ser His
 1               5                  10

<210> SEQ ID NO 166
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 166

Leu Leu Cys His Arg Arg Lys Phe Ser Pro
 1               5                  10

<210> SEQ ID NO 167
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 167

Asn Val Leu Ser Arg Arg Leu Cys Ser Gln
 1               5                  10

<210> SEQ ID NO 168
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 168

Gln Asp Tyr Thr Arg Arg Cys Gly Thr Thr
 1               5                  10

<210> SEQ ID NO 169
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

```
<400> SEQUENCE: 169

Arg Gly Leu Met Lys Arg Arg Ser Ser Val
 1               5                  10

<210> SEQ ID NO 170
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 170

Val Cys Glu Lys Arg Arg Asn Ile Thr His
 1               5                  10

<210> SEQ ID NO 171
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 171

Val Lys Leu Val Arg Arg Lys Ile Ser Ser
 1               5                  10

<210> SEQ ID NO 172
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 172

Asp Ile Arg Glu Lys Ser Lys Cys Ser Gly
 1               5                  10

<210> SEQ ID NO 173
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 173

His Arg Trp Arg Lys Ser Arg Arg Thr Ile
 1               5                  10

<210> SEQ ID NO 174
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 174

Lys Lys Asp Lys Asp Val Arg Val Thr Trp
 1               5                  10
```

```
<210> SEQ ID NO 175
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 175

Arg Arg Arg Ala Asp Val Arg Ile Thr Gly
 1               5                  10

<210> SEQ ID NO 176
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 176

Lys Arg Arg Cys Leu Cys Lys Leu Ser Ser
 1               5                  10

<210> SEQ ID NO 177
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 177

Glu Glu Lys Lys Asp Glu Arg Lys Thr Asp
 1               5                  10

<210> SEQ ID NO 178
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 178

Lys Gly Lys Ser Gly Glu Arg Val Thr Ser
 1               5                  10

<210> SEQ ID NO 179
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 179

Phe Lys Lys Leu Ile Gly Lys Lys Ser Gln
 1               5                  10

<210> SEQ ID NO 180
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 180

Lys Lys Met Thr Arg Gly Arg Gln Ser Ser
1               5                   10

<210> SEQ ID NO 181
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 181

Lys Val Leu Trp Arg Gly Arg Asp Ser Gly
1               5                   10

<210> SEQ ID NO 182
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 182

Ile Leu Leu Lys Lys His Lys Ser Ser His
1               5                   10

<210> SEQ ID NO 183
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 183

Cys Pro Pro Lys Arg Lys Glu Lys Ser Ser
1               5                   10

<210> SEQ ID NO 184
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 184

Glu Arg Arg Leu Gln Lys Gln Gln Thr Ser
1               5                   10

<210> SEQ ID NO 185
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 185

Phe Gly Lys Gly Ala Lys Lys Thr Ser His
1               5                   10
```

```
<210> SEQ ID NO 186
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 186

Ile Arg Arg Tyr Gln Lys Lys Ala Thr Ala
 1               5                  10

<210> SEQ ID NO 187
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 187

Lys Lys Tyr Gly Leu Lys Pro Pro Thr Leu
 1               5                  10

<210> SEQ ID NO 188
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 188

Lys Arg Met Leu Glu Lys Lys Arg Thr Ser
 1               5                  10

<210> SEQ ID NO 189
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 189

Lys Arg Met Leu Glu Lys Lys Arg Thr Ser
 1               5                  10

<210> SEQ ID NO 190
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 190

Leu Ile Glu Asn Leu Lys Lys Ala Ser Gln
 1               5                  10

<210> SEQ ID NO 191
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

-continued

```
<400> SEQUENCE: 191

Ser Pro Arg Asn Lys Lys Glu Lys Ser Ser
1               5                   10

<210> SEQ ID NO 192
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 192

Ser Val Leu Thr Ile Lys Lys Glu Ser Glu
1               5                   10

<210> SEQ ID NO 193
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 193

Tyr Arg Ala Leu Gln Lys Lys Arg Thr Met
1               5                   10

<210> SEQ ID NO 194
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 194

Tyr Ser Ile Cys Glu Lys Lys Phe Ser Met
1               5                   10

<210> SEQ ID NO 195
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 195

Tyr Ser Ile Cys Glu Lys Lys Phe Ser Met
1               5                   10

<210> SEQ ID NO 196
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 196

Tyr Ser Ile Cys Glu Lys Lys Phe Ser Met
1               5                   10
```

```
<210> SEQ ID NO 197
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 197

Arg Asn Arg Pro Trp Pro Lys Asp Ser Tyr
 1               5                  10

<210> SEQ ID NO 198
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 198

Asp Lys Asn Leu Arg Gln Arg Asn Thr Asn
 1               5                  10

<210> SEQ ID NO 199
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 199

Asp Lys Asn Leu Arg Gln Arg Asn Thr Asn
 1               5                  10

<210> SEQ ID NO 200
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 200

His Leu Val Lys Arg Gln Arg Pro Ser Pro
 1               5                  10

<210> SEQ ID NO 201
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 201

Ala Arg Arg Arg Lys Arg Ser Val Ser Leu
 1               5                  10

<210> SEQ ID NO 202
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

-continued

```
<400> SEQUENCE: 202

Ala Val Gln Ser Lys Arg Arg Lys Ser Lys
 1               5                  10

<210> SEQ ID NO 203
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 203

His Leu Leu Asn Arg Arg Phe Phe Ser Lys
 1               5                  10

<210> SEQ ID NO 204
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 204

His Leu Pro Asn Arg Arg Phe Phe Ser Lys
 1               5                  10

<210> SEQ ID NO 205
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 205

Leu Gln Val Arg Gln Arg Leu Gly Ser Leu
 1               5                  10

<210> SEQ ID NO 206
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 206

Gln Asp Tyr Thr Arg Arg Cys Gly Ser Thr
 1               5                  10

<210> SEQ ID NO 207
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 207

Gln Arg Leu Met Lys Arg Arg Lys Ser Val
 1               5                  10
```

```
<210> SEQ ID NO 208
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 208

Arg Gly Leu Met Lys Arg Arg Ser Ser Val
  1               5                  10

<210> SEQ ID NO 209
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 209

Arg Val Met Gln Arg Arg Gln Asp Ser Arg
  1               5                  10

<210> SEQ ID NO 210
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 210

Arg Val Met Gln Arg Arg Gln Asp Ser Arg
  1               5                  10

<210> SEQ ID NO 211
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 211

Arg Val Met Gln Arg Arg Gln Asp Ser Arg
  1               5                  10

<210> SEQ ID NO 212
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 212

Ser Arg Arg Ser Ser Arg Cys Gly Thr Pro
  1               5                  10

<210> SEQ ID NO 213
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 213

Thr Leu Pro Arg Lys Arg Met Ser Ser Ile
 1               5                  10

<210> SEQ ID NO 214
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 214

Lys Val Trp Gly Arg Ser Arg Ala Ser Arg
 1               5                  10

<210> SEQ ID NO 215
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 215

Arg Arg Gln Arg Lys Ser Arg Arg Thr Ile
 1               5                  10

<210> SEQ ID NO 216
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 216

Lys Ala Lys Ala Ala Ala Lys Lys Ser Asp
 1               5                  10

<210> SEQ ID NO 217
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 217

Leu Glu Asn Pro Ala Ala Lys Lys Thr Val
 1               5                  10

<210> SEQ ID NO 218
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 218

Val Asp Asn Phe Asp Ala Lys Lys Thr Glu
 1               5                  10
```

```
<210> SEQ ID NO 219
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 219

Glu His Ala Lys Glu Asp Lys Lys Thr Lys
  1               5                  10

<210> SEQ ID NO 220
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 220

Lys Lys Ser Glu Asp Glu Lys Ile Ser Asn
  1               5                  10

<210> SEQ ID NO 221
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 221

Lys Lys Met Gln Asn Phe Arg Val Ser Thr
  1               5                  10

<210> SEQ ID NO 222
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 222

Phe Glu Val Glu Glu Lys Leu Lys Thr Cys
  1               5                  10

<210> SEQ ID NO 223
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 223

Phe Pro Asn Val Ile Lys Lys Lys Ser Thr
  1               5                  10

<210> SEQ ID NO 224
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

-continued

```
<400> SEQUENCE: 224

Lys Leu Ser Lys Ile Lys Leu Val Ser Cys
1               5                   10

<210> SEQ ID NO 225
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 225

Met Val Gly Ser Ser Lys Ala Lys Ser Glu
1               5                   10

<210> SEQ ID NO 226
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 226

Asn Ala Pro Ser Lys Lys Ser Ile Ser Tyr
1               5                   10

<210> SEQ ID NO 227
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 227

Arg Lys Thr Leu Lys Lys Gln Leu Ser Arg
1               5                   10

<210> SEQ ID NO 228
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 228

Arg Arg Ser Glu Gln Lys Ala Gln Thr Glu
1               5                   10

<210> SEQ ID NO 229
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 229

Ser Ile Leu Val Val Lys Lys Val Thr Ser
1               5                   10
```

```
<210> SEQ ID NO 230
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 230

Ser Ser Ser Asn Gly Lys Lys Asn Ser Arg
 1               5                  10

<210> SEQ ID NO 231
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 231

Glu Val Arg Pro Thr Gln Lys Lys Thr Lys
 1               5                  10

<210> SEQ ID NO 232
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 232

Glu Asn Ser Arg Ser Arg Asn Lys Ser Glu
 1               5                  10

<210> SEQ ID NO 233
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 233

Glu Tyr Asn Gln Arg Arg Ile Leu Ser Leu
 1               5                  10

<210> SEQ ID NO 234
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 234

Ser Gly Lys Arg Glu Arg Lys Lys Ser Glu
 1               5                  10

<210> SEQ ID NO 235
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 235

Trp Pro Glu Arg His Arg Arg Trp Ser Ser
 1               5                  10

<210> SEQ ID NO 236
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 236

Tyr Ser Ala Ser Arg Arg Ala Ser Ser Ala
 1               5                  10

<210> SEQ ID NO 237
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 237

Gln Lys Asn Thr Glu Ser Lys Lys Thr Lys
 1               5                  10

<210> SEQ ID NO 238
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 238

Ser Leu Glu His Arg Ser Arg Asn Thr Leu
 1               5                  10

<210> SEQ ID NO 239
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 239

Asn Asn Gly Lys Glu Thr Lys Lys Thr Lys
 1               5                  10

<210> SEQ ID NO 240
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 240

Ile Lys Arg Lys Asn Val Arg His Thr Asn
 1               5                  10
```

```
<210> SEQ ID NO 241
<211> LENGTH: 18
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 241

His Cys Val Pro Arg Asp Leu Ser Trp Leu Asp Leu Glu Ala Asn Met
 1               5                  10                  15

Cys Leu

<210> SEQ ID NO 242
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 242

Glu Cys Asp Ala Ala Glu Gly Ala Glu Asn
 1               5                  10

<210> SEQ ID NO 243
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 243

Glu Ala Glu Ala Gly Glu Gly Gly Glu Asn
 1               5                  10

<210> SEQ ID NO 244
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 244

Gln Gln Asp Glu Glu Ala Gly Glu Gly Asn
 1               5                  10

<210> SEQ ID NO 245
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 245

Gln Asp Asp Asp Gly Gly Glu Gly Asn Asn
 1               5                  10

<210> SEQ ID NO 246
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif
```

```
<400> SEQUENCE: 246

Ala Leu Gln Asp Val Glu Asp Glu Asn Gln
  1               5                  10

<210> SEQ ID NO 247
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 247

Asp Glu Gly Asp Ala Gly Glu Gly Glu Asn
  1               5                  10

<210> SEQ ID NO 248
<211> LENGTH: 10
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 248

Gly Gly Glu Ala Pro Gln Glu Pro Gln Ser
  1               5                  10

<210> SEQ ID NO 249
<211> LENGTH: 6
<212> TYPE: PRT
<213> ORGANISM: Unknown Organism
<220> FEATURE:
<223> OTHER INFORMATION: Description of Unknown Organism: Forward
      transport sequence motif

<400> SEQUENCE: 249

Phe Cys Tyr Glu Asn Glu
  1               5

<210> SEQ ID NO 250
<211> LENGTH: 4
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 250

Ser Trp Thr Tyr
  1

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Arg Lys Arg Ser Trp Thr Tyr
  1               5
```

```
<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Arg Lys Arg Arg Gly Arg Ser Trp Thr Tyr
 1               5                  10

<210> SEQ ID NO 253
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ser Trp Thr Tyr Ala Ala Ala
 1               5

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ser Ile Ser Pro Asp Ser Leu Ser
 1               5

<210> SEQ ID NO 255
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: phosphorylated Thr

<400> SEQUENCE: 255

Arg Gly Arg Ser Trp Thr Tyr
 1               5

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: phosphorylated Thr

<400> SEQUENCE: 256

Arg Gly Arg Ser Trp Thr Tyr Ala Ala Ala
 1               5                  10
```

```
<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Arg Ala Ala Ser Trp Thr Tyr
 1               5

<210> SEQ ID NO 258
<211> LENGTH: 5
<212> TYPE: PRT
<213> ORGANISM: Unknown Organism
<220> FEATURE:
<223> OTHER INFORMATION: Description of Unknown Organism: C-terminal
      sequence of KCNK3 or GPR15

<400> SEQUENCE: 258

Arg Arg Ser Ser Val
 1               5

<210> SEQ ID NO 259
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Arg Gly Arg Ser Trp Ala Tyr
 1               5

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 260

Gly Gly Gly Gly Ser Gly Gly Gly Gly Ser Gly Gly Gly Gly Ser
 1               5                  10                  15

<210> SEQ ID NO 261
<211> LENGTH: 36
<212> TYPE: PRT
<213> ORGANISM: Mus musculus

<400> SEQUENCE: 261

Leu Leu Asp Ala Leu Thr Leu Ala Ser Ser Arg Gly Pro Leu Arg Lys
 1               5                  10                  15

Arg Ser Val Ala Val Ala Lys Ala Lys Pro Lys Phe Ser Ile Ser Pro
                20                  25                  30

Asp Ser Leu Ser
            35

<210> SEQ ID NO 262
<211> LENGTH: 19
<212> TYPE: DNA
<213> ORGANISM: Artificial Sequence
```

-continued

<220> FEATURE:
<223> OTHER INFORMATION: Description of Artificial Sequence: Synthetic
      oligonucleotides

<400> SEQUENCE: 262
tgtatgtagc ggccgccta 19

<210> SEQ ID NO 263
<211> LENGTH: 9
<212> TYPE: PRT
<213> ORGANISM: Influenza A virus

<400> SEQUENCE: 263

Tyr Pro Tyr Asp Val Pro Asp Tyr Ala
1 5

<210> SEQ ID NO 264
<211> LENGTH: 4
<212> TYPE: PRT
<213> ORGANISM: Unknown Organism
<220> FEATURE:
<223> OTHER INFORMATION: Description of Unknown Organism: Biomolecule
      partition motif

<400> SEQUENCE: 264

Ser Trp Ala Tyr
1

<210> SEQ ID NO 265
<211> LENGTH: 9
<212> TYPE: PRT
<213> ORGANISM: Unknown Organism
<220> FEATURE:
<223> OTHER INFORMATION: Description of Unknown Organism: C-terminal
      sequence of KCNK3

<400> SEQUENCE: 265

Leu Met Lys Lys Arg Arg Ser Ser Val
1 5

<210> SEQ ID NO 266
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Met Cys Ala Val Arg Gly Trp Cys
1 5

<210> SEQ ID NO 267
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Lys Cys Val Arg Ser Gln Trp Cys
1 5

```
<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ala Glu Val Gln Arg Val Trp Cys
 1               5

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Arg Ile Trp Val Pro Thr Trp Cys
 1               5

<210> SEQ ID NO 270
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gly Arg Arg Leu Phe Gly Trp Cys
 1               5

<210> SEQ ID NO 271
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Met Arg Leu Trp Gly Met Trp Cys
 1               5

<210> SEQ ID NO 272
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ser Phe Leu Ser Ser Gln Trp Cys
 1               5

<210> SEQ ID NO 273
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 273

Met Ile Leu Val Ser Met Ile Cys
  1               5

<210> SEQ ID NO 274
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Arg Asn Met Glu Asn Trp Cys
  1               5

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Cys Arg Ile Arg Gly Gln Trp Cys
  1               5

<210> SEQ ID NO 276
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Leu Lys Ser Leu Lys Glu Trp Cys
  1               5

<210> SEQ ID NO 277
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Asp Arg Val Leu Arg Leu Trp Cys
  1               5

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Lys Ala Leu Lys Gly Val Trp Cys
  1               5
```

```
<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Trp Lys Leu Val Cys Ser Phe Cys
 1               5

<210> SEQ ID NO 280
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Glu Lys Met Gly Arg Leu Ile Cys
 1               5

<210> SEQ ID NO 281
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Glu Ser Thr Arg Arg Val Thr Val
 1               5

<210> SEQ ID NO 282
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gly Asn Ala Arg Ser Leu Thr Val
 1               5

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Pro Gly His Gly Ser Leu Lys Gly
 1               5

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 284

Glu Arg Arg Pro His Ser Trp Gly
 1               5

<210> SEQ ID NO 285
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Arg Cys Arg Gly Val Asn Cys Lys
 1               5

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ser Ala Ala Arg Tyr Gln Thr Ser
 1               5

<210> SEQ ID NO 287
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Met Trp Leu Val Gly Cys Ile Trp
 1               5

<210> SEQ ID NO 288
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Asn Arg Glu Thr Glu Glu His Leu
 1               5

<210> SEQ ID NO 289
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Glu Val Ala Thr Ser Gln Arg Leu
 1               5
```

```
<210> SEQ ID NO 290
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gly Gln Arg Pro Ala Ser Trp Pro
 1               5

<210> SEQ ID NO 291
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Pro Cys Arg Ser Trp Pro Leu Lys
 1               5

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Trp Phe Ile Ala Gln Phe Phe Ser
 1               5

<210> SEQ ID NO 293
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Gln His Val Arg Ser Ala Pro Trp
 1               5

<210> SEQ ID NO 294
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Glu Ile Gly Leu Glu Met Ser Ala
 1               5

<210> SEQ ID NO 295
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 295

Leu Pro Gln Leu Ser Val Thr Trp
 1               5

<210> SEQ ID NO 296
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Thr Ile Gln Thr Leu Asn Gln Ile
 1               5

<210> SEQ ID NO 297
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Arg Lys Arg Trp Gly Met Ile Ile
 1               5

<210> SEQ ID NO 298
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Asp Val Glu Ser Trp Cys Arg Arg
 1               5

<210> SEQ ID NO 299
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Asn Gly Asn Glu Gly Gln Asn Ser
 1               5

<210> SEQ ID NO 300
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Glu Val Arg Arg Arg Val Thr Trp
 1               5
```

```
<210> SEQ ID NO 301
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Glu Lys Tyr Leu Gln Leu Leu Asp
 1               5

<210> SEQ ID NO 302
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Asp Glu Ala Pro Met Met Gly Met
 1               5

<210> SEQ ID NO 303
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Glu Val Met Gly Ala Ala Ala Trp
 1               5

<210> SEQ ID NO 304
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Met Gln Pro Arg Trp Met Val His
 1               5

<210> SEQ ID NO 305
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Asp Arg Leu Gly Asp Asp Thr Arg
 1               5

<210> SEQ ID NO 306
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 306

Thr Met Leu Ser Lys Thr Ile Tyr
1               5

<210> SEQ ID NO 307
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gly Leu Lys Trp Asp Val Arg Trp
1               5

<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Asp Met Leu Arg Ser His Trp Cys
1               5

<210> SEQ ID NO 309
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Arg Met Val Tyr Ser Gly Trp Cys
1               5

<210> SEQ ID NO 310
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Leu Ser Val Val Glu Arg Trp Cys
1               5

<210> SEQ ID NO 311
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gly Tyr Ile Val Ser Ile Trp Cys
1               5
```

```
<210> SEQ ID NO 312
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Arg Arg Ala Lys Asn Phe Trp Cys
  1               5

<210> SEQ ID NO 313
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Val Leu Phe Met Arg His Trp Cys
  1               5

<210> SEQ ID NO 314
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Asp Arg Val Leu Arg Leu Trp Cys
  1               5

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Val Val Leu Ala Gln Met Ile Cys
  1               5

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Glu Thr Leu Ala Ser Trp Asp Cys
  1               5

<210> SEQ ID NO 317
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 317

Glu Trp Val Trp Arg Tyr Leu Val
  1               5

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Arg Ser Arg Gly Cys Lys Thr Val
  1               5

<210> SEQ ID NO 319
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Met Ser Asp Arg Ala Met Thr Val
  1               5

<210> SEQ ID NO 320
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Leu Trp Tyr Met Ser Asn His Gly
  1               5

<210> SEQ ID NO 321
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Trp Tyr Val Leu Gly Leu Leu Ala
  1               5

<210> SEQ ID NO 322
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Glu Met Ser Thr Ile Trp Trp Leu
  1               5
```

```
<210> SEQ ID NO 323
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Ile Arg Val Ser Val Gly Leu Ser
 1               5

<210> SEQ ID NO 324
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Pro Leu Val Leu Arg Trp Ile Arg
 1               5

<210> SEQ ID NO 325
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Ala Arg Gly Arg Ser Trp Thr Tyr
 1               5

<210> SEQ ID NO 326
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Phe Arg Gly Arg Ala Trp Thr Tyr
 1               5

<210> SEQ ID NO 327
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Phe Arg Gly Arg Ser Ala Thr Tyr
 1               5

<210> SEQ ID NO 328
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 328

Phe Arg Ala Arg Ser Trp Thr Tyr
 1               5

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Arg Lys Arg Phe Arg Gly Arg Ser Trp Thr Tyr
 1               5                   10

<210> SEQ ID NO 330
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Phe Arg Gly Arg Ser Trp Thr Ala
 1               5

<210> SEQ ID NO 331
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Arg Lys Arg Arg Gly Arg Ser Trp Thr Tyr Ala Ala Ala
 1               5                   10

<210> SEQ ID NO 332
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Gly His Gly Arg Gly His Ser Trp
 1               5
```